(12) United States Patent
Carpenter et al.

(10) Patent No.: US 11,505,798 B2
(45) Date of Patent: Nov. 22, 2022

(54) METHODS AND COMPOSITIONS FOR TREATING INFLAMMATORY DISEASES

(71) Applicant: The Regents of the University of California, Oakland, CA (US)

(72) Inventors: Susan Carpenter, Santa Cruz, CA (US); Apple Vollmers, Santa Cruz, CA (US); Sergio Covarrubias, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 6 days.

(21) Appl. No.: 17/029,946

(22) Filed: Sep. 23, 2020

(65) Prior Publication Data
US 2021/0087563 A1 Mar. 25, 2021

Related U.S. Application Data

(60) Provisional application No. 62/904,336, filed on Sep. 23, 2019.

(51) Int. Cl.
*C12N 15/113* (2010.01)
*A61P 37/02* (2006.01)

(52) U.S. Cl.
CPC .......... *C12N 15/113* (2013.01); *A61P 37/02* (2018.01); *C12N 2310/113* (2013.01); *C12N 2310/14* (2013.01); *C12N 2310/141* (2013.01); *C12N 2310/321* (2013.01); *C12N 2320/51* (2013.01)

(58) Field of Classification Search
CPC ............ C12N 15/113; C12N 2310/315; C12N 2310/321; C12N 2310/3521; C12N 2320/30; A61P 37/02
See application file for complete search history.

(56) References Cited

U.S. PATENT DOCUMENTS

2003/0228688 A1* 12/2003 Dobie ................ C12N 15/1137
435/375

OTHER PUBLICATIONS

Mo et al. (Frontiers in Immunology, Apr. 2018 vol. 9:1-11, plus Supplementary Information/Materials).*

* cited by examiner

*Primary Examiner* — Terra C Gibbs
(74) *Attorney, Agent, or Firm* — Kilpatrick Townsend & Stockton LLP

(57) ABSTRACT

The disclosure is directed to inhibitory agents that hybridize to a GAPLINC RNA and inhibit or reduce the expression of the GAPLINC RNA. The GAPLINC RNA is a long non-coding RNA (lncRNA) located on chromosome 18 between the protein-coding genes Tgif and Dlgap1. The disclosure also features pharmaceutical compositions including the inhibitory agents and methods of using the inhibitory agents to treat an inflammatory disease, such as sepsis.

19 Claims, 49 Drawing Sheets
Specification includes a Sequence Listing.

| Isoform number | Read counts | Percent % |
|---|---|---|
| 1 | 8 | 4.9 |
| 2 | 4 | 2.5 |
| 3 | 91 | 55.8 |
| 4 | 55 | 33.7 |
| 5 | 3 | 1.8 |
| 6 | 2 | 1.2 |

| | Gene symbol | KO_fold-change |
|---|---|---|
| 1 | Ccl12 | 2.3 |
| 2 | AC102225.2 | 2.2 |
| 3 | Lipg | 3.1 |
| 4 | Serpinb2 | 2.9 |
| 5 | RP23-154O12.1 | 2.6 |
| 6 | RP24-50I4.2 | 3.9 |
| 7 | Nos2 | 5.5 |
| 8 | Gbp5 | 2.9 |
| 9 | RP24-50I4.1 | 3.1 |
| 10 | Ifit1bl1 | 2.4 |
| 11 | Il6 | 7.1 |
| 12 | Iigp1 | 3.2 |
| 13 | Cxcl10 | 3 |
| 14 | Il1a | 8.1 |
| 15 | Gbp10 | 2.3 |
| 16 | Il1b | 5.2 |
| 17 | Mid1 | 2.5 |
| 18 | Edn1 | 2.5 |
| 19 | Cd69 | 2.2 |
| 20 | RP23-129D21.1 | 15.5 |
| 21 | Stxbp6 | 2.5 |
| 22 | Mrc1 | 2.2 |
| 23 | Slco2b1 | 2.3 |

Primary murine macrophages

Mass spectrometry candidates

| | Total Spectrum Count | | |
|---|---|---|---|
| | LacZ probes | GAPLINC probes | |
| Protein ID | WT | WT | GAPLINC-KO |
| TRY1 | 36 | 40 | 40 |
| IGHG | 28 | 22 | 32 |
| PCCA | 0 | 22 | 35 |
| PLAK | 7 | 11 | 8 |
| DESP | 0 | 5 | 2 |
| ALBU_BOV | 0 | 2 | 0 |
| CH60 | 0 | 5 | 4 |
| GRP75 | 0 | 4 | 3 |
| CTRA | 0 | 0 | 0 |
| H4 | 0 | 0 | 2 |
| H3C | 0 | 2 | 2 |
| PCCB | 0 | 0 | 2 |
| MDHM | 0 | 3 | 2 |
| ALDH2 | 0 | 3 | 0 |
| ALBU_RAB | 0 | 0 | 0 |
| Q8IFZ8 | 2 | 3 | 0 |
| Q8CZU6 | 0 | 2 | 0 |
| P16858 | 0 | 0 | 0 |
| Q61495 | 0 | 0 | 0 |
| ANXA2 | 0 | 0 | 0 |
| Q8CUK9 | 2 | 0 | 0 |
| Q7B2Z0 | 2 | 2 | 0 |
| Q7B2Y9 | 2 | 2 | 0 |
| Q3UZ07 | 2 | 3 | 2 |
| P70696 | 2 | 2 | 2 |
| P80710 | 2 | 3 | 2 |
| Q8CGP0 | 2 | 2 | 2 |
| Q7TSF1 | 0 | 0 | 0 |

SEQUENCE LISTING

<160> NUMBER OF SEQ ID NOS: 19

<210> SEQ ID NO 1
<211> LENGTH: 1051
<212> TYPE: DNA
<213> ORGANISM: Homo sapiens

<400> SEQUENCE: 1

| | | | | | |
|---|---|---|---|---|---|
| acttgcagga | tctgacacat | cctcttggtt | tcctaagtct | tatgactagc | caatgcctga | 60 |
| aataatgaac | tcctccaagg | caagaaatct | gttttgaagc | ttctctgcgt | tcacacacag | 120 |
| cagcctggtt | tcctggaagg | gcattttcca | cattgtgcgt | tatggatgat | catcccaggc | 180 |
| atcaggtgtg | aagccctgca | tccacatcca | ggggctatca | aatctctctg | caaaaggaga | 240 |
| agctggactc | aggcacgttt | acagtgatgt | gtatgcaggc | tggaatgcag | ggatgcgatc | 300 |
| tcggctcaat | gcaacctctg | ccgcccagga | ttcaagcgat | tctcctgcct | cagcttcttg | 360 |
| agtatctggg | attacaggca | cctgccacca | cgcctgacta | ttttttgtag | ttttagtaga | 420 |
| gccagggttt | caccatcttg | gccaggctgg | tcttgaactc | ctgacctcgt | gatccaccca | 480 |
| ccttgtcttc | ccaaagtgct | gcgattacag | gcgtgagcca | ccgtgcccgg | ctgaccagta | 540 |
| tctttcatgt | tactattgta | attgtttggg | gtcaccacga | accgcacaca | tataagacaa | 600 |
| tgaacttaat | caataaacgt | gtgtgttctg | attgctccat | tctgtgaagg | aagctgcaga | 660 |
| agaaaaggt | gaaagaggtg | aggaagctgc | agaagaaaac | ctggaagtta | gcagagcttg | 720 |
| atccagaggt | ttaaggaaag | aagccatctc | cataacataa | aagtgcaagg | tgaagcagca | 780 |
| agtgctgatg | gggaagctgc | agcaagtcat | ccagaagatc | ttgctaaggg | tatgcacaga | 840 |
| tgtggaaaca | ggaactgatg | tgtccattac | accactagga | cagaggccag | aacaatgaag | 900 |
| aaaccaaata | cttggaagag | ggtagagata | atgaatggag | tccaagagcc | ctgattgtgc | 960 |
| cataaatgtc | cagataattc | catacctgag | gattatgtgg | tttgtaaact | tggcacttag | 1020 |
| aagaaccaat | aaaatcatgt | tatagtttca | a | | | 1051 |

<210> SEQ ID NO 2
<211> LENGTH: 385
<212> TYPE: DNA
<213> ORGANISM: Mus sp.

<400> SEQUENCE: 2

| | | | | | |
|---|---|---|---|---|---|
| agctcgggaa | gcctgcaggc | tgtgagcacg | ttgatcaaag | gtccctttgc | gggctcaaat | 60 |
| taacagggag | ctggcgagcc | cgcgcagcac | ctgcctggga | agagcagcgc | cacagcaaac | 120 |
| cggctcatct | tgccgggagt | atttggaaat | gaaccttgga | cttttaagaac | gcttggagtc | 180 |
| attgaaccac | acccaactcc | tattctgaca | tttcactgct | atccaggatt | tacagaaaat | 240 |
| gttagaaaaa | ctctgcagca | atgttatttt | gaaatttata | aagcctttac | aaaaatgtga | 300 |
| agaaagatgt | atatatttgt | ggcatcttga | tctctactat | aaattgcgaa | atgattggat | 360 |
| tgagcttaag | gtattaaagc | tttta | | | | 385 |

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 3
auguggatgc agggcuucac                                           20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4 auuggaaaa tgcccuucca                                            20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
aguccagcuu ctcctuuugc                                           20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
cuugccttgg aggaguucau                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
gaugcctggg atgatcaucc                                           20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 8
gaacaaugaa gaaaccaaat t                                              21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 9
uuugguuucu ucauuguuct g                                              21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
gaagaaaacc uggaaguuat t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
gaagaaaacc uggaaguuat t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
ggauuaugug guuuguaaat t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 13
uuuacaaacc acauaaucct c                                              21

<210> SEQ ID NO 14
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
gaacaaugaa gaaaccaaa                                                 19

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
uuugguuucu ucauuguuc                                                 19

<210> SEQ ID NO 16
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gaagaaaacc uggaaguua                                                 19

<210> SEQ ID NO 17
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
gaagaaaacc uggaaguua                                                 19

<210> SEQ ID NO 18
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
ggauuaugug guuuguaaa                                                 19

<210> SEQ ID NO 19
<211> LENGTH: 19
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 19
uuuacaaacc acauaaucc                                                    19

METHODS AND COMPOSITIONS FOR TREATING INFLAMMATORY DISEASES

CROSS-REFERENCES TO RELATED APPLICATIONS

This application claims priority to U.S. Provisional Application No. 62/904,336, filed Sep. 23, 2019, the disclosure of which is hereby incorporated by reference in its entirety for all purposes.

STATEMENT AS TO RIGHTS TO INVENTIONS MADE UNDER FEDERALLY SPONSORED RESEARCH AND DEVELOPMENT

This invention was made with Government support under Grant No. R21AR070973, awarded by the National Institutes of Health. The Government has certain rights in this invention.

The instant application contains a Sequence Listing which has been submitted electronically in ASCII format and is hereby incorporated by reference in its entirety. Said ASCII copy, created on Dec. 1, 2020, is named 102913-002010US-1203826 SL.txt and is 7,385 bytes in size.

BACKGROUND

Mammalian genomes are more pervasively transcribed than previously expected. In addition to the protein-coding regions of genes, much of the genome is transcribed as non-coding RNAs (ncRNAs). These non-coding genomic transcripts include many different types of small regulatory ncRNAs and long ncRNAs (lncRNAs). Long ncRNAs vary in length from several hundred bases to tens of kilo bases and may be located separately from protein-coding genes (long intergenic ncRNAs or lincRNAs), or reside near or within protein-coding genes. A number of the identified lncRNAs are differentially expressed in association with transcriptional regulation, cell proliferation, differentiation, and/or apoptosis and could have important roles in regulating cell function. Such lncRNAs may potentially be useful diagnostically or therapeutically; however, the functions of only a few of these lncRNAs have been studied in detail, and many more functional lncRNAs have yet to be discovered.

SUMMARY

Disclosed herein are methods and compositions that involve the inhibition of the GAPLINC lncRNA, as described in, e.g., Hu Y et al, *Cancer Res* 74, 6890-6902, 2014, which is incorporated by reference herein, for use in treating inflammatory diseases, such as sepsis.

In one aspect, the disclosure features an inhibitory agent comprising at least 10 (e.g., at least 15, 20, 25, 30, 35, 40, 45, or 50) nucleosides in length, wherein the inhibitory agent is complementary to an equal length portion of a sequence of a GAPLINC RNA, wherein the inhibitory agent inhibits the expression of the GAPLINC RNA.

In some embodiments, the GAPLINC RNA is a human GAPLINC RNA or a mouse GAPLINC RNA. In certain embodiments, the GAPLINC RNA is a human GAPLINC RNA that has a sequence having at least 90% (e.g., 92%, 94%, 96%, 98%, or 100%) identity to the sequence of:

(SEQ ID NO: 1)
ACTTGCAGGATCTGACACATCCTCTTGGTTTCCTAAGTCTTATGACTAGC

CAATGCCTGAAATAATGAACTCCTCCAAGGCAAGAAATCTGTTTTGAAGC

TTCTCTGCGTTCACACACAGCAGCCTGGTTTCCTGGAAGGGCATTTTCCA

CATTGTGCGTTATGGATGATCATCCCAGGCATCAGGTGTGAAGCCCTGCA

TCCACATCCAGGGGCTATCAAATCTCTCTGCAAAAGGAGAAGCTGGACTC

AGGCACGTTTACAGTGATGTGTATGCAGGCTGGAATGCAGGGATGCGATC

TCGGCTCAATGCAACCTCTGCCGCCCAGGATTCAAGCGATTCTCCTGCCT

CAGCTTCTTGAGTATCTGGGATTACAGGCACCTGCCACCACGCCTGACTA

ATTTTTGTAGTTTTAGTAGAGCCAGGGTTTCACCATCTTGGCCAGGCTGG

TCTTGAACTCCTGACCTCGTGATCCACCCACCTTGTCTTCCCAAAGTGCT

GCGATTACAGGCGTGAGCCACCGTGCCCGGCTGACCAGTATCTTTCATGT

TACTATTGTAATTGTTTGGGGTCACCACGAACCGCACACATATAAGACAA

TGAACTTAATCAATAAACGTGTGTGTTCTGATTGCTCCATTCTGTGAAGG

AAGCTGCAGAAGAAAAAGGTGAAAGAGGTGAGGAAGCTGCAGAAGAAAAC

CTGGAAGTTAGCAGAGCTTGATCCAGAGGTTTAAGGAAAGAAGCCATCTC

CATAACATAAAAGTGCAAGGTGAAGCAGCAAGTGCTGATGGGGAAGCTGC

AGCAAGTCATCCAGAAGATCTTGCTAAGGGTATGCACAGATGTGGAAACA

GGAACTGATGTGTCCATTACACCACTAGGACAGAGGCCAGAACAATGAAG

AAACCAAATACTTGGAAGAGGGTAGAGATAATGAATGGAGTCCAAGAGCC

CTGATTGTGCCATAAATGTCCAGATAATTCCATACCTGAGGATTATGTGG

TTTGTAAACTTGGCACTTAGAAGAACCAATAAAATCATGTTATAGTTTCA

A.

In certain embodiments, the GAPLINC RNA is a mouse GAPLINC RNA that has a sequence having at least 90% (e.g., 92%, 94%, 96%, 98%, or 100%) identity to the sequence of:

(SEQ ID NO: 2)
AGCTCGGGAAGCCTGCAGGCTGTGAGCACGTTGATCAAAGGTCCCTTTGC

GGGCTCAAATTAACAGGGAGCTGGCGAGCCCGCGCAGCACCTGCCTGGGA

AGAGCAGCGCCACAGCAAACCGGCTCATCTTGCCGGGAGTATTTGGAAAT

GAACCTTGGACTTTAAGAACGCTTGGAGTCATTGAACCACACCCAACTCC

TATTCTGACATTTCACTGCTATCCAGGATTTACAGAAAATGTTAGAAAAA

CTCTGCAGCAATGTTATTTTGAAATTTATAAAGCCTTTACAAAAATGTGA

AGAAAGATGTATATATTTGTGGCATCTTGATCTCTACTATAAATTGCGAA

ATGATTGGATTGAGCTTAAGGTATTAAAGCTTTTA.

In some embodiments, the inhibitory agent comprises between 15 and 30 (e.g., between 15 and 28, between 15 and 26, between 15 and 24, between 15 and 22, between 15 and 20, between 15 and 18, between 15 and 16, between 16 and 30, between 18 and 30, between 20 and 30, between 22 and 30, between 24 and 30, between 26 and 30, or between 28 and 30) nucleosides in length).

The inhibitory agent can comprise an antisense oligonucleotide (ASO), an siRNA, an miRNA, or an shRNA.

In certain embodiments, the inhibitory agent comprises an ASO. For example, an ASO can have comprise a sequence having at least 90% identity to a sequence of any one of: AUGUGGAUGCAGGGCUUCAC (SEQ ID NO:3), AUGUGGAAAAUGCCCUUCCA (SEQ ID NO:4), AGUCCAGCUUCUCCUUUUGC (SEQ ID NO:5), CUUGCCUUGGAGGAGUUCAU (SEQ ID NO:6), and GAUGCCUGGGAUGAUCAUCC (SEQ ID NO:7). Specifically, the ASO can comprise a sequence of any one of SEQ ID NOS:3-7.

In certain embodiments, the inhibitory agent comprises an siRNA. For example, the siRNA can be a double-stranded siRNA comprising a sense region and an antisense region. An antisense region can comprise a sequence having at least 90% identity to a sequence of any one of: UUUGGUUUCUUCAUUGUUCTG (SEQ ID NO:9), GAAGAAAACCUGGAAGUUAUU (SEQ ID NO:11), UUUACAAACCACAUAAUCCTC (SEQ ID NO:13), UUUGGUUUCUUCAUUGUUC (SEQ ID NO:15), GAAGAAAACCUGGAAGUUA (SEQ ID NO:17), and UUUACAAACCACAUAAUCC (SEQ ID NO:19). Specifically, the antisense region can comprise a sequence of any one of SEQ ID NOS: 9, 11, 13, 15, 19, and 19. A sense region can comprise a sequence having at least 90% identity to a sequence of: GAACAAUGAAGAAACCAAAUU (SEQ ID NO:8), GAAGAAAACCUGGAAGUUAUU (SEQ ID NO:10), GGAUUAUGUGGUUUGUAAAUU (SEQ ID NO:12), GAACAAUGAAGAAACCAAA (SEQ ID NO:14), GAAGAAAACCUGGAAGUUA (SEQ ID NO:16), and GGAUUAUGUGGUUUGUAAA (SEQ ID NO:18). Specifically, the sense region can comprise a sequence of any one of SEQ ID NOS:8, 10, 12, 14, 16, and 18.

In some embodiments of this aspect, the inhibitory agent further comprises at least one modified nucleobase. In some embodiments, the inhibitory agent comprises at least one modified internucleoside linkage (e.g., a phosphorothioate linkage). In some embodiments, the inhibitory agent comprises at least one modified sugar (e.g., a modified sugar comprising a 2' OMe.

In other embodiments of this aspect, the inhibitory agent comprises a phosphorodiamidate morpholino oligomer (PMO). The inhibitory agent can also comprise a peptide nucleic acid.

In specific embodiments of this aspect, the inhibitory agent is an ASO that comprises at least one (e.g., at least five or at least ten; e.g., two, three, four, five, six, seven, eight, nine, or ten) modified nucleotide comprising a 2'-OMe. Specifically, in some embodiments, the first five nucleotides from the 5' terminus of a sequence of any one of SEQ ID NOS:3-7 each comprises a modified nucleotide comprising a 2' OMe. Specifically, in some embodiments, the last five nucleotides from the 5' terminus of a sequence of any one of SEQ ID NOS:3-7 each comprises a modified nucleotide comprising a 2' OMe. Specifically, in some embodiments, the first five nucleotides and last five nucleotides from the 5' terminus of a sequence of any one of SEQ ID NOS:3-7 each comprises a modified nucleotide comprising a 2' OMe.

In specific embodiments of this aspect, the inhibitory agent is an ASO (e.g., an ASO having a sequence of any one of SEQ ID NOS:3-7) that comprises at least one phosphorothioate linkage. In certain embodiments, at least 10% (e.g., 15%, 20%, 25%, 30%, 35%, 40%, 45%, or 50%) of the internucleoside linkages of an ASO (e.g., an ASO having a sequence of any one of SEQ ID NOS:3-7) are phosphorothioate linkages. In certain embodiments, all of the internucleoside linkages of an ASO (e.g., an ASO having a sequence of any one of SEQ ID NOS:3-7) are phosphorothioate linkages.

In another aspect, the disclosure features a pharmaceutical composition comprising an inhibitory agent described herein and one or more pharmaceutically acceptable carriers or excipients. The pharmaceutical composition can be used for treating an inflammatory disease (e.g., sepsis).

In another aspect, the disclosure features a method of treating an inflammatory disease in a subject by administering to the subject a therapeutically effective amount of an inhibitory agent described herein or a pharmaceutical composition described herein, wherein the inhibitory agent inhibits the expression of a GAPLINC RNA (e.g., a GAPLINC RNA having the sequence of SEQ ID NO:1 or 2). Examples of inflammatory diseases include, but are not limited to, sepsis, multiple sclerosis, rheumatoid arthritis, intestinal bowel disease, and systemic lupus erythematosus.

In another aspect, the disclosure also features a method of inhibiting the expression of a GAPLINC RNA (e.g., a GAPLINC RNA having the sequence of SEQ ID NO:1 or 2) in a subject by administering to the subject a therapeutically effective amount of an inhibitory agent described herein or a pharmaceutical composition described herein, wherein the inhibitory agent inhibits the expression of the GAPLINC RNA.

Definitions

As used herein, the term "long noncoding RNA" or "lncRNA" refers to RNA polynucleotides that are not translated into proteins. Long ncRNAs may vary in length from several hundred bases to tens of kilo bases (e.g., at least 100, 200, 300, 400, 500, 600, 700, 800, 900, 1000, 1100, 1200, 1300, 1400, 1500, 1600, 1700, 1800, 1900, or 2000 bases) and may be located separately from protein coding genes, or reside near or within protein coding genes.

As used herein, the term "inhibitory agent" refers to a molecule that inhibits or reduces the expression of a GAPLINC RNA, such as a human or mouse GAPLINC RNA (e.g., a GAPLINC RNA having a sequence of SEQ ID NO:1 or 2). An inhibitory agent can be naturally occurring or synthetic. An inhibitory agent can be an antisense oligonucleotide (ASO), an siRNA, an miRNA, or an shRNA. In some embodiments, the inhibitory agent can inhibit or reduce the expression of the GAPLINC RNA by preventing the GAPLINC RNA from being transcribed. In other embodiments, the inhibitory agent can inhibit or reduce the expression of the GAPLINC RNA by preventing the GAPLINC RNA from being translated.

As used herein, the term "hybridize" or "hybridization" refers to the annealing of complementary nucleic acids (i.e., an inhibitory agent (e.g., an ASO) and its target nucleic acid) through hydrogen bonding interactions that occur between complementary nucleobases, nucleosides, or nucleotides. The hydrogen bonding interactions may be Watson-Crick hydrogen bonding or Hoogsteen or reverse Hoogsteen hydrogen bonding. Examples of complementary nucleobase pairs include, but are not limited to, adenine and thymine, cytosine and guanine, and adenine and uracil, which all pair through the formation of hydrogen bonds.

As used herein, the term "complementary" refers to the capacity for precise pairing between nucleobases, nucleosides, or nucleotides. For example, if a nucleoside at a certain position of an inhibitory agent (e.g., an ASO) is capable of hydrogen bonding with a nucleoside at the same position of the target nucleic acid sequence of the inhibitory agent, then the inhibitory agent and its target nucleic acid sequence are considered to be complementary at that position.

As used herein, the term "nucleobase" refers to a heterocyclic base moiety capable of forming hydrogen bonds with another nucleobase. Nucleobases provide the hydrogen bonding interactions that are needed bind or hybridize one nucleic acid strand to another in a sequence specific manner. A nucleobase may be a naturally occurring nucleobase (e.g., adenine, guanine, cytosine, thymine, or uracil) or a modified nucleobase. Examples of modified nucleobases are described in detail further herein.

As used herein, the term "nucleoside" refers to a nucleobase linked to a sugar (e.g., a pentofuranosyl sugar). A nucleoside may be a naturally occurring nucleoside (e.g., adenosine, guanosine, cytidine, 5-methyluridine, or uridine) or a modified nucleoside. A modified nucleoside includes a modified nucleobase and/or a modified sugar. Examples of modified nucleobases and modified sugars are described in detail further herein.

As used herein, the term "nucleotide" refers a nucleobase covalently linked to a sugar and a 5' functional moiety (e.g., a phosphorous moiety). In other words, a nucleotide includes a nucleoside and a 5' functional moiety (e.g., a phosphorous moiety) covalently linked to the 5' carbon of the sugar portion of the nucleoside. A 5' functional moiety in a nucleotide refers to a functional group that is covalently attached to the 5' carbon of the sugar and generally serves to connect neighboring nucleotides (i.e., the functional moiety joined to the 5' carbon of the sugar of one nucleoside is covalently linked to the 3' carbon of the sugar of the adjacent nucleoside). An example of a 5' functional moiety is a phosphorous moiety, which refers to a phosphorous-containing functional moiety that is covalently linked to the 5' carbon of the sugar and functions to connect neighboring nucleotides. Examples of phosphorous moieties include, but are not limited to, a phosphate, a phosphorothioate, a phosphorodithioate, a phosphoramidate, a phosphorodiamidate, a thiophosphoramidate, and a thiophosphorodiamidate. The 5' functional moiety (e.g., a phosphorous moiety) of a nucleotide forms part of the internucleoside linkage, which is defined further herein.

A nucleotide may be a naturally-occurring nucleotide or a modified nucleotide. A naturally-occurring nucleotide has a naturally-occurring nucleoside (e.g., adenosine, guanosine, cytidine, 5-methyluridine, or uridine) covalently linked to a phosphate at the 5' carbon of the sugar. A modified nucleotide refers to a nucleotide having at least one change that is structurally distinguishable from a naturally-occurring nucleotide. A modified nucleotide may include a modified nucleobase and/or a modified sugar. Examples of modified nucleobases and modified sugars are described in detail further herein.

As used herein, the term "modified nucleobase" refers to a nucleobase having at least one change from a naturally-occurring nucleobase (e.g., adenine, guanine, cytosine, thymine, or uracil).

As used herein, the term "modified sugar" refers to a sugar having at least one change from a naturally-occurring sugar (e.g., 2'-deoxyribose in DNA or ribose in RNA). In some embodiments, a modified sugar is a pentofuranosyl sugar. In some embodiments, a modified sugar is a locked sugar. In some embodiments, a modified sugar is an unlocked sugar.

As used here, the term "internucleoside linkage" refers to the backbone linkage of the oligonucleotide that connects the neighboring nucleosides. An internucleoside linkage may be a naturally-occurring internucleoside linkage (e.g., a phosphate linkage, also referred to as a 3' to 5' phosphodiester linkage) or a modified internucleoside linkage. As used herein, the term "modified internucleoside linkage" refers to an internucleoside linkage having at least one change from a naturally-occurring internucleoside linkage. Examples of modified internucleoside linkages include, but are not limited to, a phosphorothioate linkage, a phosphorodithioate linkage, a phosphoramidate linkage, a phosphorodiamidate linkage, a thiophosphoramidate linkage, a thiophosphorodiamidate linkage, a phosphoramidate morpholino linkage, and a thiophosphoramidate morpholino linkage, and a thiophosphorodiamidate morpholino linkage, which are known in the art and described in, e.g., Bennett and Swayze, *Annu Rev Pharmacol Toxicol.* 50:259-293, 2010.

As used herein, the term "phosphorothioate linkage" refers to a 3' to 5' phosphodiester linkage that has a sulfur atom for a non-bridging oxygen in the phosphate backbone of an oligonucleotide.

As used herein, the term "phosphorodithioate linkage" refers to a 3' to 5' phosphodiester linkage that has two sulfur atoms for non-bridging oxygens in the phosphate backbone of an oligonucleotide.

As used herein, the term "thiophosphoramidate linkage" refers to a 3' to 5' phospho-linkage that has a sulfur atom for a non-bridging oxygen and a NH group as the 3'-bridging oxygen in the phosphate backbone of an oligonucleotide.

As used herein, the term "bicyclic sugar" refers to a modified pentofuranosyl sugar containing two fused rings. For example, a bicyclic sugar may have the 2' ring carbon of the pentofuranose linked to the 4' ring carbon by way of one or more carbons (e.g., a methylene) and/or heteroatoms (e.g., sulfur, oxygen, or nitrogen). An example of a bicyclic sugar is a locked sugar.

As used herein, the term "locked sugar" refers to a pentofuranosyl sugar in which the 2'-oxygen is linked to the 4' ring carbon by way of a carbon (e.g., a methylene) or a heteroatom (e.g., sulfur, oxygen, or nitrogen). In some embodiments, a locked sugar has the 2'-oxygen linked to the 4' ring carbon by way of a carbon (e.g., a methylene). A nucleoside having a locked sugar is referred to as a locked nucleoside.

As used herein, the term "unlocked sugar" refers to an acyclic sugar that has a 2',3'-seco acyclic structure, where the bond between the 2' carbon and the 3' carbon in a pentofuranosyl ring is absent.

As used herein, the term "polynucleotide" refers to an oligonucleotide, or nucleotide, and fragments or portions thereof, and to DNA or RNA of genomic or synthetic origin, which may be single- or double-stranded, and represent the sense or antisense strand. A single polynucleotide is translated into a single polypeptide.

As used herein, the term "substantial identity" or "substantially identical," used in the context of nucleic acids or polypeptides, refers to a sequence that has at least 50% sequence identity with a reference sequence. Alternatively, percent identity can be any integer from 50% to 100%. In some embodiments, a sequence is substantially identical to a reference sequence if the sequence has at least 50%, 55%, 60%, 65%, 70%, 75%, 80%, 85%, 90%, 91%, 92%, 93%, 94%, 95%, 96%, 97%, 98%, or 99% sequence identity to the reference sequence as determined using, e.g., BLAST.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A comparison window includes reference to a segment of any one of the number of contiguous positions, e.g., a segment of at least 10 residues. In some embodiments, the comparison window has from 10 to 600 residues, e.g., about 10 to about 30 residues, about 10 to about 20 residues, about 50 to about 200 residues, or about 100 to about 150 residues, in which a sequence may be compared to a reference sequence of the same number of contiguous positions after the two sequences are optimally aligned.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference sequence if the smallest sum probability in a comparison of the test amino acid sequence to the reference amino acid sequence is less than about 0.01, more preferably less than about $10^{-5}$, and most preferably less than about $10^{-20}$.

BRIEF DESCRIPTION OF THE DRAWINGS

FIG. 4A is a bar graph showing the results of an experiment where on day 3 of differentiation, human MDMs were transfected with siRNAs targeting GAPLINC (or negative control siRNAs). After 7 days, qPCR was used to measure GAPLINC expression. FIG. 4B is a volcano plot of the results of RNA-sequencing and differential expression analysis using DESEQ2. The plot summarizes genes that are up or down regulated when GAPLINC is knocked down. FIG. 4C is a bar graph of Go Term analysis performed using DAVID on the genes from FIG. 4B. The top category for upregulated genes was the immune response genes, specifically IFN genes.

FIG. 9A illustrates the guide RNA targeting scheme used to create GAPLINC knockout mice (also referred to as GAPLINC−/−). FIG. 9B summarizes the results of qPCR on WT and GAPLINC−/− (also referred to as GAP KO, GAP KO, and GAPLINC-KO) BMDMs confirming the removal of Exon 1. Since Exon 2 is present there is a detectable PCR product made using Exon 2 specific primers. FIG. 9C is a volcano plot of the genes altered in the GAPLINC−/− BMDM's. All in grey are expressed at least two-fold higher than the same gene in WT. FIG. 9D is a plot of Go Term analysis performed on the upregulated genes from the plot in FIG. 9C using Panther. The top category for upregulated genes in GAPLINC-KO was inflammation-related genes.

10B) via intraperitoneal route and monitored at the indicated time points. Mice were sacrificed at the conclusion of the experiment.

Figure 11:
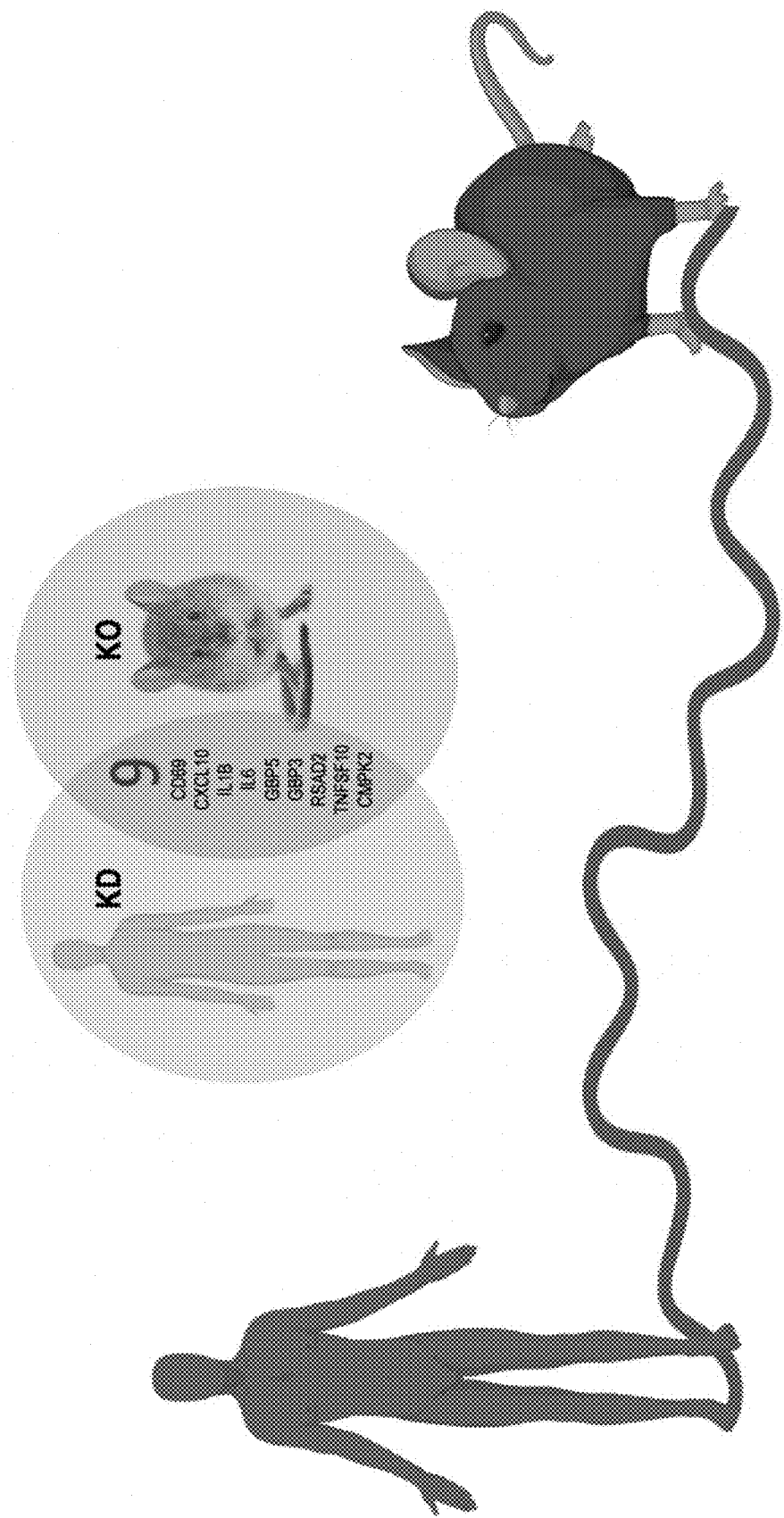

FIG. 11 is a diagram showing that disruption of GAPLINC in both human (knockdown) or mouse (knockout) results in nine inflammatory related genes that are upregulated in both species.

Figure 12A:
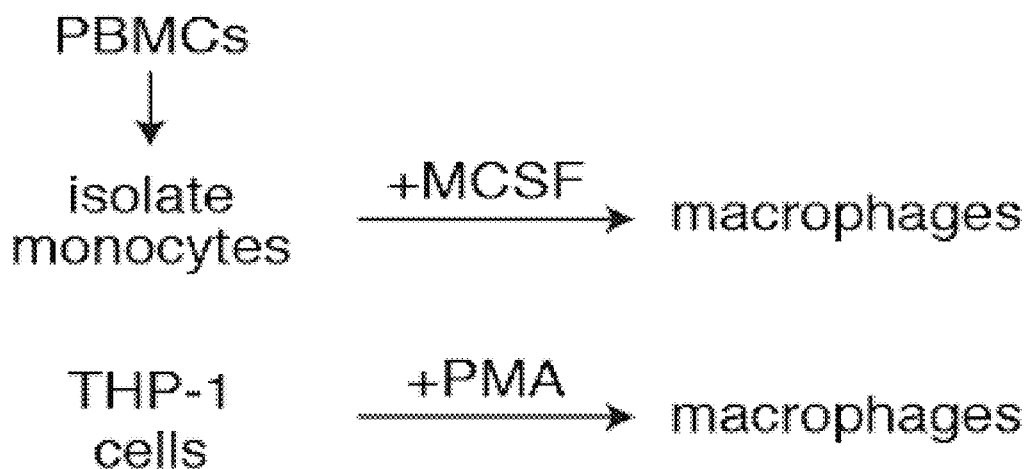
Figure 12B:
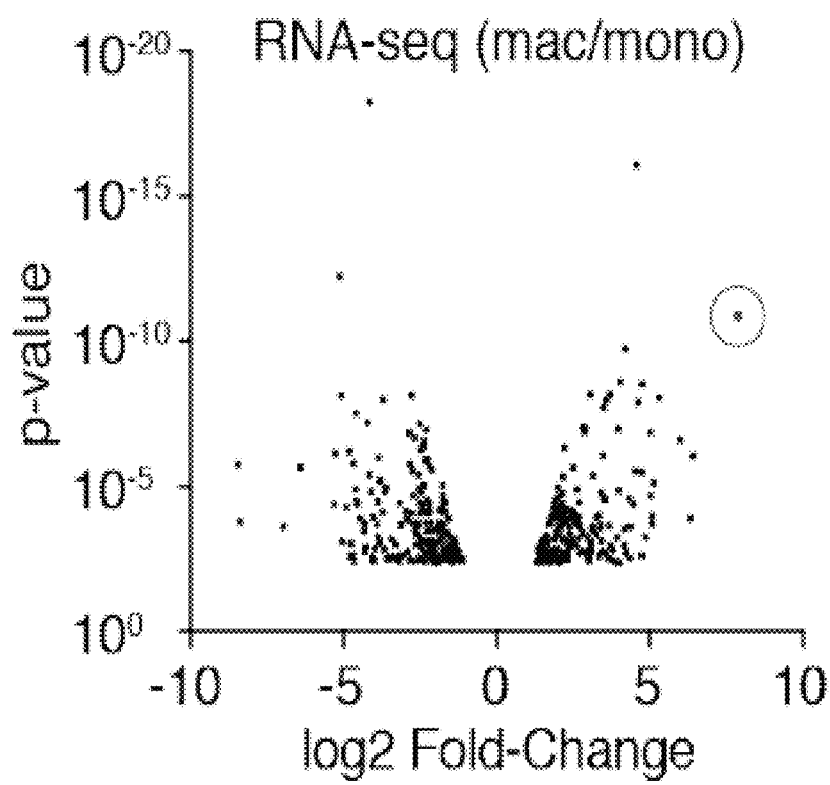
Figure 12C:
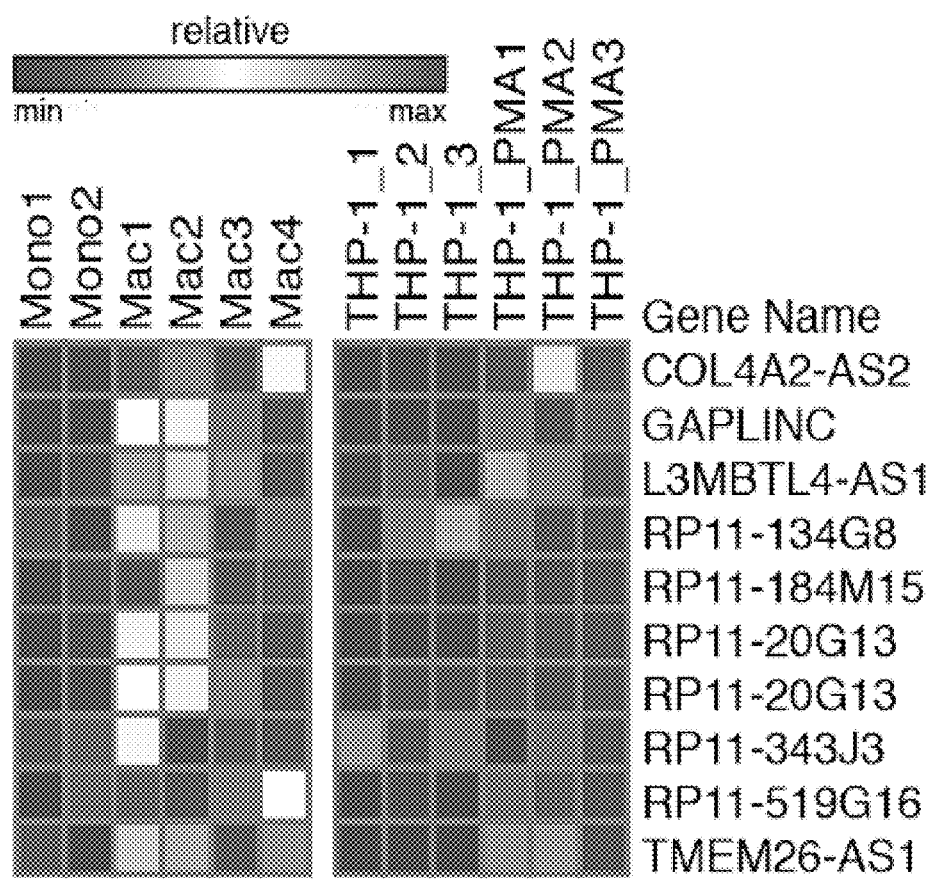
Figure 12D:
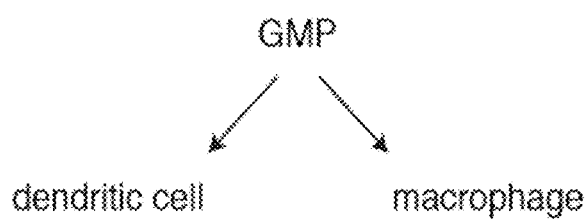
Figure 12D:
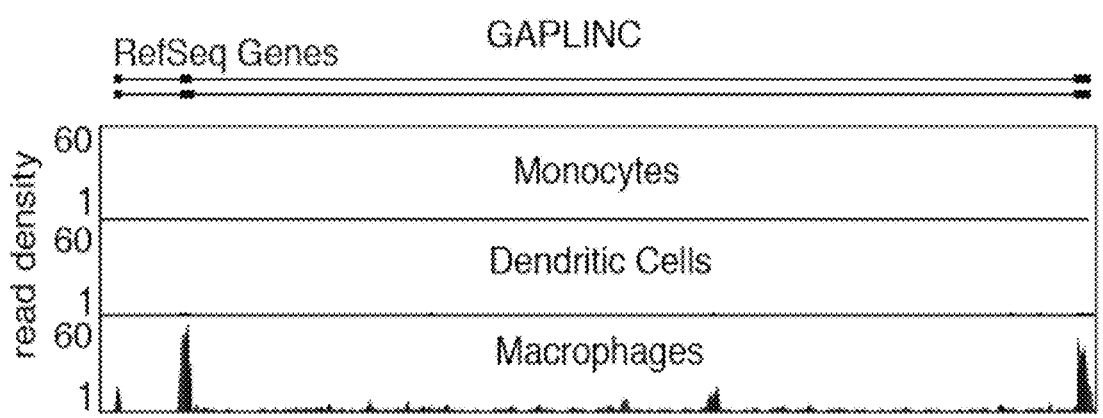
Figure 12E:
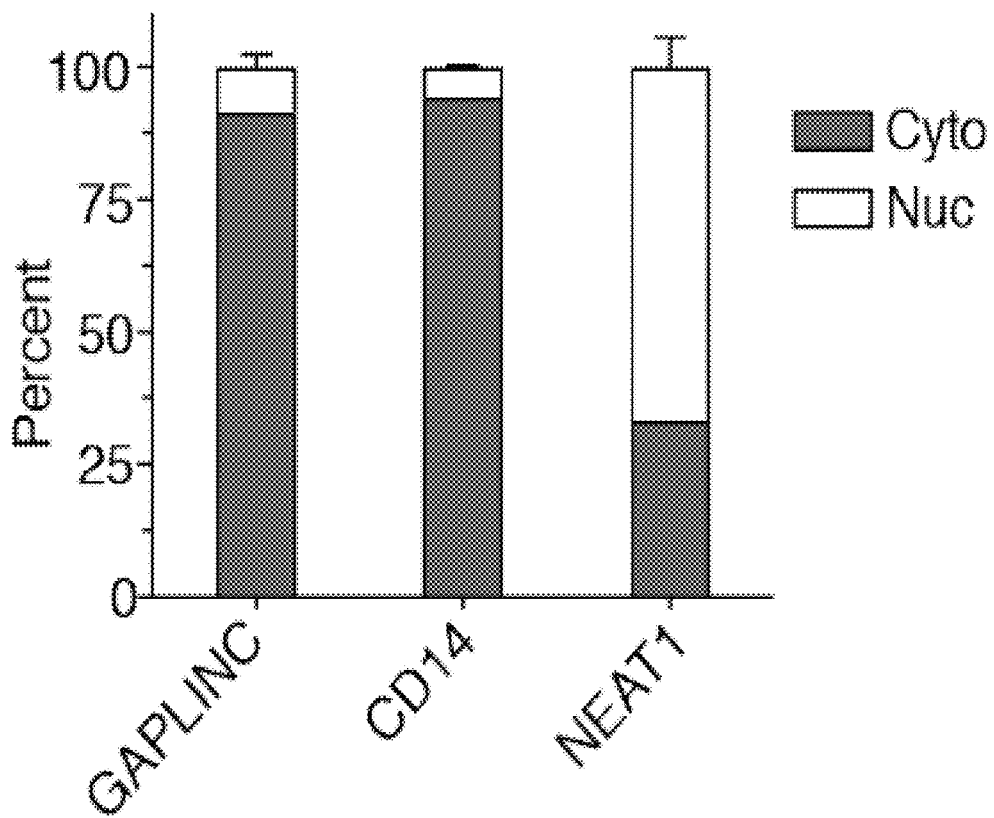
Figure 12F:
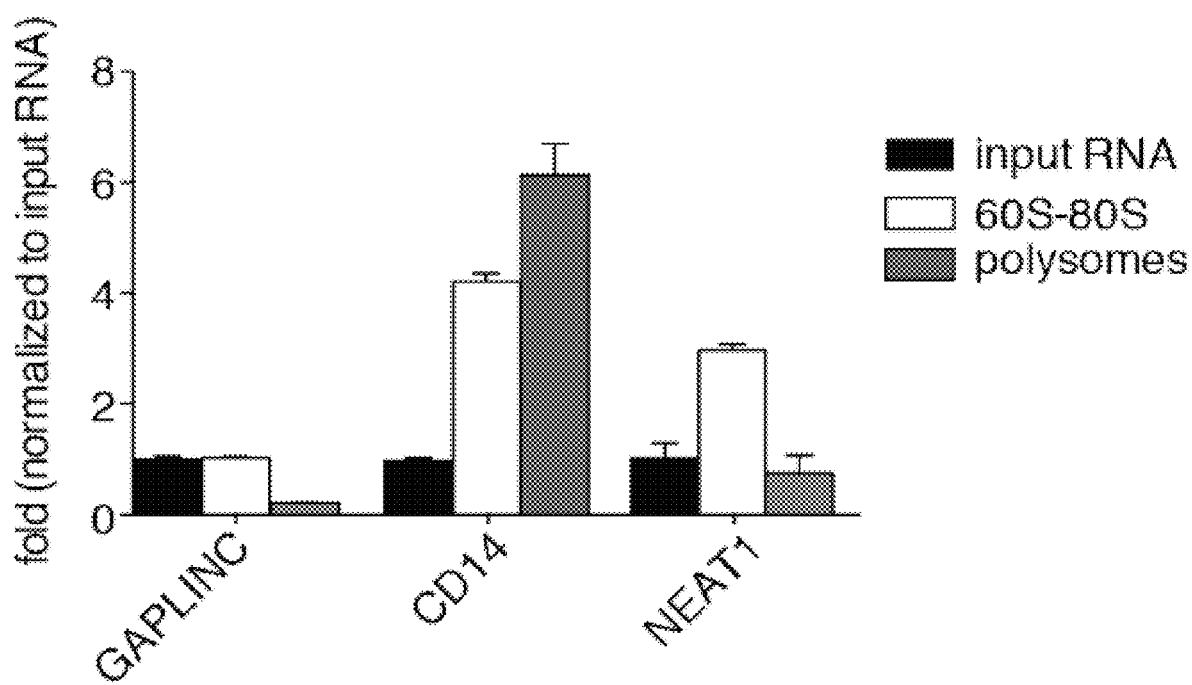

FIGS. 12A-12F show identification and characterization of macrophage-specific lncRNA GAPLINC. FIG. 12A: Schematic for macrophage differentiation in vitro using primary human cells or immortalized THP-1 cells. Isolated monocytes from human peripheral blood mononuclear cells (PBMCs) are differentiated into macrophages using recombinant macrophage colony stimulating factor (MCSF). THP-1 cells are differentiated into macrophages by treatment with phorbol 12-myristate 13-acetate (PMA) (100 nM). FIG. 12B: RNA-seq analysis on macrophages differentiated from monocytes isolated from human PBMCs (n=4 donors). Results are represented in a Volcano plot. GAPLINC (shown in red) is the most upregulated lncRNA (>1000-fold). FIG. 12C: Heatmap represents gene expression from a custom Nanostring panel which shows the top ten differentially expressed lncRNA comparing monocytes to macrophages in primary human cells and THP-1 cells. Data from Nanostring performed in biological duplicates. FIG. 12D: Schematic for granulocyte-monocyte progenitor (GMP) cells that give rise to two distinct populations, 1) monocyte-derived dendritic cells (MDDCs), and 2) monocyte-derived macrophage cells (MDMs). UCSC genome browser track displays RNA-seq reads from monocytes, macrophages, and dendritic cells at the GAPLINC locus. FIG. 12E: qPCR analysis of RNAs purified from nuclear (white) and cytoplasmic (gray) fractions in MDMs. FIG. 12F: qPCR analysis of RNAs isolated from different polysome fractions of MDM lysates.

Figure 13A:
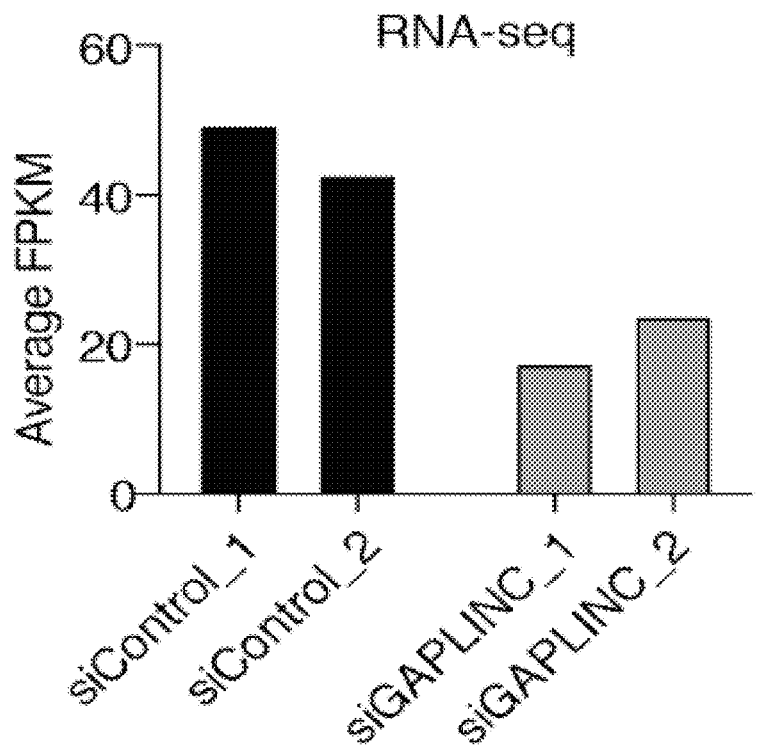
Figure 13B:
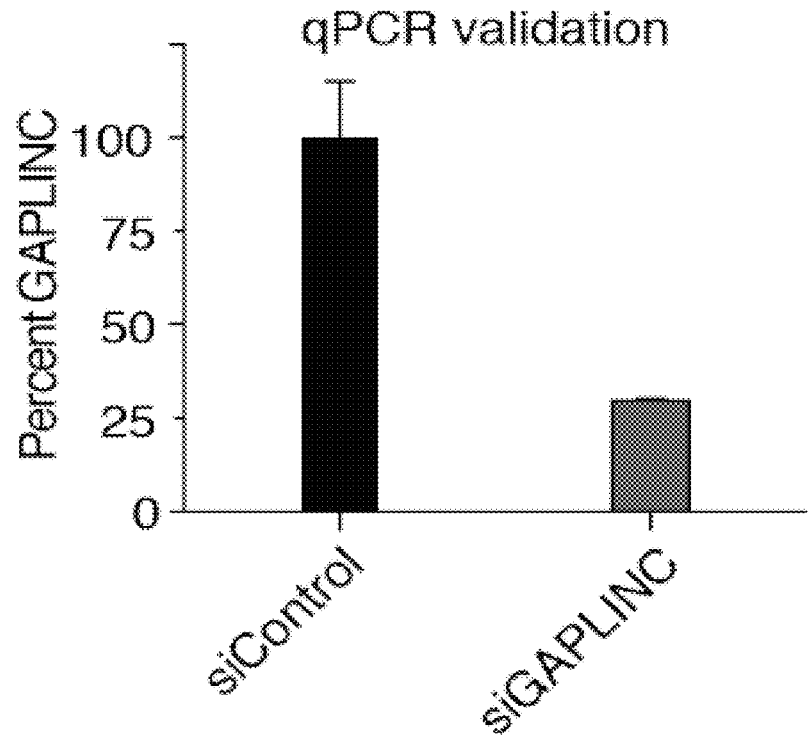

FIGS. 13A and 13B show efficiency of GAPLINC knockdown. Monocytes isolated from human PBMCs and differentiated for two days were transfected with control or GAPLINC siRNA. Transfection was allowed to proceed for 72 h. RNA-seq analysis of GAPLINC levels were quantified using FPKM values (FIG. 13A). RNA-seq was performed in biological duplicates. qPCR analysis of GAPLINC was performed to validate knockdown (FIG. 13B); qPCR data from one independent experiment.

Figure 14A:
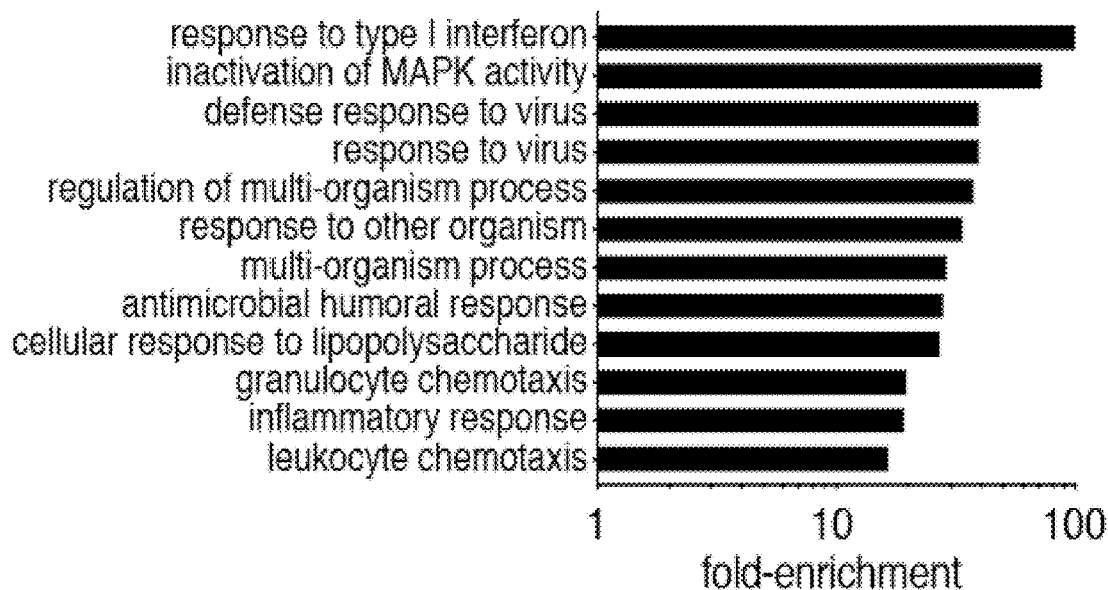
Figure 14B:
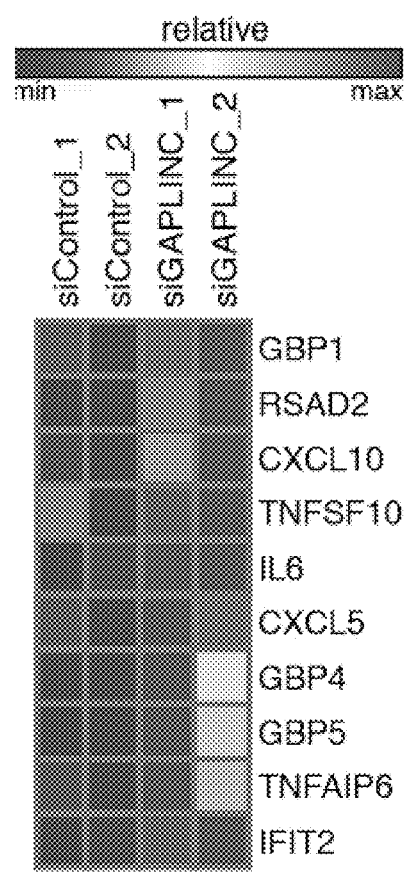
Figures 14C, 14D:
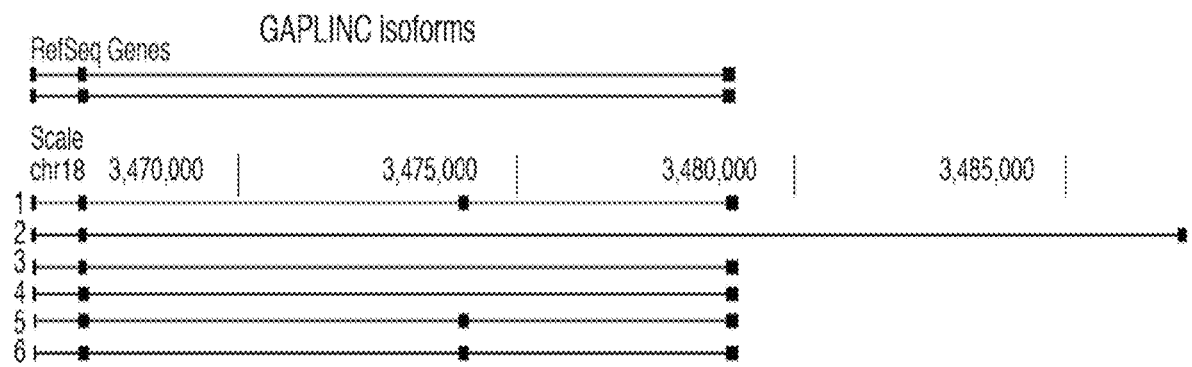
Figure 14E:
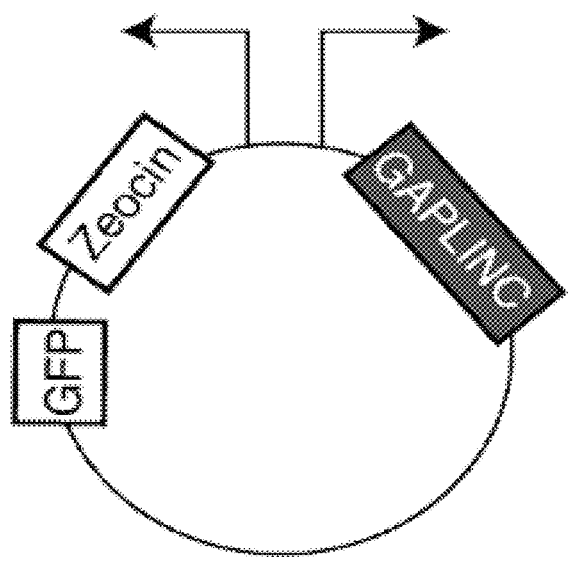
Figure 14F:
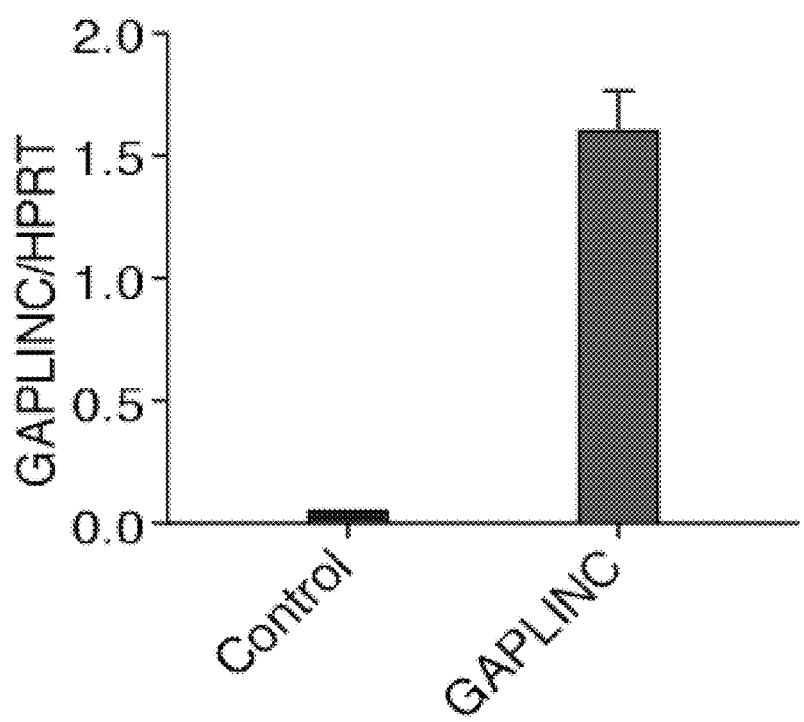
Figure 14G:
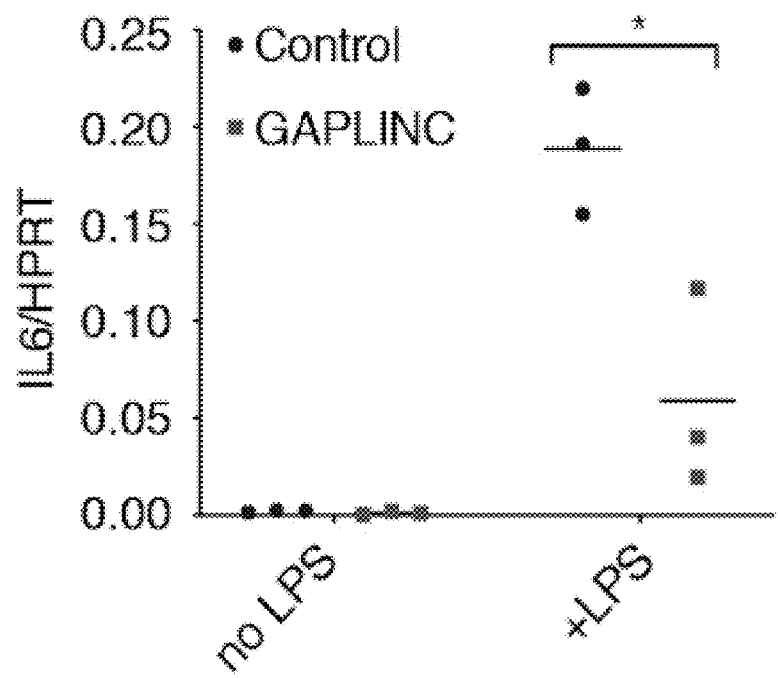
Figure 14H:
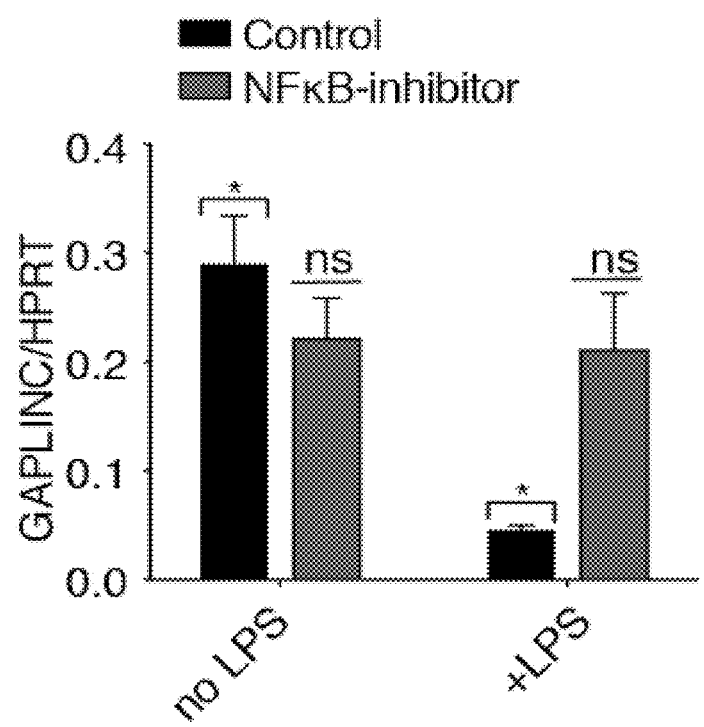
Figure 14I:
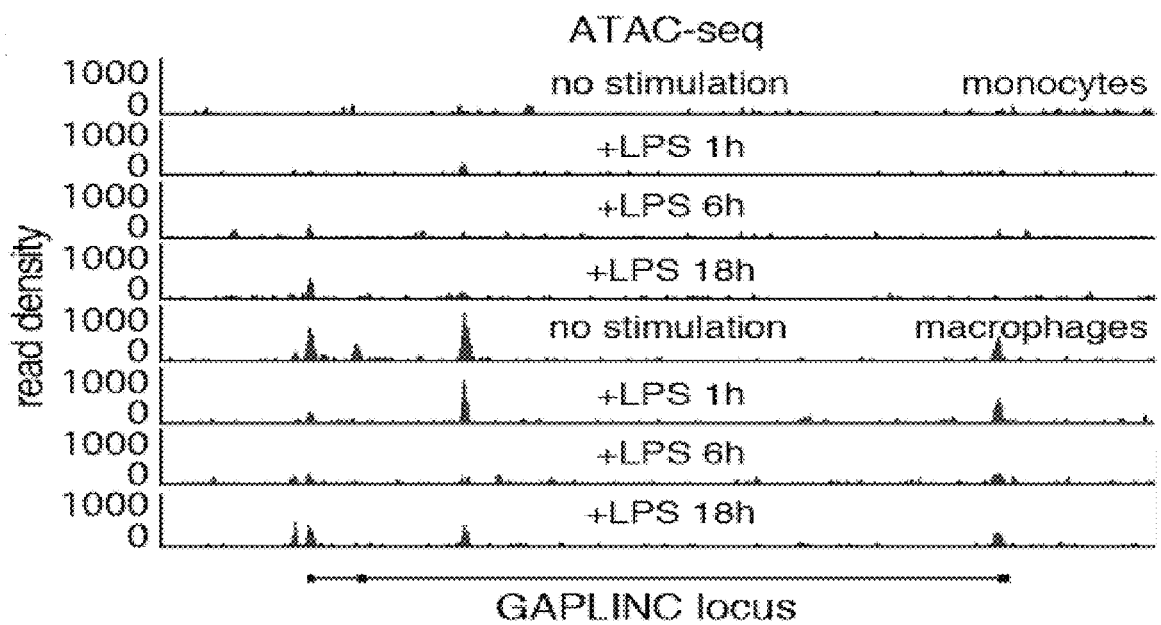

FIGS. 14A-14I show monocytes isolated from human PBMCs and differentiated into macrophages were transfected with control or GAPLINC siRNA. FIG. 14A: GO-Term analysis on significantly upregulated genes. FIG. 14B: Heat map represents gene expression of top immune-related genes upregulated upon GAPLINC knockdown. Data from RNA-seq performed in biological duplicates. FIG. 14C: GAPLINC isoforms in MDMs as determined by Nanopore-based R2C2 sequencing. Data from Nanopore-sequencing performed in biological duplicates. FIG. 14D: Table representing read counts and percent of each GAPLINC isoform. FIG. 14E: Bi-directional vector expressing GFP-Zeocin on one side and GAPLINC on the other side. FIGS. 14F and 14G: qPCR analysis of GAPLINC expression in THP-1 cells expressing ectopic GAPLINC or empty-vector control. Levels of IL6 were quantified following stimulation with LPS (200 ng/ml) for 6 h; data pooled from three independent experiments. *p<0.05. FIG. 14H: qPCR analysis of GAPLINC in MDMs (n=3) pretreated with DMSO or BAY-7082 (10 uM), followed by LPS stimulation (200 ng/ml) for 6 h; data pooled from three independent experiments. *p<0.05. FIG. 14I: ATAC-seq analysis of monocytes and macrophages, untreated and treated with LPS (200 ng/ml) for 1 h, 6 h and 18 h. UCSC browser track displays ATAC-Seq reads at the GAPLINC locus.

Figure 15:
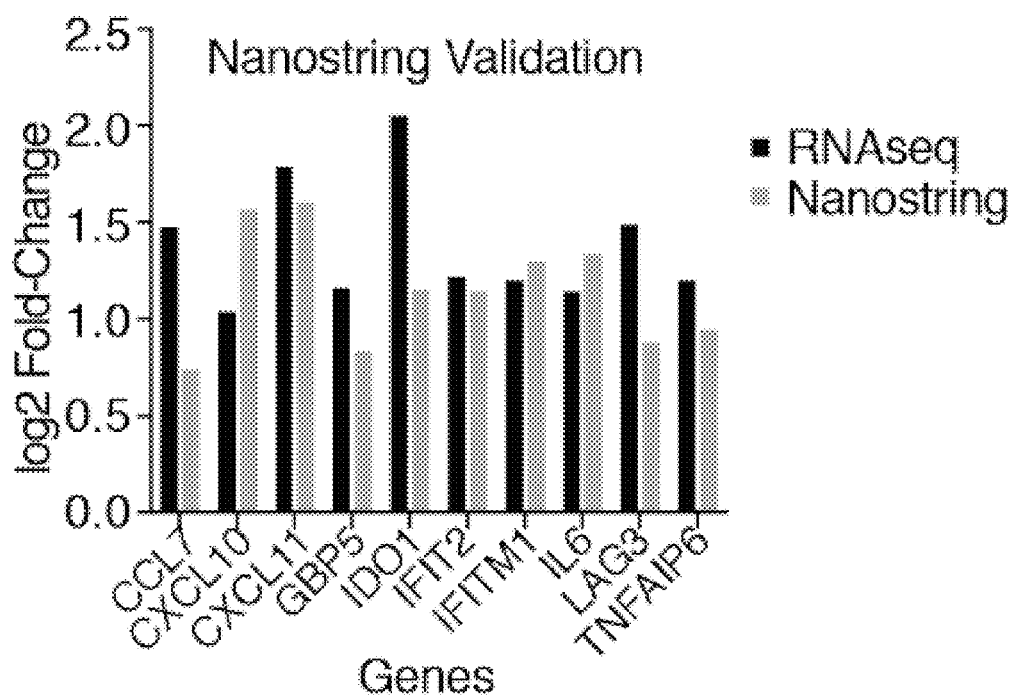

FIG. 15 shows validation of RNA-Seq data using Nanostring. Genes upregulated upon GAPLINC knockdown in MDMs were validated using a gene set from Nanostring technology. A selection of genes is shown above.

Figure 16A:
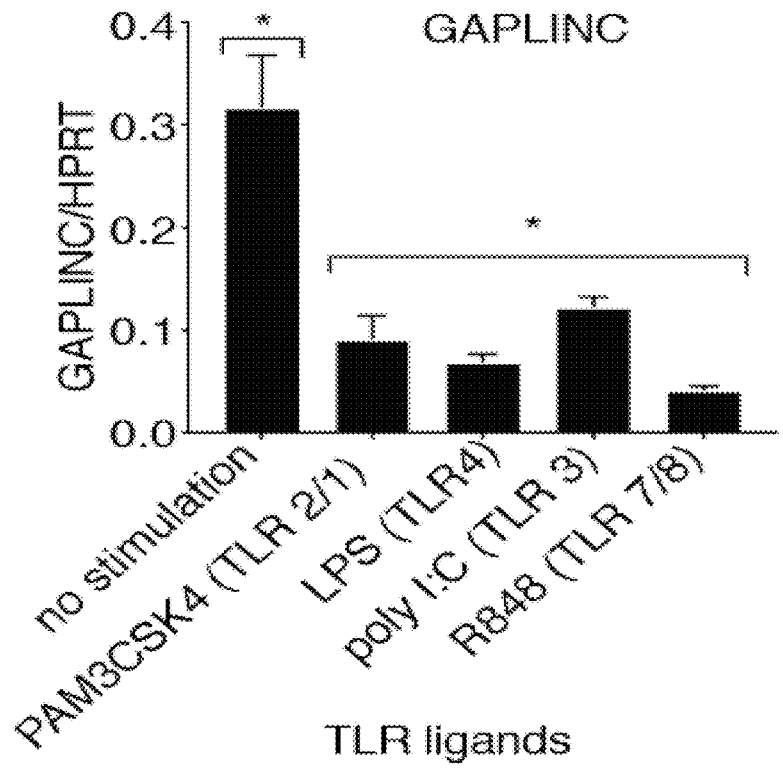
Figure 16B:
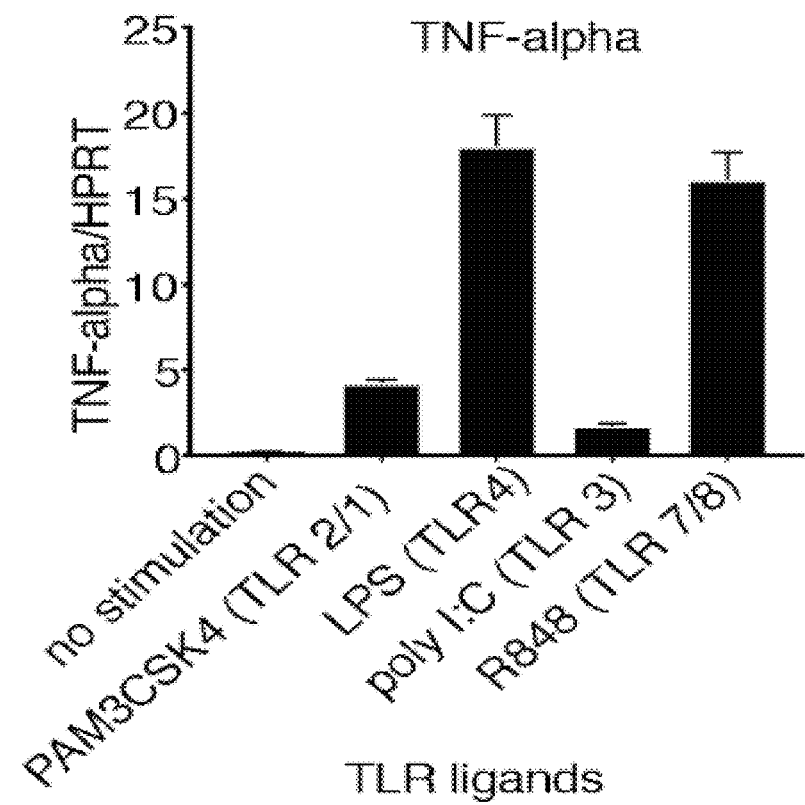
Figure 16C:
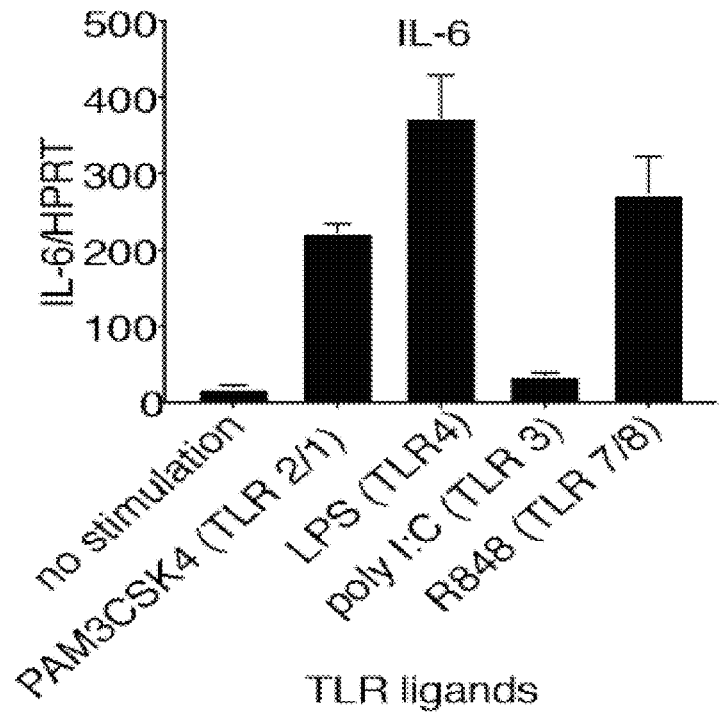
Figure 16D:
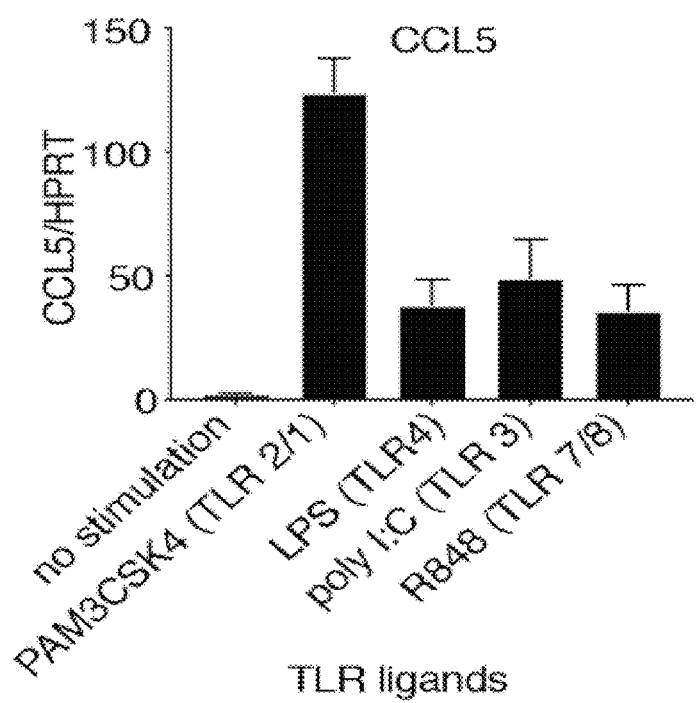
Figure 16E:
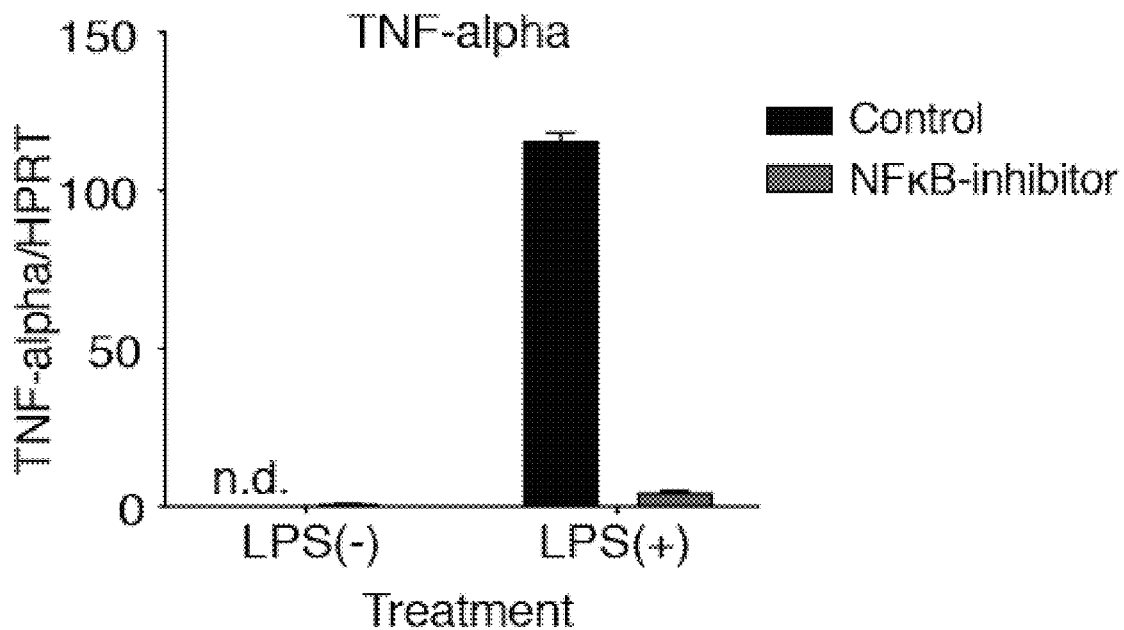
Figure 16F:
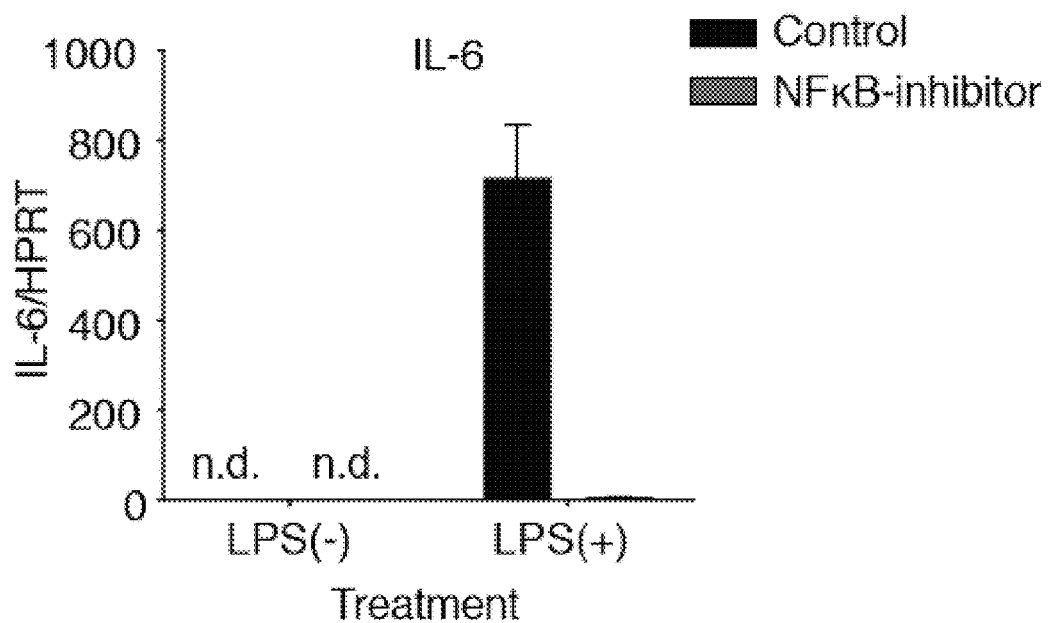

FIGS. 16A-16F show that human GAPLINC expression is reduced following TLR activation. FIG. 16A: qPCR analysis of GAPLINC expression in MDMs stimulated with a variety of TLR ligands for 6 h; data from qPCR performed in biological triplicates. *p<0.05. FIGS. 16B-16D: qPCR analysis of TNFα, IL6 and CCL5 expression in MDMs upon TLR stimulation; data (Mean±SD) are representative of three independent experiments. FIGS. 16E and 16F: qPCR analysis of TNFα and IL6 in MDMs pretreated with DMSO or BAY-7082 (10 uM), followed by LPS stimulation (200 ng/ml) for 6 h; data (Mean±SD) are representative of three independent experiments. *p<0.05; n.d., not detectable.

Figure 17A:
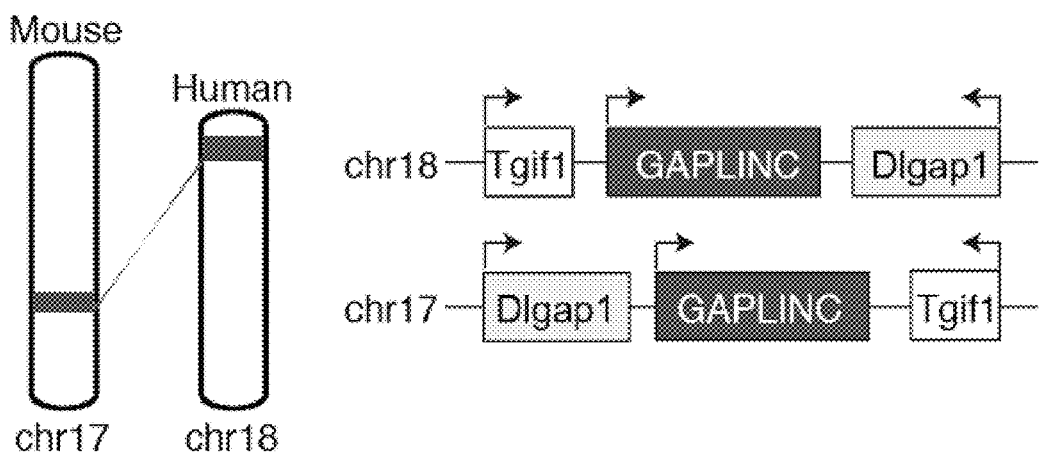
Figure 17B:
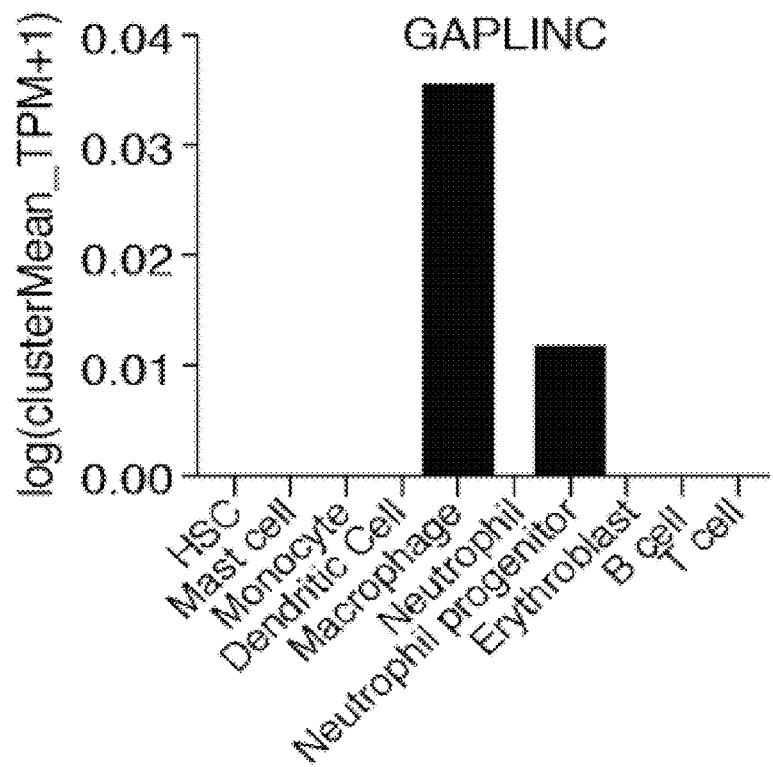
Figure 17C:
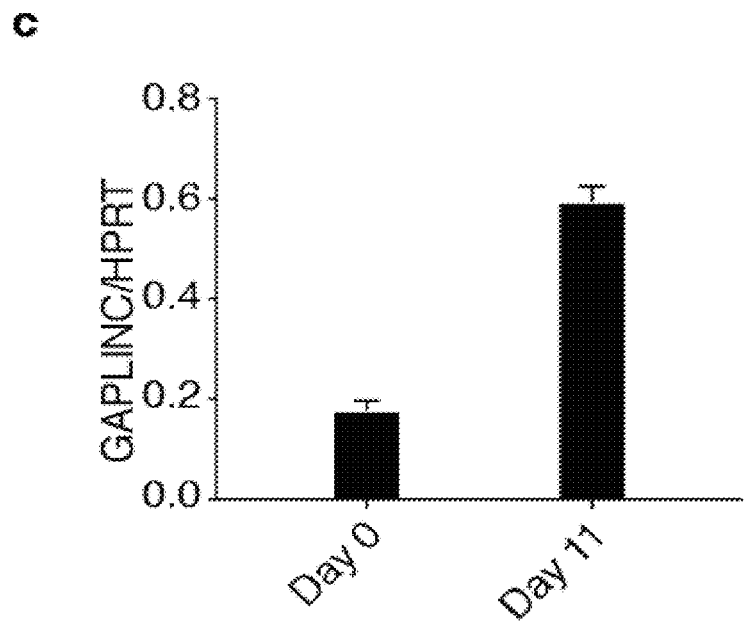
Figure 17D:
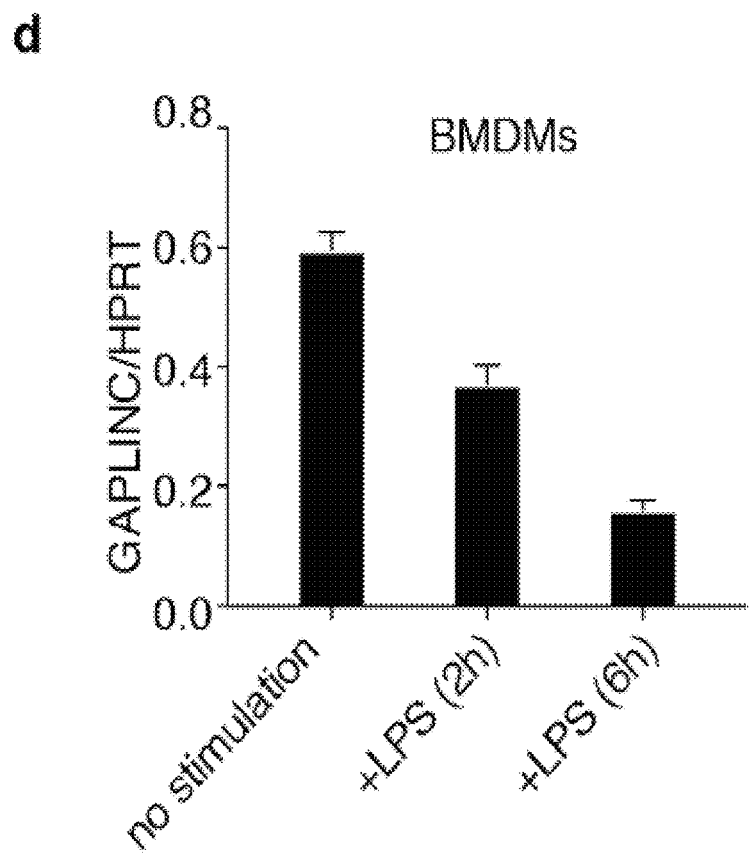
Figure 17E:
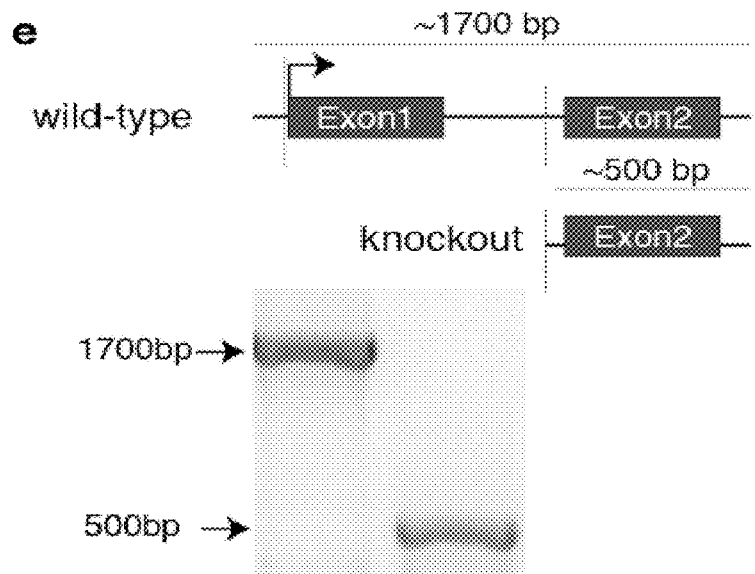
Figure 17F:
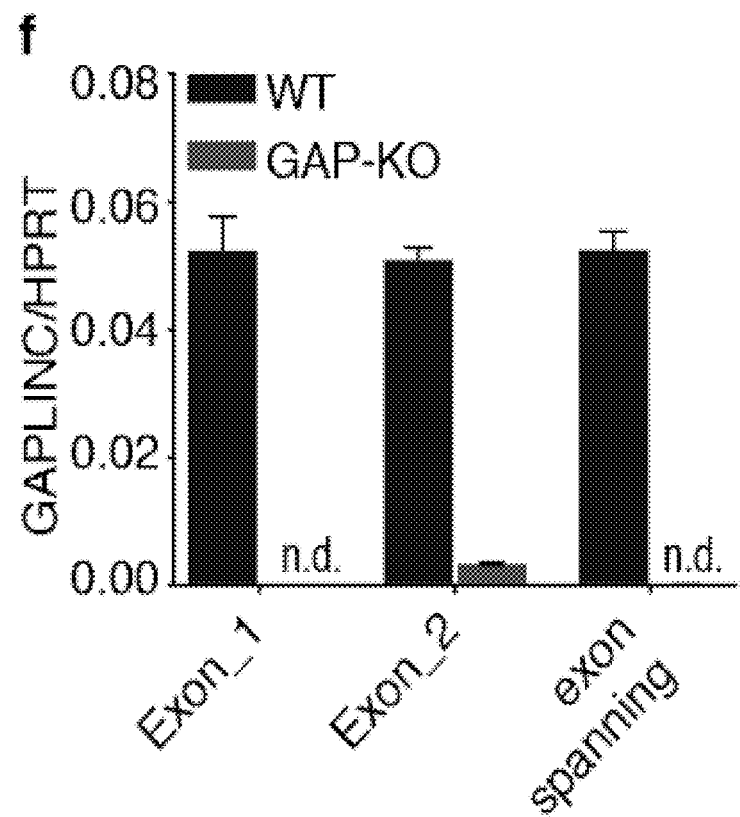
Figure 17G:
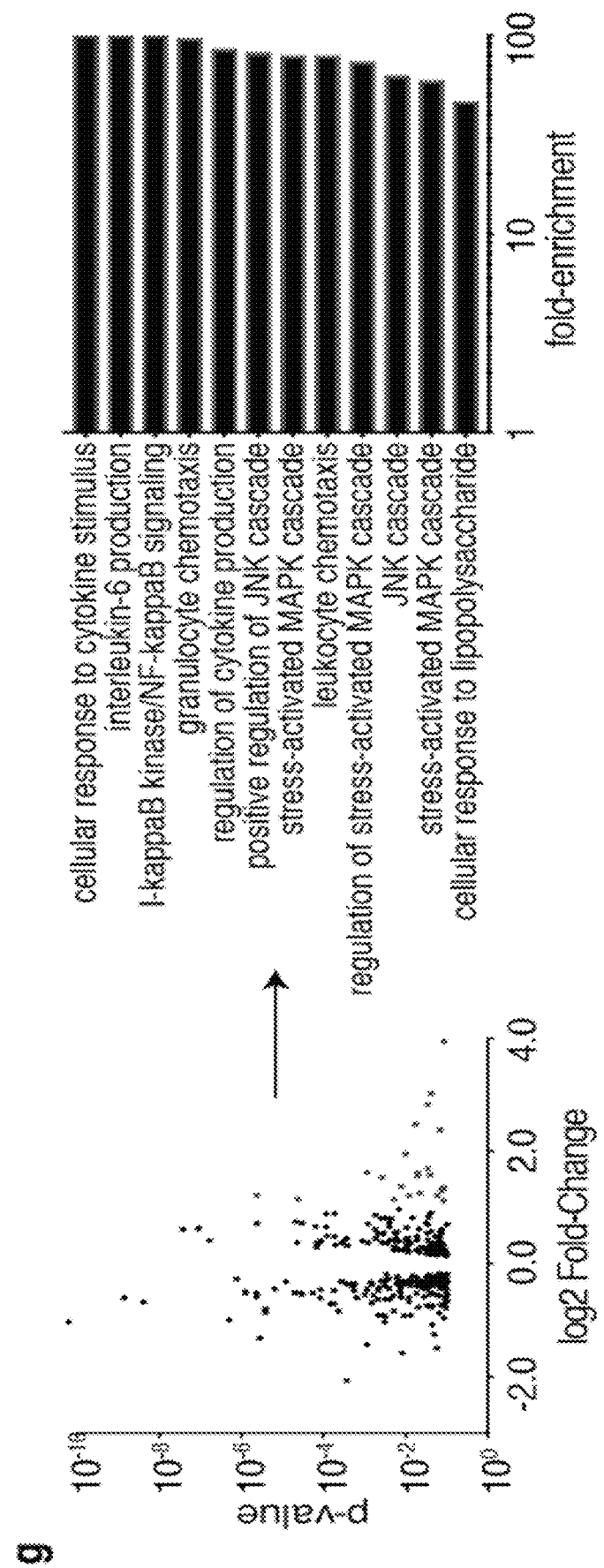
Figure 17H:
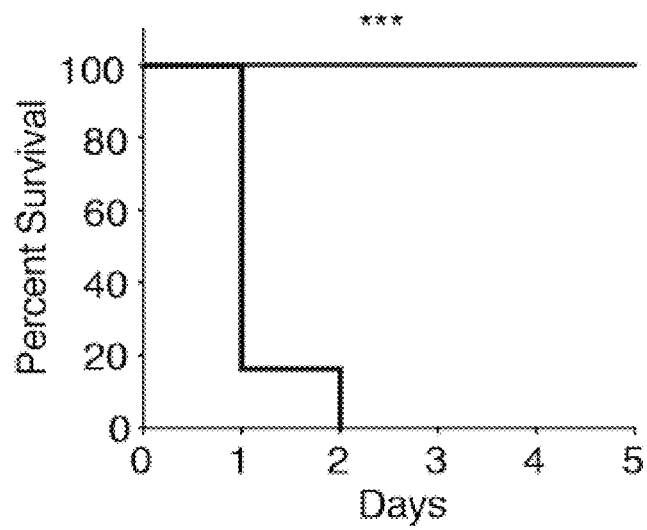
Figure 17I:
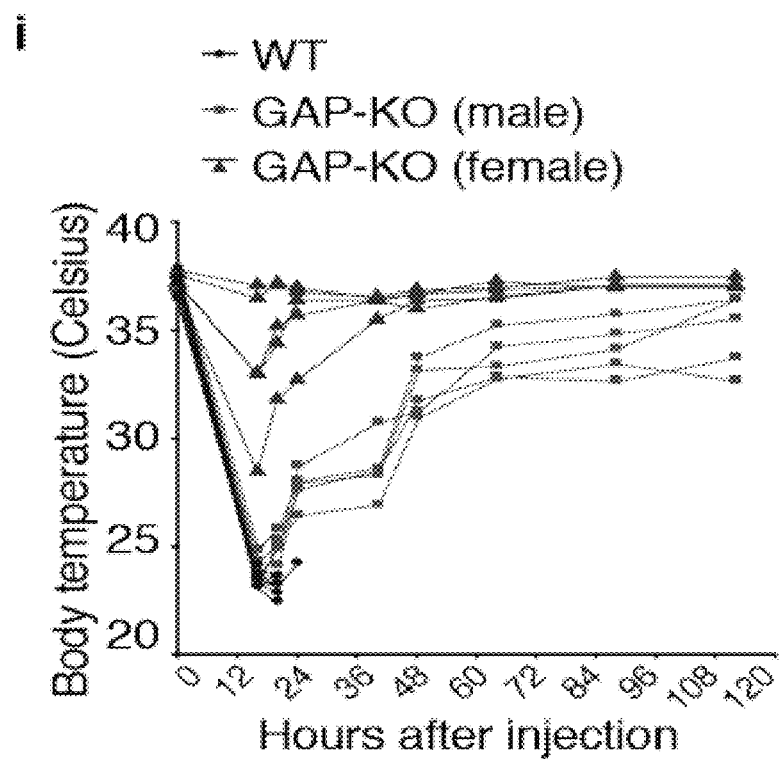

FIGS. 17A-17I show that GAPLINC is conserved in mice and regulates response to endotoxic shock. FIG. 17A: GAPLINC is conserved in synteny. GAPLINC is located on Chr18 in humans and on Chr17 in mice between protein-coding genes, Dlgap1 and Tgif1. Dlgap1 is not expressed in macrophages. FIG. 17B: Mouse cell atlas (MCA) shows distribution of Gaplinc levels in various immune cell types (bone marrow). FIG. 17C: qPCR analysis of Gaplinc expression in bone marrow (BM) cells and BMDMs; these data (Mean±SD) are representative of three independent experiments. FIG. 17D: qPCR analysis of Gaplinc expression in BMDMs stimulated with LPS (200 ng/ml) for 6 h; these data (Mean±SD) are representative of three independent experiments. FIG. 17E: Schematic of Gaplinc locus before and after CRISPR/Cas9 mediated deletion. Dashed lines indicate the approximate region of deletion. Gel represents PCR amplification of genomic data. Amplicon lengths are compared for WT and Gaplinc-KO mice. FIG. 17F: qPCR analysis of Gaplinc expression in WT and GAPLINC-KO BMDMs using a combination of primers to detect Exon1, Exon2 and exon-spanning regions of the Gaplinc transcript; these data (Mean±SD) are representative of three independent experiments. FIG. 17G: RNA-seq analysis in BMDMs from WT and Gaplinc-KO mice (n=3). Results are represented in a Volcano plot. Significantly upregulated genes with a fold-change ≥2 are shown in red. GO-Term analysis was performed on significantly upregulated genes. FIG. 17H: Survival data of WT and Gaplinc KO mice are shown in response to E. coli LPS challenge (5 mg/kg/mice) (n=6-10). The statistical test of differences was calculated using the Log-rank (Mantel-Cox) test. ***p<0.001. FIG. 17I: Changes in body temperature of WT and Gaplinc KO mice were recorded at the indicated time points.

Figure 18A:
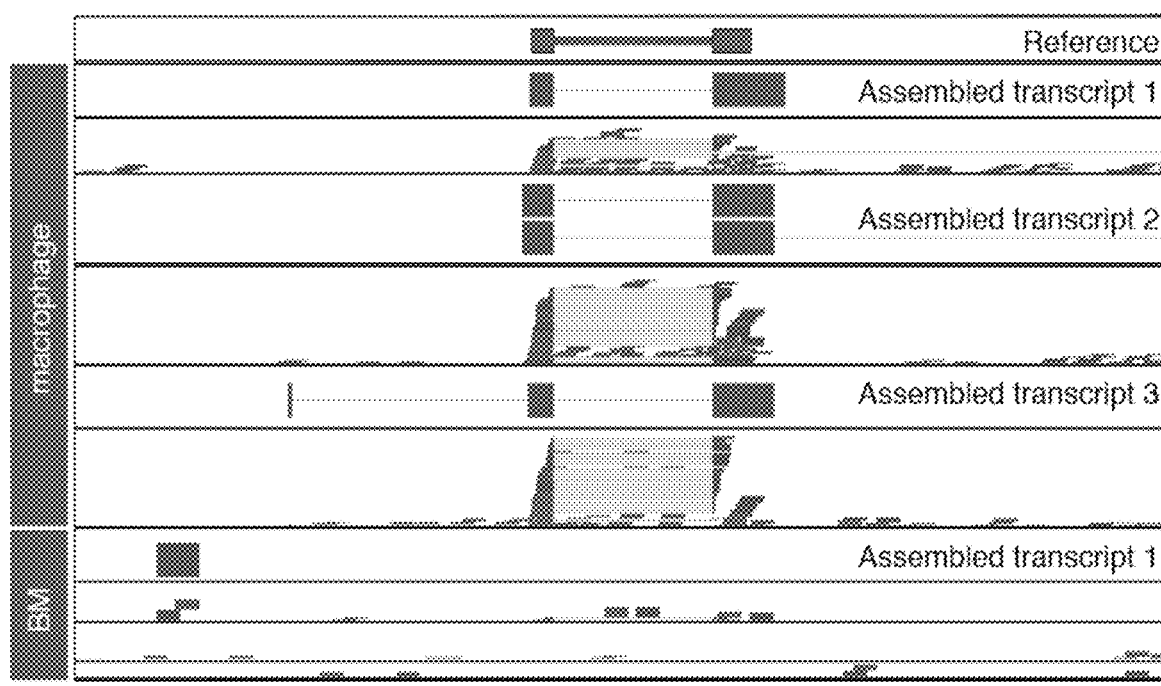
Figure 18B:
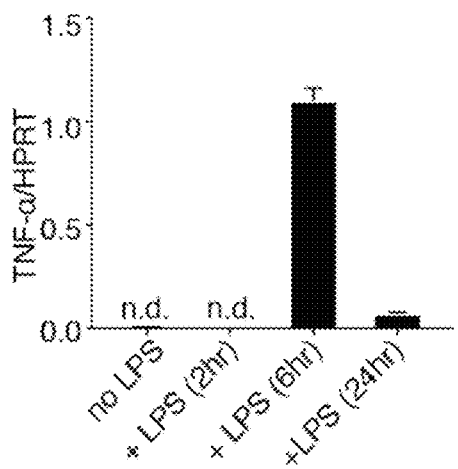
Figure 18B:
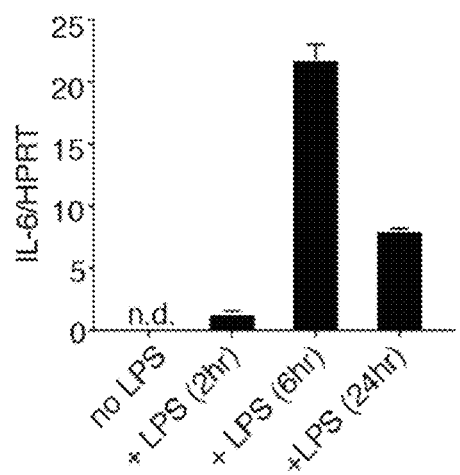
Figure 18C:
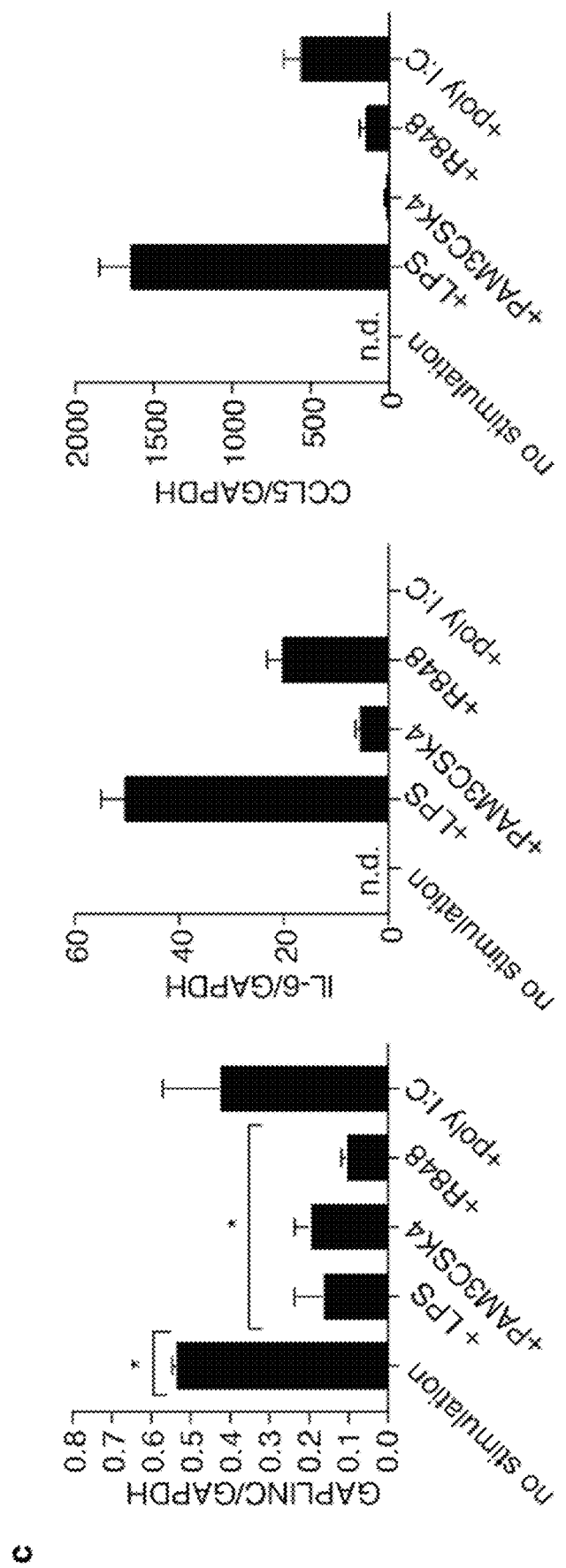

FIGS. 18A-18C show that mouse Gaplinc is macrophage-specific and its expression is reduced following TLR activation. FIG. 18A: RNA-seq analysis in bone marrow cells and BMDMs. UCSC browser track displays de-novo transcript assembly of raw sequencing reads at the Gaplinc locus. FIG. 18B: qPCR analysis of Tnfα and Il6 expression in BMDMs upon LPS stimulation at the indicated time points; data (Mean±SD) are representative of three independent experiments. FIG. 18C: qPCR analysis of Gaplinc in BMDMs upon TLR stimulation; data from qPCR performed in biological triplicates. qPCR analysis of Il6 and Ccl5 expression in BMDMs upon TLR stimulation; data (Mean±SD) are representative of three independent experiments. *p<0.05; n.d., not detectable.

Figure 19:
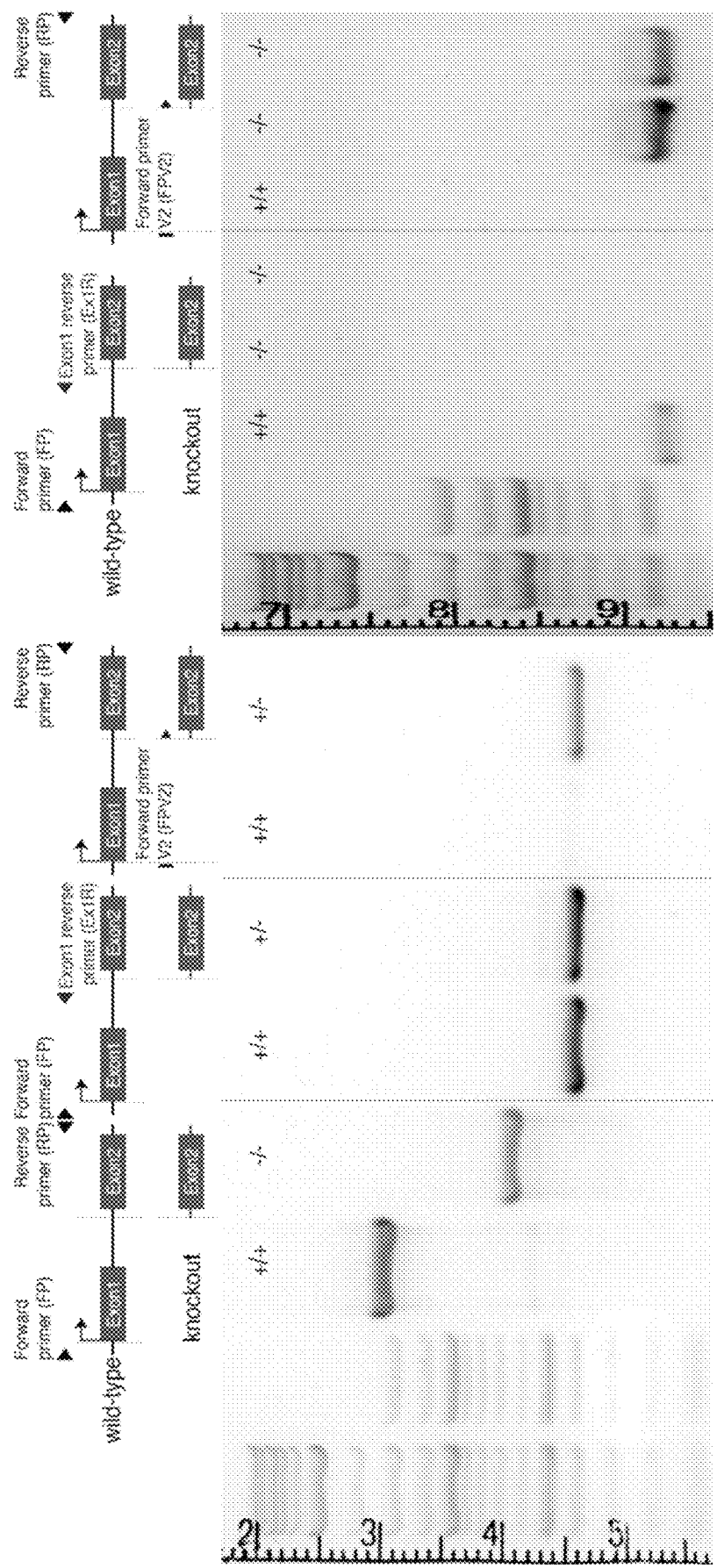

FIG. 19 shows genotyping strategy to confirm Gaplinc knockout. Gel represents PCR amplification of genomic data. Amplicon lengths are compared for WT (+/+), heterozygous Gaplinc-KO (+/−) and homozygous GAPLINC-KO (−/−) mice. FP and RP primers generate an amplicon approximately 1700 bp in length in WT and approximately 500 bp in length in Gaplinc-KO mice. FP and Ex1R primers generate an amplicon product in WT mice, but no product in Gaplinc-KO mice (Exon 1 is deleted). FPV2 is designed to the actual cut site and includes sequences from the promoter and intronic region. FPV2 and RP generate an amplicon product in Gaplinc-KO mice and no product in WT mice (no primer binding sequence for FPV2).

Figure 20A:
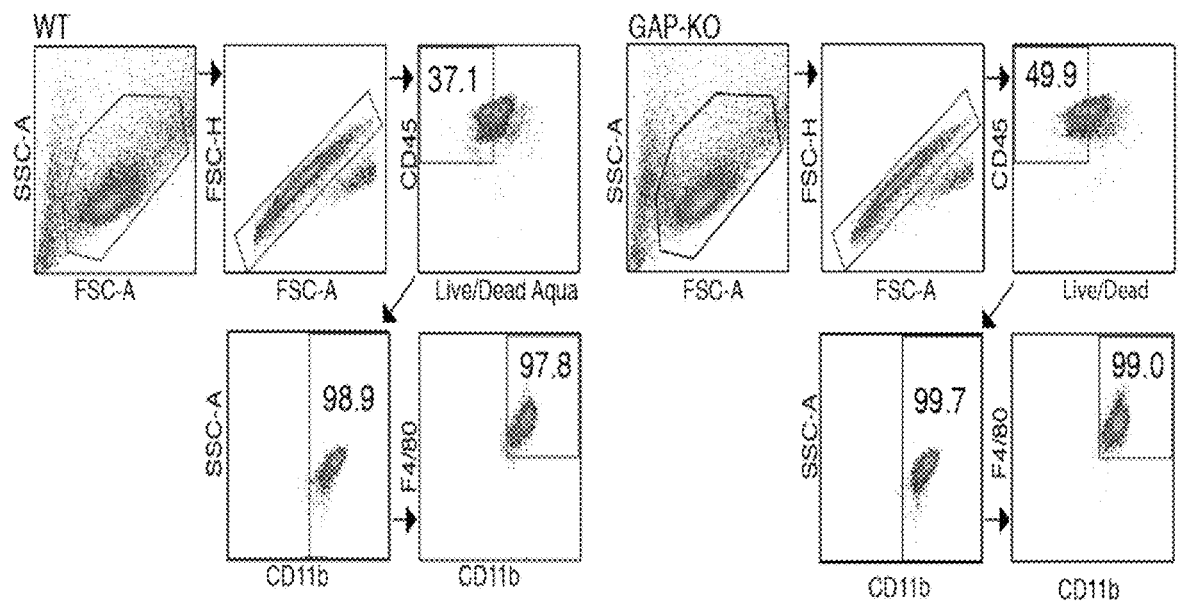
Figure 20B:
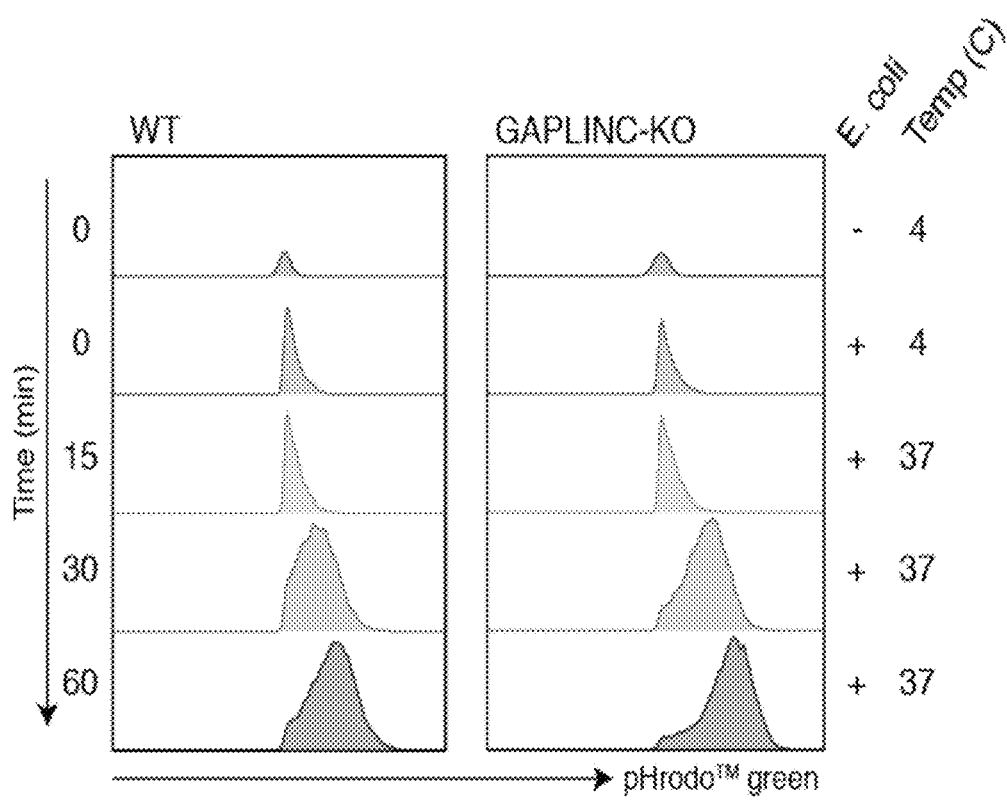

FIGS. 20A and 20B show that Gaplinc knockout does not affect macrophage differentiation or function, or expression of neighboring genes. FIG. 20A: F4/80 and CD11b expression in BMDMs from WT and Gaplinc-KO mice. FIG. 20B: pHrodo green E. coli bioparticles were incubated with WT and Gaplinc-KO BMDMs at the indicated temperatures and time points.

Figure 21:
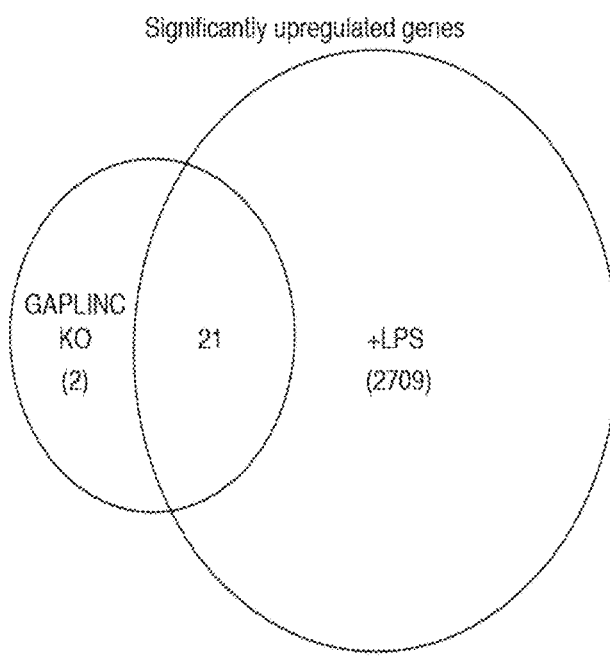

FIG. 21 shows that genes upregulated in Gaplinc knockout overlap with LPS-stimulated genes in WT. RNA-seq analysis in WT and Gaplinc-KO BMDMs. Table displays significantly upregulated genes (*$p<0.05$) upon Gaplinc-KO with fold-change ≥2. Venn diagram shows an overlap of genes upregulated in knockout and genes upregulated upon LPS stimulation (200 ng/ml, 6 h).

Figure 22A:
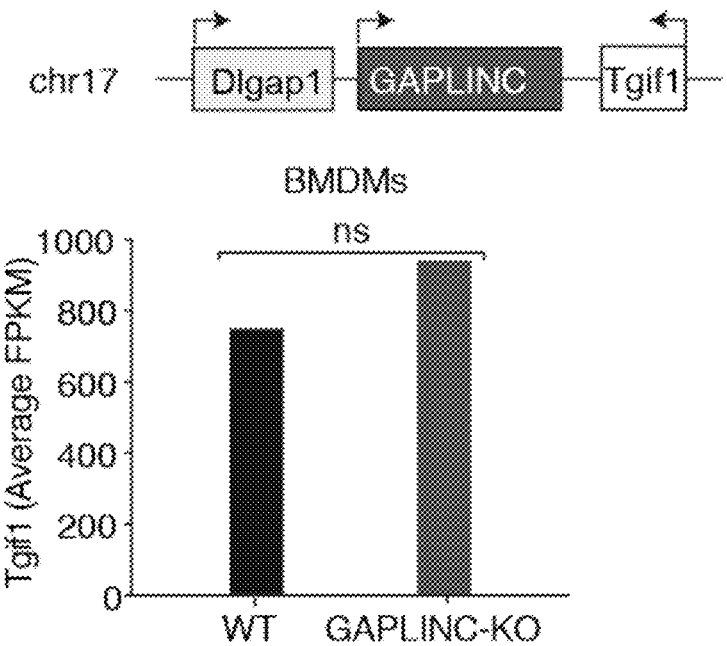
Figure 22B:
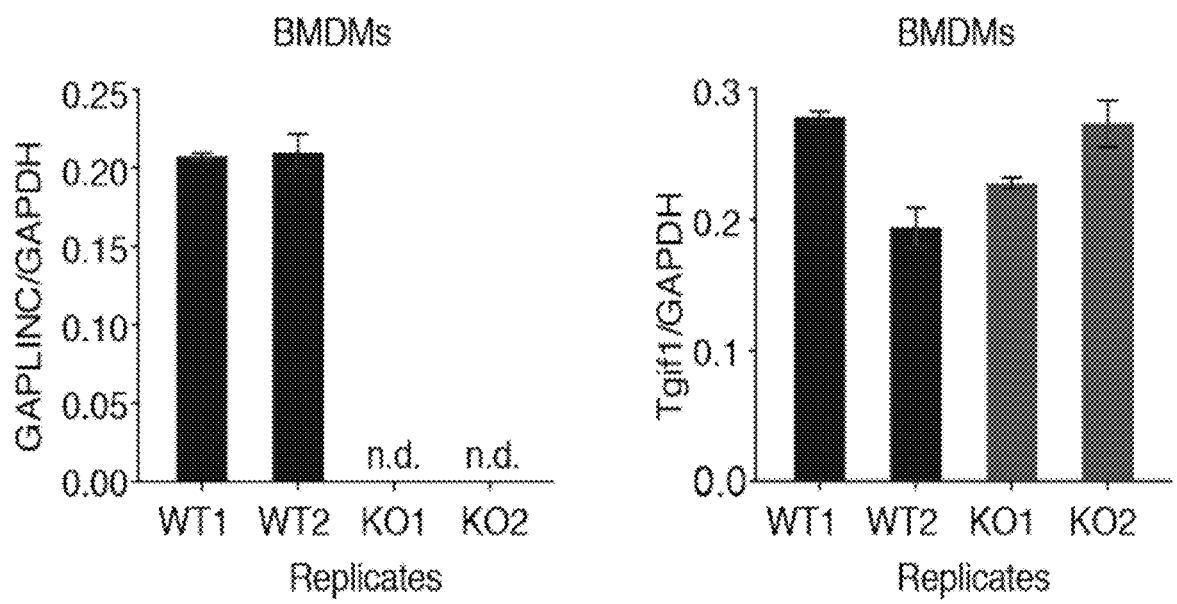

FIGS. 22A and 22B show that Gaplinc knockout does not affect neighboring genes. FIG. 22A: RNA-seq analysis of Tgif1 expression in WT and Gaplinc KO BMDMs, represented as average FPKM. FIG. 22B: qPCR analysis of Gaplinc and Tgif1 expression in WT and Gaplinc-KO BMDMs. ns, not significant, $p_{adj}>0.1$; n.d., not detectable.

Figure 23:
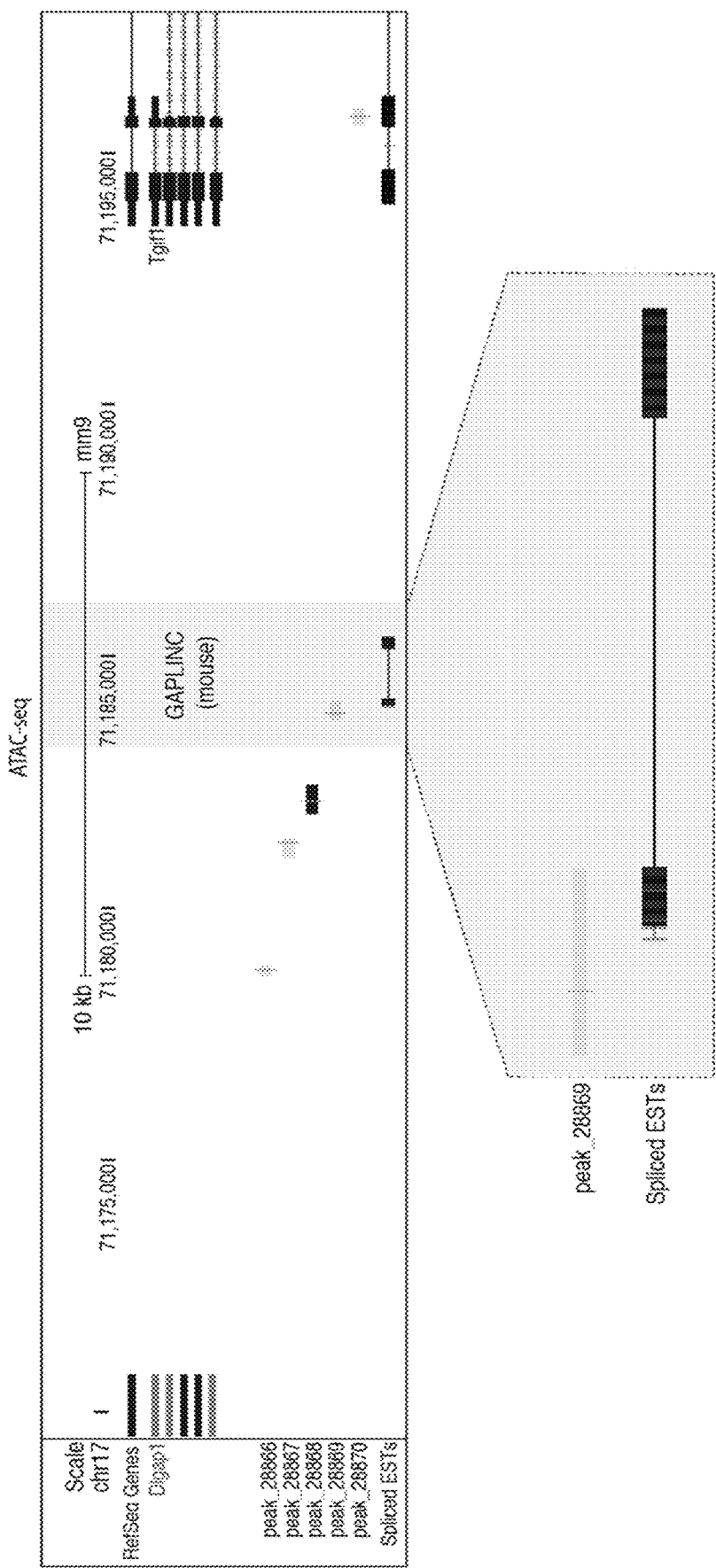

FIG. 23 shows that Gaplinc deletion region does not contain an enhancer element. Genome Browser snapshot of ATAC-seq data of the Gaplinc locus in wild type mouse BMDMs.

Figure 24A:
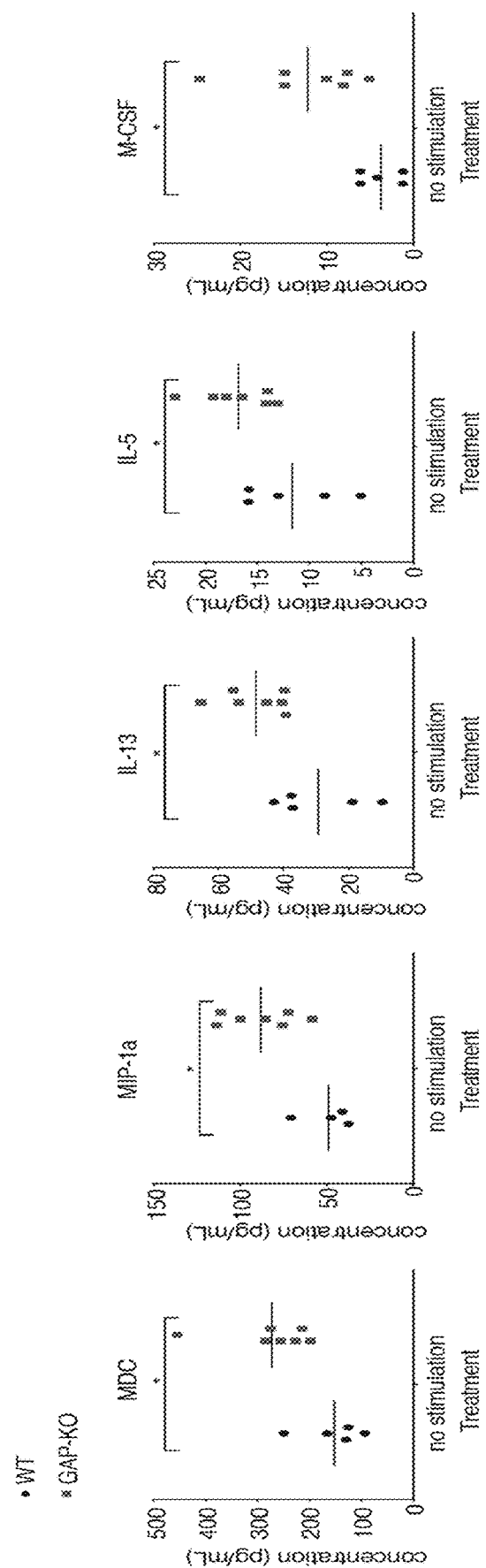
Figure 24B:
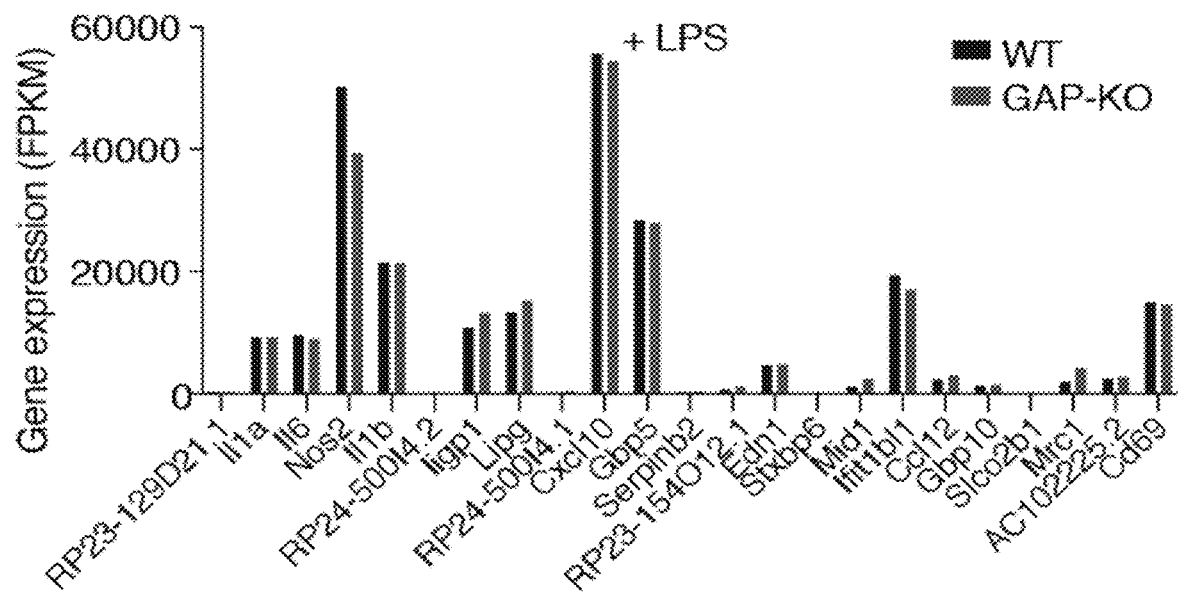
Figure 24C:
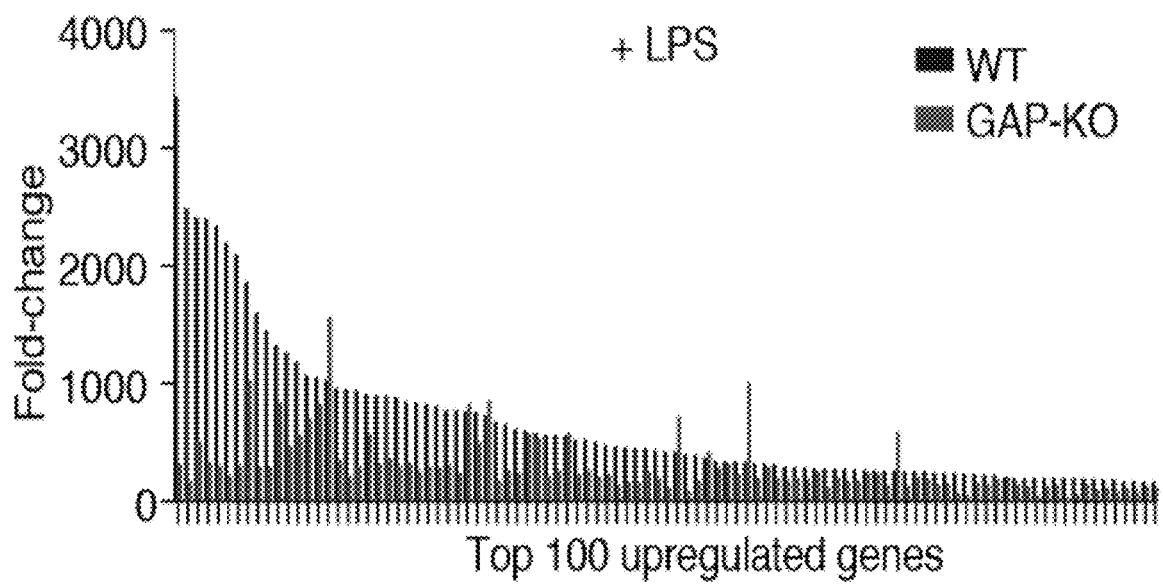
Figure 24D:
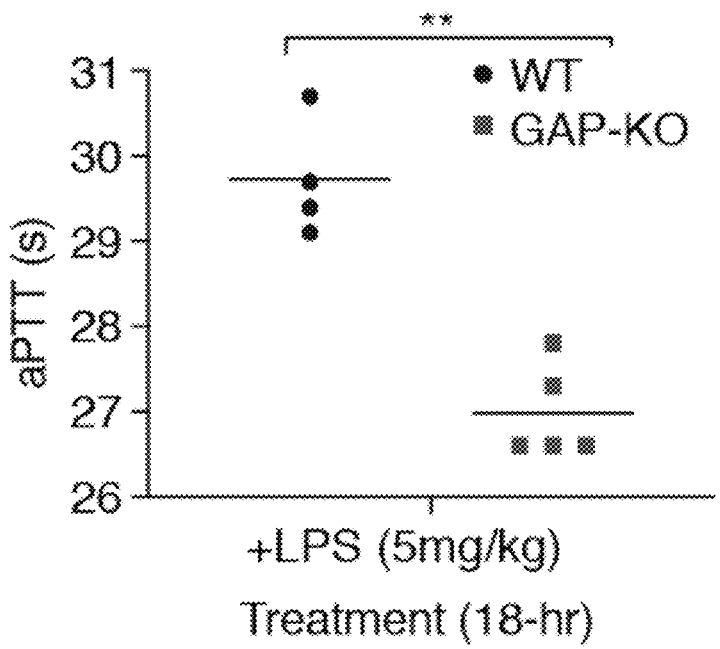
Figure 24E:
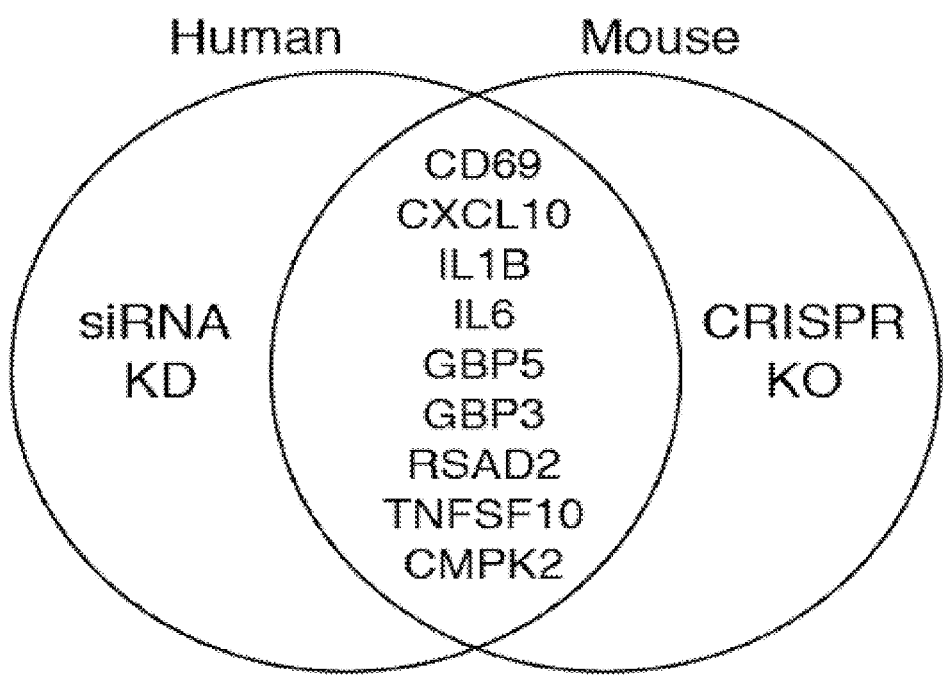
Figure 24F:
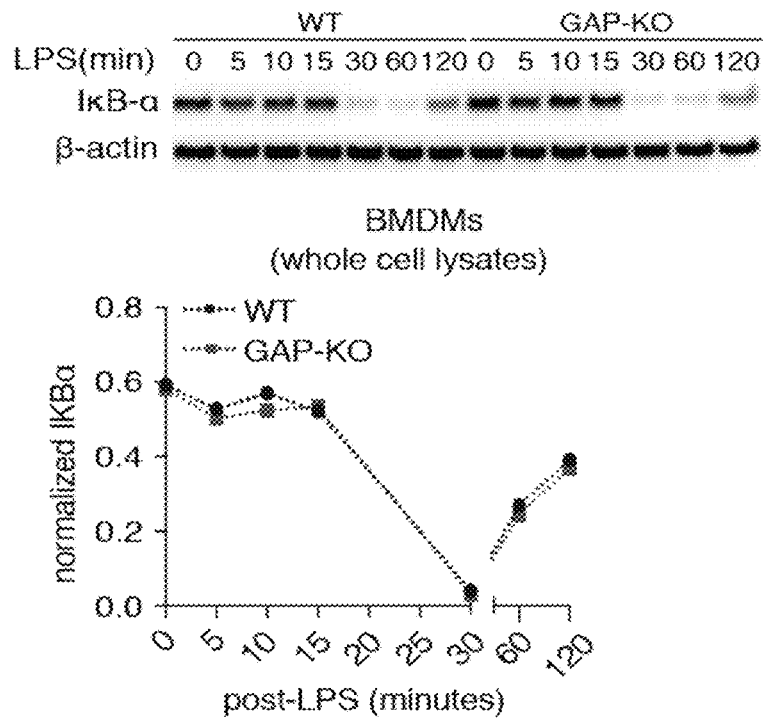
Figure 24G:
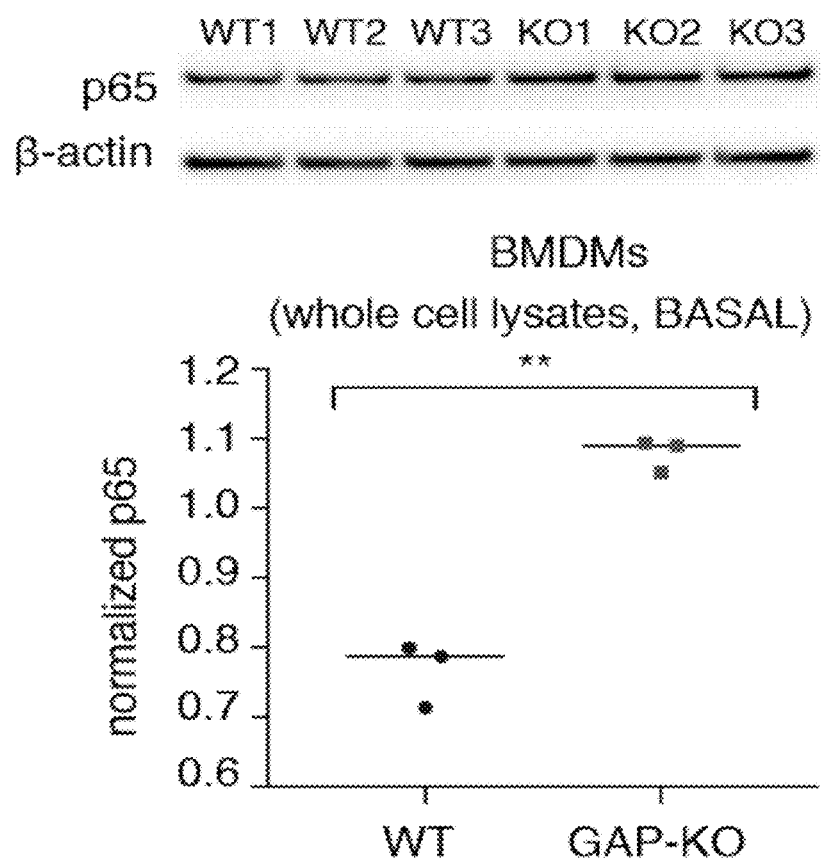
Figure 24H:
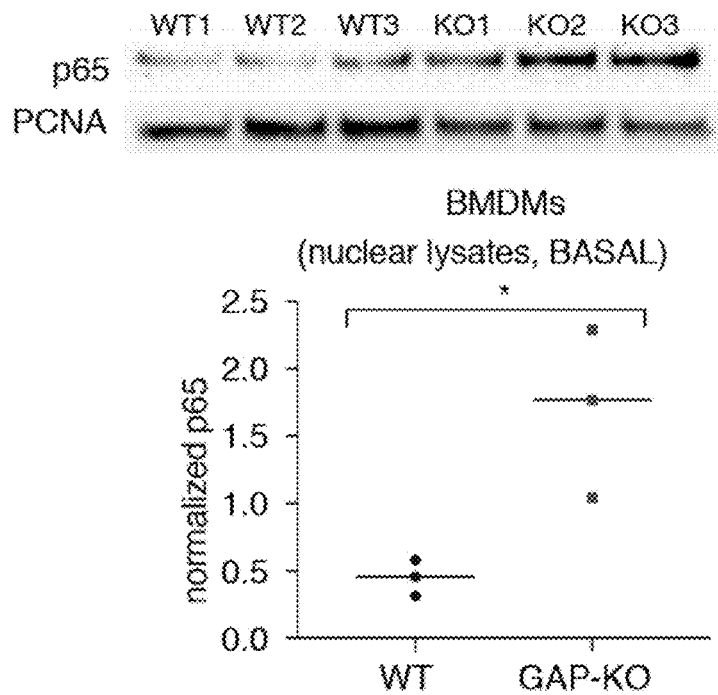

FIGS. 24A-24H show that Gaplinc knockout upregulates IRGs and shows increased levels of p65 in the nucleus at baseline. FIG. 24A: Cytokine levels in serum of WT and Gaplinc-KO mice at basal. (n=4-7). *$p<0.05$. FIGS. 24B and 24C: RNA-seq analysis in BMDMs from WT and Gaplinc-KO mice stimulated with LPS (200 ng/ml) for 6 h (n=3). The 23 genes upregulated in Gaplinc knockout-only conditions are compared to WT and Gaplinc-KO BMDMs stimulated with LPS. The resulting fold-change upon LPS stimulation is shown for WT and Gaplinc-KO BMDMs. Genes are ranked according to their fold-change in WT. FIG. 24D: Coagulation parameters assessed for WT and Gaplinc KO mice challenged i.p. with E. coli LPS (5 mg/kg/mice) (n=4-5). Plasma collected 18 h post-LPS injection. Activated Partial Thromboplastin Time (aPTT) was measured. FIG. 24E: Genes upregulated upon siRNA knockdown of human GAPLINC in monocyte-derived macrophages are compared to genes upregulated upon CRISPR/Cas9 knockout of mouse Gaplinc in bone-marrow-derived macrophages (fold-change ≥1.5). Upregulated genes overlapping in both human and mouse are shown in the middle. FIG. 24F: Western blot of IκB-α in WT and Gaplinc-KO BMDMs at the indicated times points following stimulation with LPS (200 ng/ml); these data are representative of three independent experiments. FIG. 24G: Western blot of p65 in WT and Gaplinc-KO BMDMs (n=3) at basal. **$p<0.01$. FIG. 24H: Western blot of p65 in nuclear fraction of WT and Gaplinc-KO BMDMs (n=3) at basal.

Figure 25A:
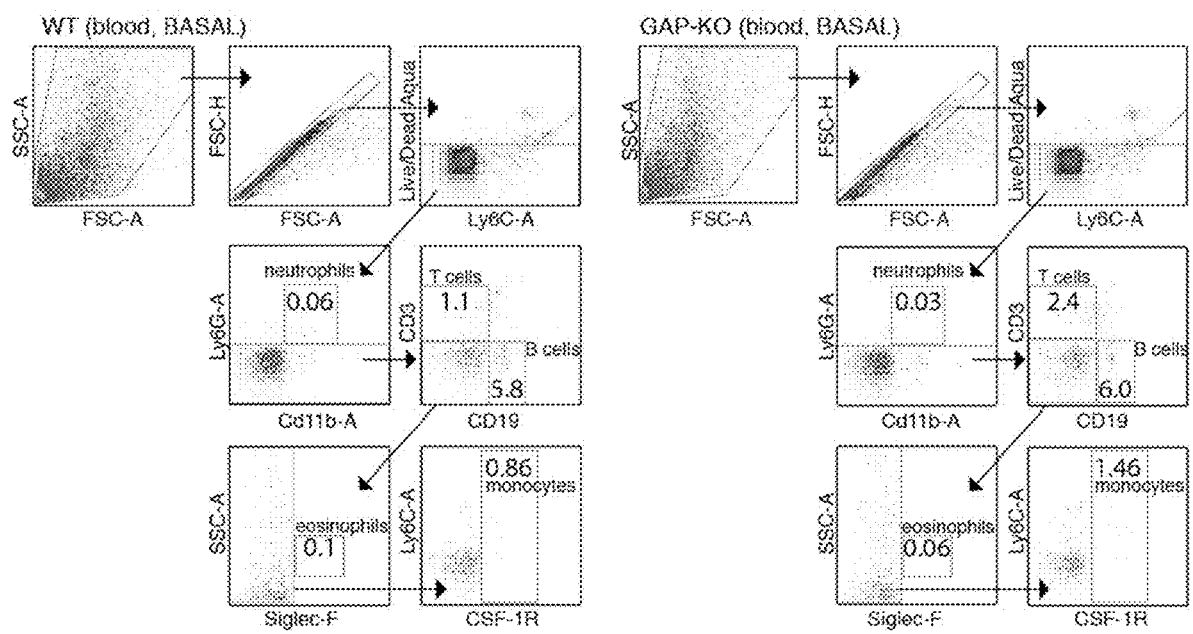
Figure 25B:
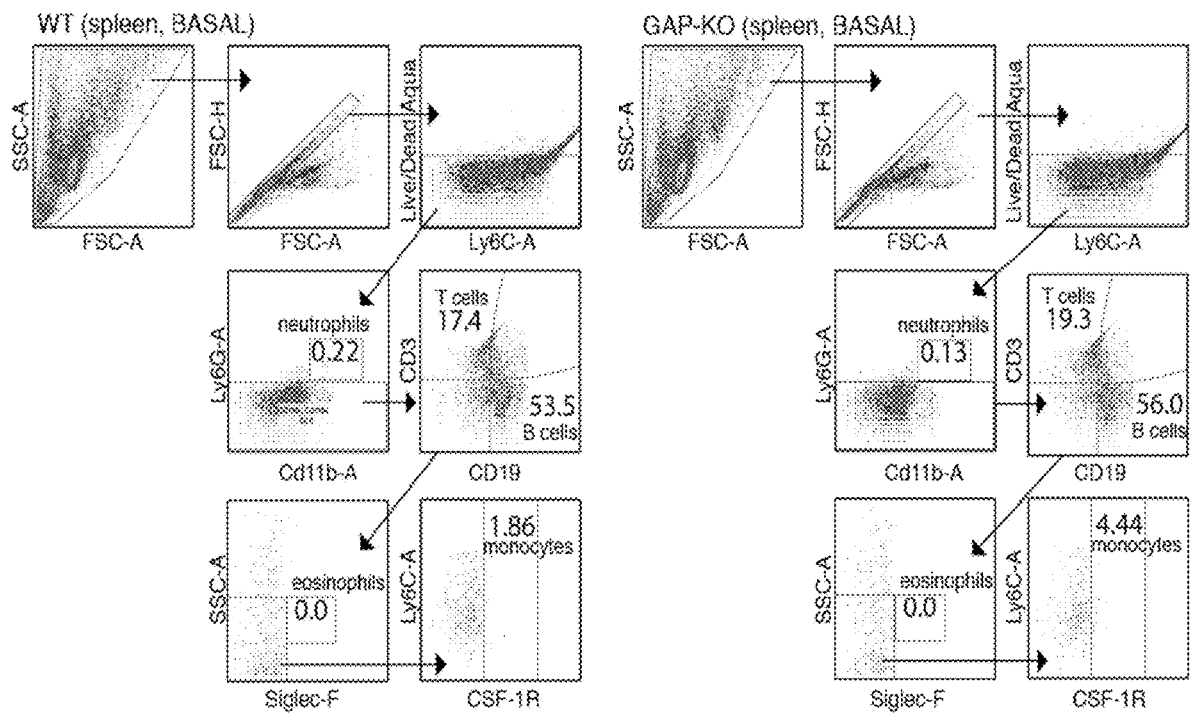

FIGS. 25A and 25B show the immune cell repertoire of WT and Gaplinc-KO mice at baseline. Cells isolated from the blood (FIG. 25A) and spleen (FIG. 25B) of WT and Gaplinc-KO mice. Flow cytometry plot demonstrates the gating strategy for neutrophils (CD11B+, LY6G+), T cells (Ly6G−, CD3+), B cells (Ly6G−, CD3−, CD19+), eosinophils (CD3−, CD19−, Ly6G−, SiglecF+, SSC hi), monocytes (CD3−, CD19−, Ly6G−, SiglecF−, Ly6C+, CSF-1R+). Results are representative of 3 mice/group. Flow plots depict results from 1 mouse (unpooled).

Figure 26A:
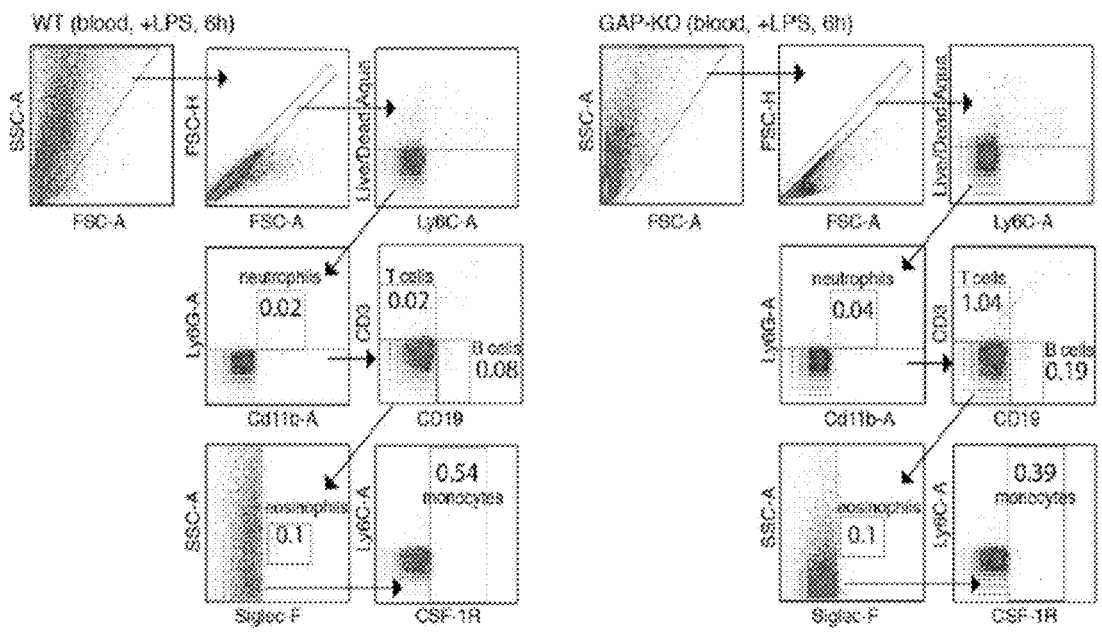
Figure 26B:
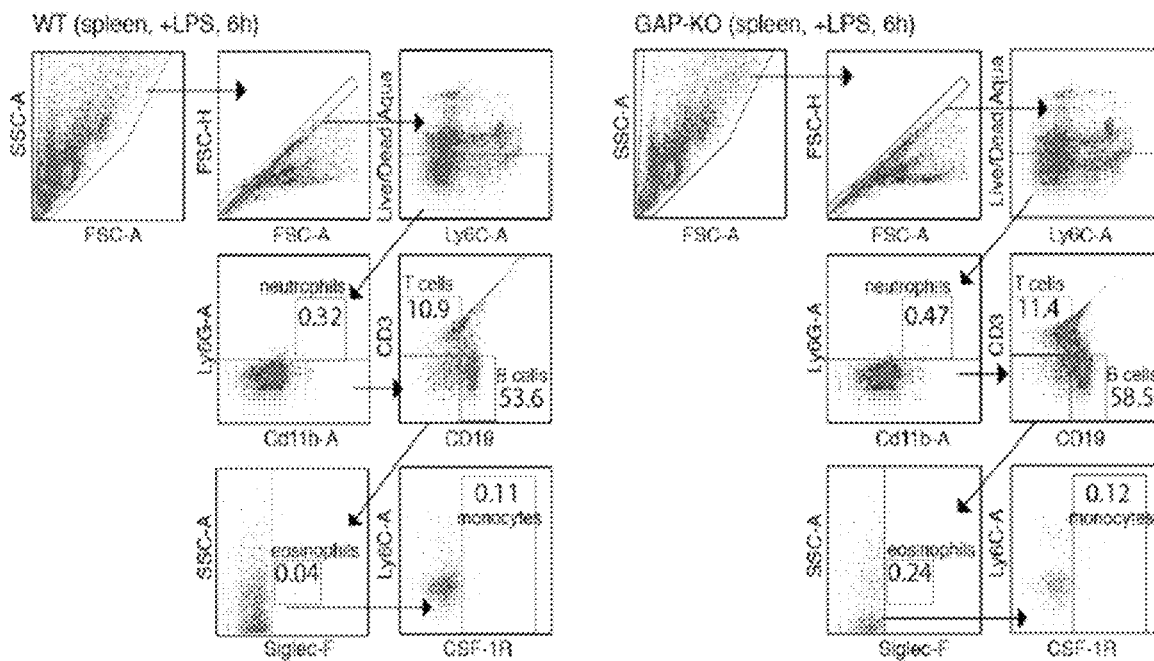

FIGS. 26A and 26B show the immune cell repertoire of WT and Gaplinc-KO mice after LPS challenge for 6 h. Cells isolated from the blood (FIG. 26A) and spleen (FIG. 26B) of WT and Gaplinc-KO mice challenged i.p. with E. coli LPS (5 mg/kg/mice) for 6 h. Flow cytometry plot demonstrates the gating strategy for neutrophils, T cells, B cells, eosinophils, and monocytes. Results representative of 6 mice/group. Flow plots depict results from 1 mouse (unpooled).

Figure 27A:
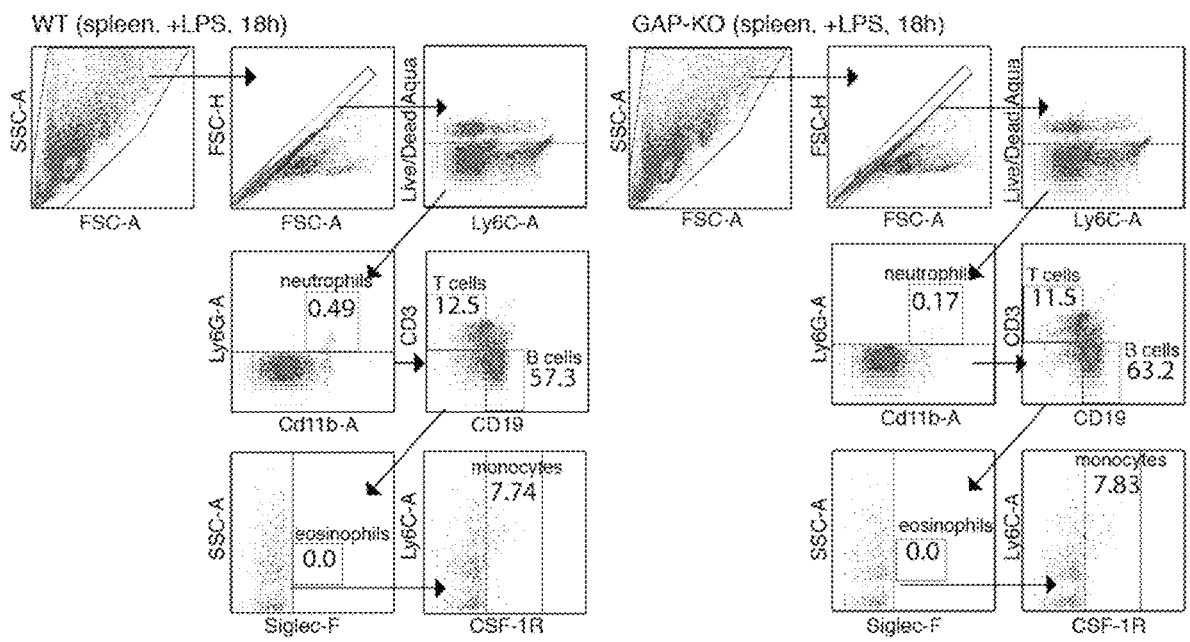
Figure 27B:
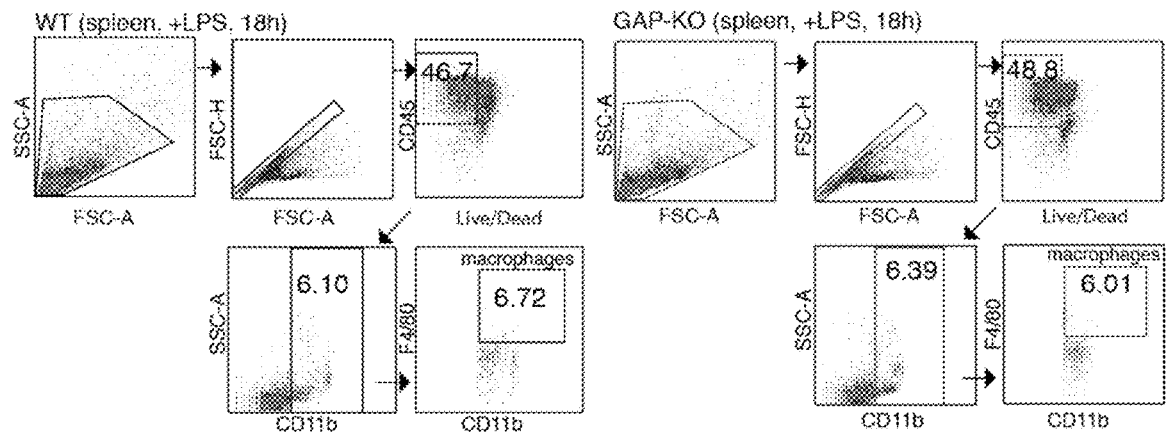
Figure 27C:
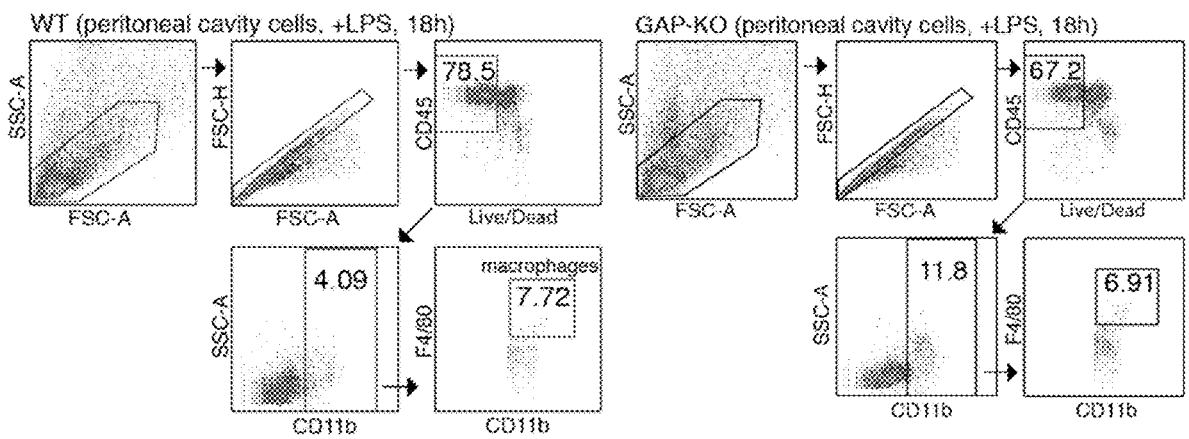

FIGS. 27A-27C show the immune cell repertoire of WT and Gaplinc-KO mice after LPS challenge for 18 h. Cells isolated from the spleen (FIG. 27A) of WT and Gaplinc-KO mice challenged i.p. with E. coli LPS (5 mg/kg/mice) for 18 h. Flow cytometry plot demonstrates the gating strategy for neutrophils, T cells, B cells, eosinophils, and monocytes. Cells isolated from spleen (FIG. 27B) and peritoneal cavity (FIG. 27C) of WT and Gaplinc-KO mice. Flow cytometry plot demonstrates the gating strategy for macrophages (Cd11b+, F4/80+). Results representative of 7 mice/group. Flow plots depict results from 1 mouse (unpooled).

Figure 28:
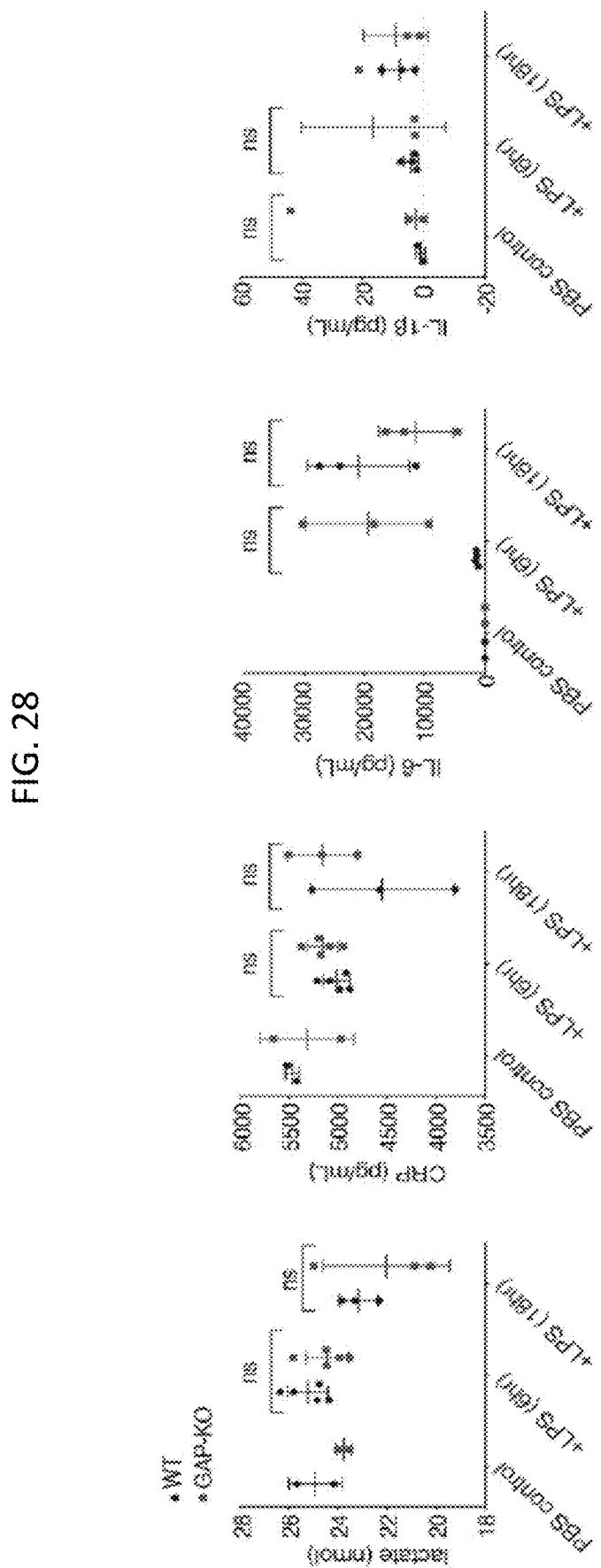

FIG. 28 shows that sepsis-associated clinical biomarkers are comparable between WT and Gaplinc-KO mice. Lactate, C-reactive protein (CRP), IL6 and IL113 levels in serum of WT and Gaplinc-KO mice challenged i.p. with E. coli LPS (5 mg/kg/mice) for 6 h (n=5) and 18 h (n=3). ns, not significant.

Figure 29A:
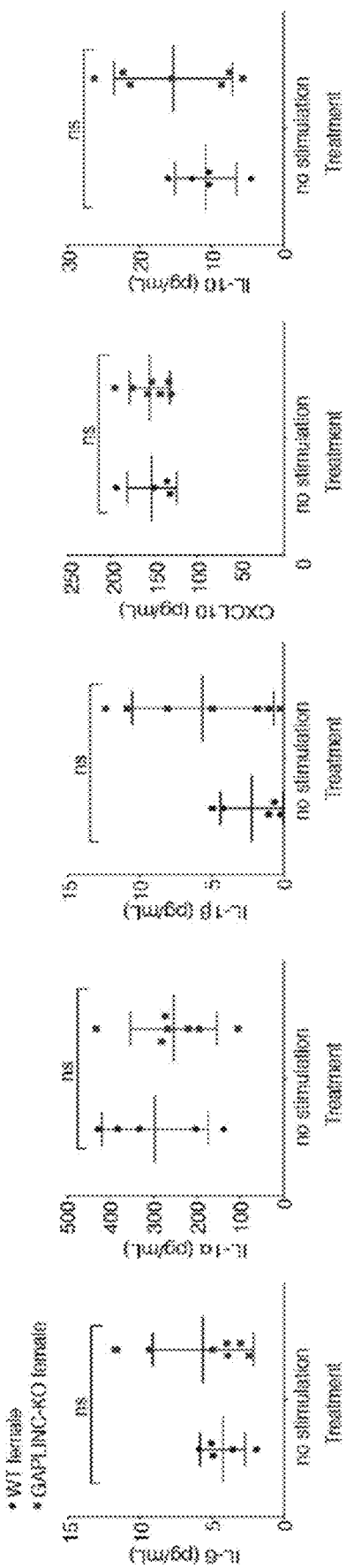
Figure 29B:
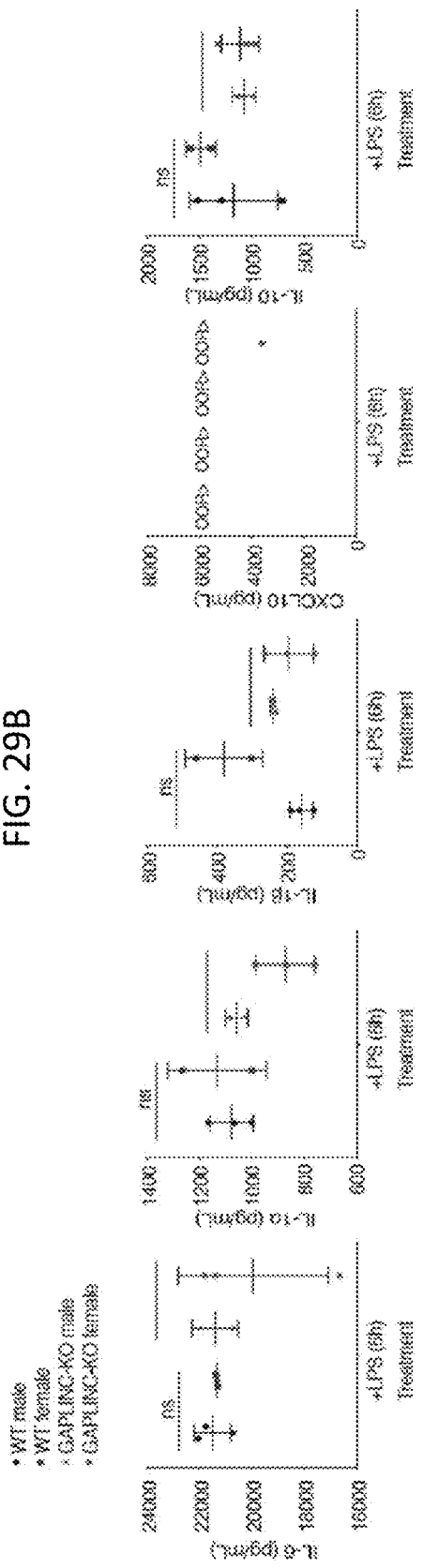
Figure 29C:
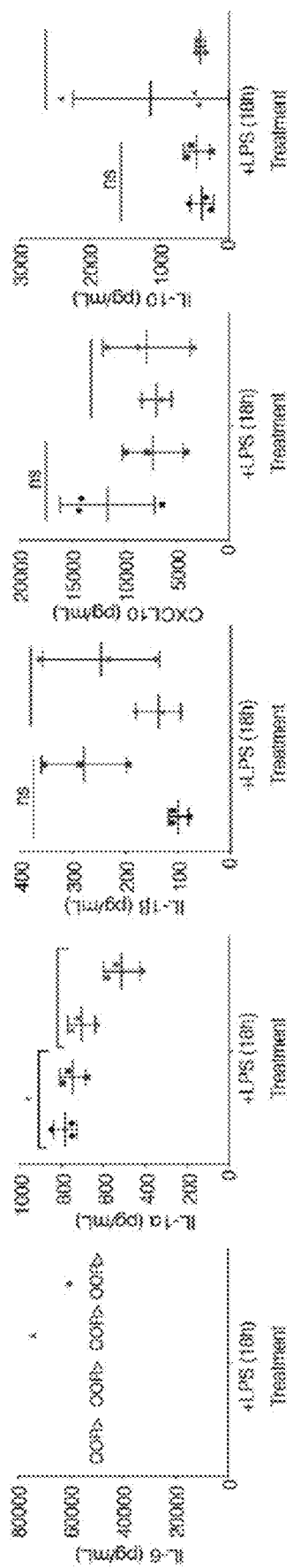

FIGS. 29A-29C show that inflammatory cytokine profiles for LPS-challenged WT and Gaplinc-KO mice. Cytokine levels in serum of WT and Gaplinc-KO mice at a, basal, and b, challenged i.p. with E. coli LPS (5 mg/kg/mice) for 6 h (n=5) and c, 18 h (n=6) *$p<0.05$; ns, not significant; OOR>, out of range, above standard curve.

Figure 30:
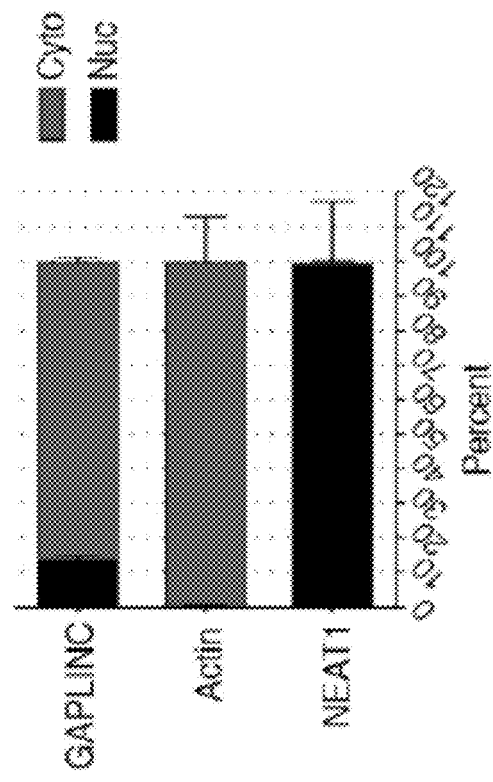

FIG. 30 shows that GAPLINC is localized to the cytoplasm. qPCR analysis of RNAs purified from nuclear (black) and cytoplasmic (gray) fractions in BMDMs.

Figure 31A:
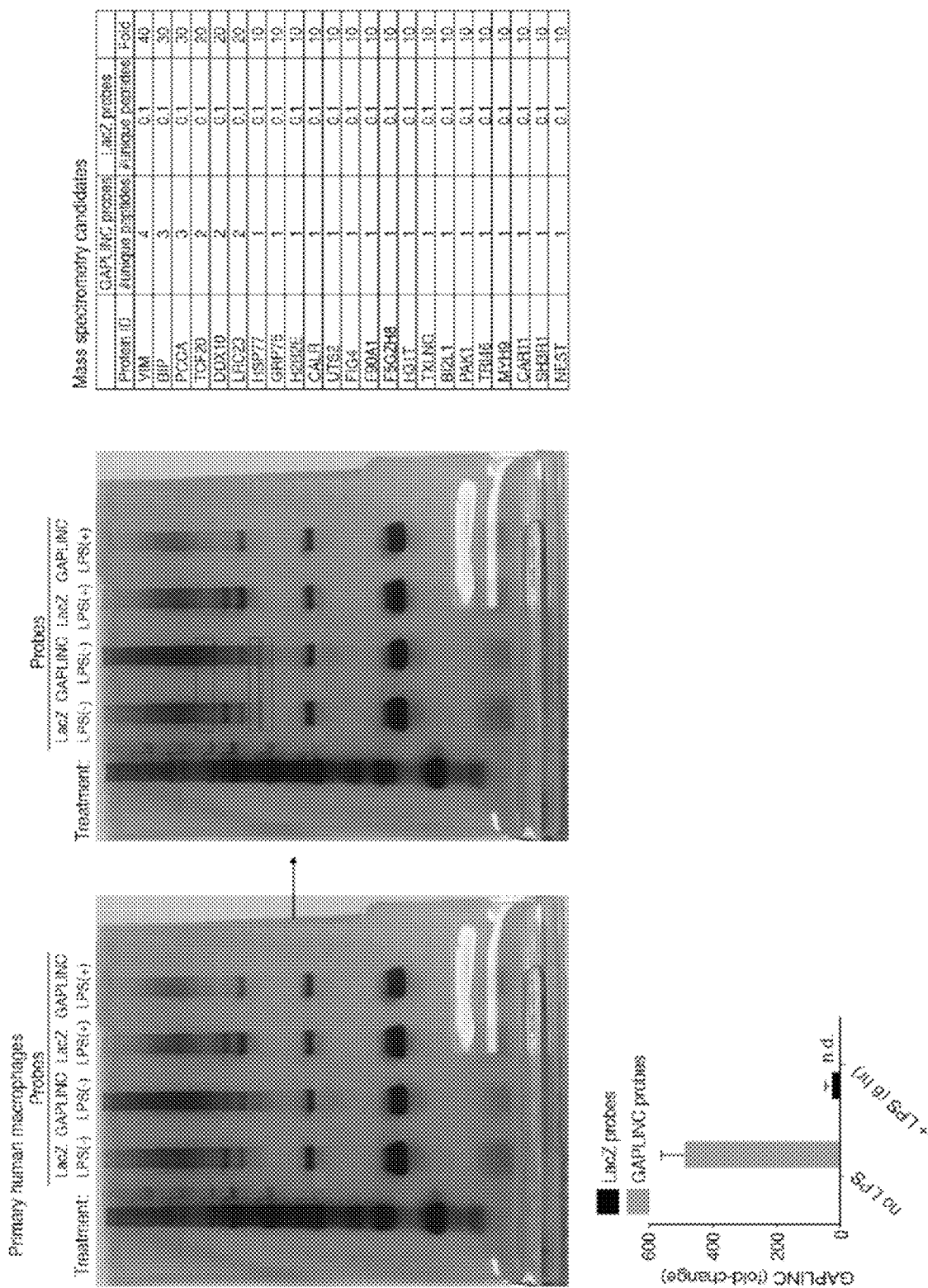
Figure 31B:
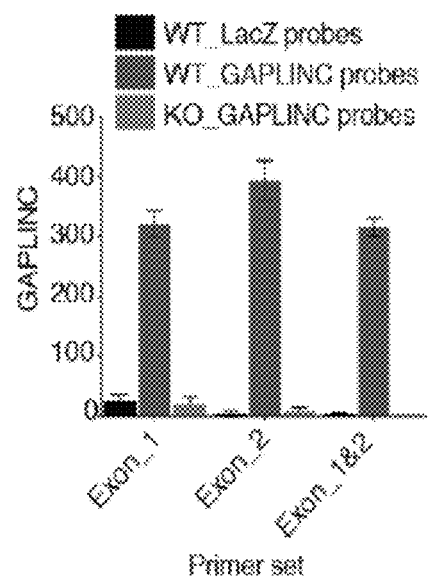

FIGS. 31A and 31B show a modified ChIRP. FIG. 31A: Biotinylated LacZ (non-specific) and GAPLINC-specific probes were used to capture endogenous GAPLINC in human MDM cell extracts and run on a polyacrylamide gel. LPS stimulated (200 ng/ml, 6 h) MDMs were used as a control for GAPLINC expression. Differentially expressed bands were excised and identified by mass spectrometry. The table represents candidates with fold-change ≥10 (GAPLINC/LacZ). The bar graph represents qPCR validation of GAPLINC enrichment after RNA pulldown using non-specific LacZ probes and GAPLINC-specific probes. FIG. 31B: Biotinylated LacZ (non-specific) and GAPLINC-specific probes were used to capture endogenous Gaplinc in WT BMDMs. Gaplinc-KO BMDMs was used as a control for Gaplinc expression. Liquid-based (gel-free) identification from each RNA pulldown was submitted for mass spectrometry. The table represents the peptide count for all proteins identified (no filter). The bar graph represents qPCR validation of Gaplinc enrichment after RNA pulldown using a combination of primers to detect Exon1, Exon2 and exon-spanning regions of the Gaplinc transcript.

Figure 32:
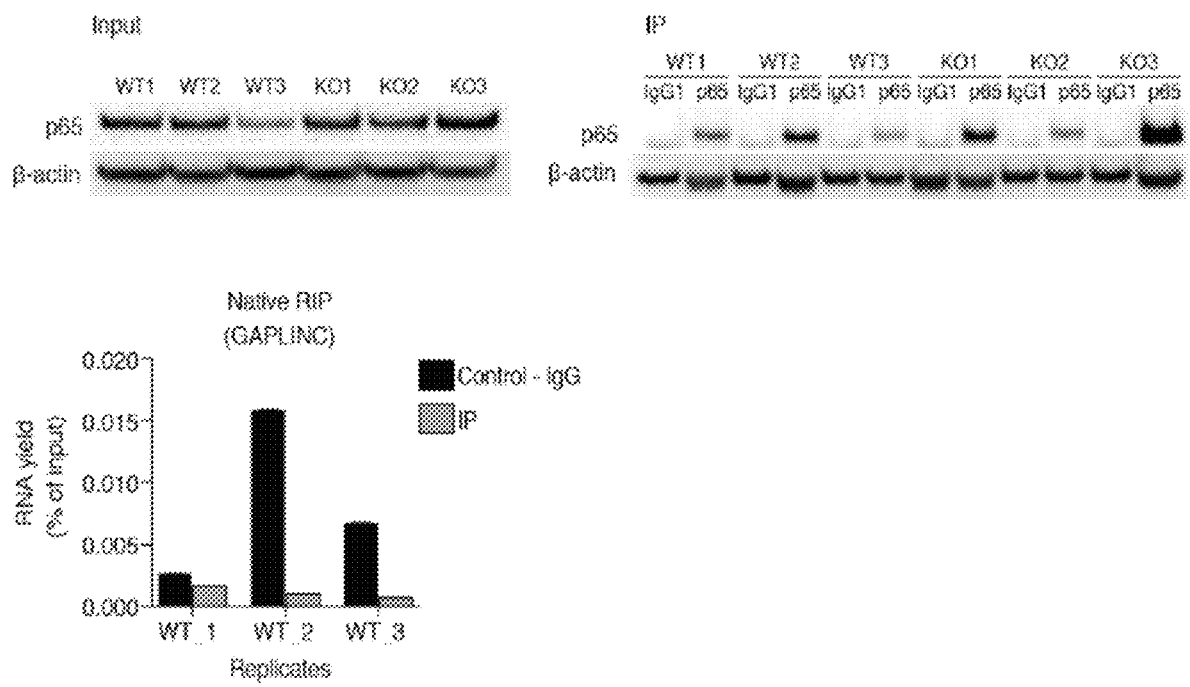

FIG. 32 shows that Gaplinc does not directly interact with p65. p65 RNA immunoprecipitation (RIP) in non-crosslinked WT and Gaplinc-KO BMDMs. Immunoprecipitation of p65 was assessed by Western Blot (top panels; left, input controls; right, IP). qPCR analysis for Gaplinc expression was performed in co-purified RNAs (bar graph). Enrichment of Gaplinc in p65 IP is compared to IgG control. p65 RIP-qPCR was performed in biological triplicate.

Figure 33:
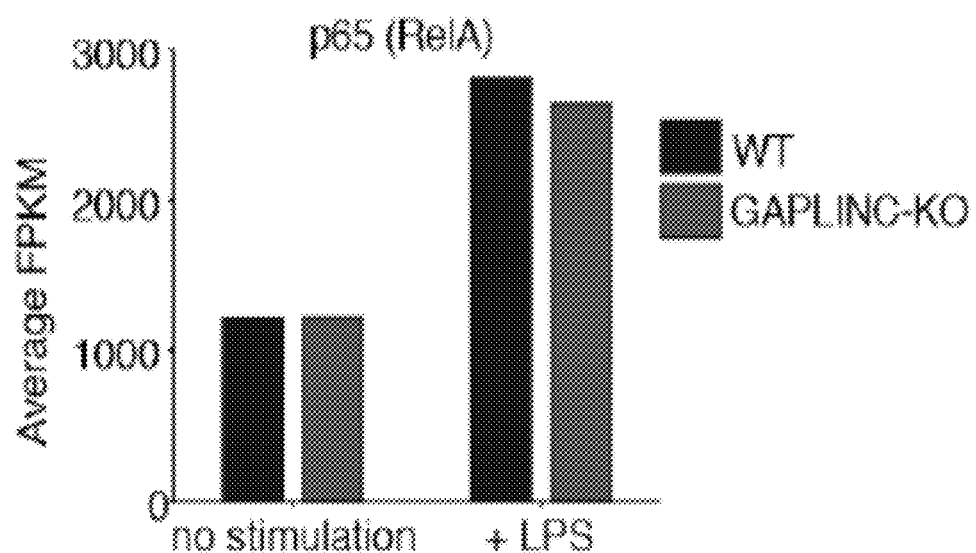

FIG. 33 shows that NFκB p65 transcript levels are comparable in WT and Gaplinc-KO BMDMs. RNA-seq analysis of p65 (RelA) expression in WT and Gaplinc-KO BMDMs in untreated and LPS-stimulated (200 ng/ml, 6 h) conditions.

DETAILED DESCRIPTION OF THE EMBODIMENTS

I. Introduction

The disclosure provides compositions and methods relating to a GAPLINC RNA, which is a lncRNA located on chromosome 18 between the protein-coding genes Tgif and Dlgap1. The disclosure features inhibitory agents that can be used to inhibit or reduce the expression of the GAPLINC RNA, as well as methods of using such inhibitory agents to treat an inflammatory disease, such as sepsis. As described herein, an inhibitory agent can be an antisense oligonucleotide (ASO), an siRNA, an miRNA, or an shRNA, and can include one or more modified nucleotides.

II. Inhibitory Agents

An inhibitory agent can be used to inhibit or reduce the expression of a GAPLINC RNA, such as a human or mouse GAPLINC RNA (e.g., a GAPLINC RNA having a sequence of SEQ ID NO:1 or 2).

A human GAPLINC RNA has the sequence of (SEQ ID NO: 1)
ACTTGCAGGATCTGACACATCCTCTTGGTTTCCTAAGTCTTATGACTAGC

CAATGCCTGAAATAATGAACTCCTCCAAGGCAAGAAATCTGTTTTGAAGC

TTCTCTGCGTTCACACACAGCAGCCTGGTTTCCTGGAAGGGCATTTTCCA

CATTGTGCGTTATGGATGATCATCCCAGGCATCAGGTGTGAAGCCCTGCA

TCCACATCCAGGGGCTATCAAATCTCTCTGCAAAAGGAGAAGCTGGACTC

AGGCACGTTTACAGTGATGTGTATGCAGGCTGGAATGCAGGGATGCGATC

TCGGCTCAATGCAACCTCTGCCGCCCAGGATTCAAGCGATTCTCCTGCCT

CAGCTTCTTGAGTATCTGGGATTACAGGCACCTGCCACCACGCCTGACTA

ATTTTTGTAGTTTTAGTAGAGCCAGGGTTTCACCATCTTGGCCAGGCTGG

TCTTGAACTCCTGACCTCGTGATCCACCCACCTTGTCTTCCCAAAGTGCT

GCGATTACAGGCGTGAGCCACCGTGCCCGGCTGACCAGTATCTTTCATGT

TACTATTGTAATTGTTTGGGGTCACCACGAACCGCACACATATAAGACAA

TGAACTTAATCAATAAACGTGTGTGTTCTGATTGCTCCATTCTGTGAAGG

AAGCTGCAGAAGAAAAGGTGAAAGAGGTGAGGAAGCTGCAGAAGAAAAC

CTGGAAGTTAGCAGAGCTTGATCCAGAGGTTTAAGGAAAGAAGCCATCTC

CATAACATAAAAGTGCAAGGTGAAGCAGCAAGTGCTGATGGGGAAGCTGC

AGCAAGTCATCCAGAAGATCTTGCTAAGGGTATGCACAGATGTGGAAACA

GGAACTGATGTGTCCATTACACCACTAGGACAGAGGCCAGAACAATGAAG

AAACCAAATACTTGGAAGAGGGTAGAGATAATGAATGGAGTCCAAGAGCC

CTGATTGTGCCATAAATGTCCAGATAATTCCATACCTGAGGATTATGTGG

TTTGTAAACTTGGCACTTAGAAGAACCAATAAAATCATGTTATAGTTTCA

A.

A mouse GAPLINC RNA has the sequence of (SEQ ID NO: 2)
AGCTCGGGAAGCCTGCAGGCTGTGAGCACGTTGATCAAAGGTCCCTTTGC

GGGCTCAAATTAACAGGGAGCTGGCGAGCCCGCGCAGCACCTGCCTGGGA

AGAGCAGCGCCACAGCAAACCGGCTCATCTTGCCGGGAGTATTTGGAAAT

GAACCTTGGACTTTAAGAACGCTTGGAGTCATTGAACCACACCCAACTCC

TATTCTGACATTTCACTGCTATCCAGGATTTACAGAAAATGTTAGAAAAA

CTCTGCAGCAATGTTATTTTGAAATTTATAAAGCCTTTACAAAAATGTGA

AGAAAGATGTATATATTTGTGGCATCTTGATCTCTACTATAAATTGCGAA

ATGATTGGATTGAGCTTAAGGTATTAAAGCTTTTA.

An inhibitory agent can be naturally occurring or synthetic. An inhibitory agent can target or hybridize to a sequence that is identical or substantially identical (e.g., at least 70%, at least 75%, at least 80%, at least 85%, at least 90%, at least 91%, at least 92%, at least 93%, at least 94%, at least 95%, at least 96%, at least 97%, at least 98%, or at least 99% identical) to a target sequence in a GAPLINC RNA (e.g., a portion comprising at least 10, at least 20, at least 30, at least 40, at least 50, at least 60, at least 70, at least 80, at least 90, or at least 100 contiguous nucleotides of the sequence of SEQ ID NO:1 or 2; e.g., from 20-500, 20-250, 20-100, 50-500, or 50-250 contiguous nucleotides of the sequence of SEQ ID NO:1 or 2).

In some embodiments, an inhibitory agent can be complementary to an equal length portion of a sequence of a GAPLINC RNA (e.g., a portion comprising at least 10, at least 20, at least 30, at least 40, at least 50, at least 60, at least 70, at least 80, at least 90, or at least 100 contiguous nucleotides of the sequence of SEQ ID NO:1 or 2; e.g., from 20-500, 20-250, 20-100, 50-500, or 50-250 contiguous nucleotides of the sequence of SEQ ID NO:1 or 2).

An inhibitory agent described herein can have at least 10 (e.g., at least 15, 20, 25, 30, 35, 40, 45, or 50) nucleotides in length. In certain embodiments, the inhibitory agent has between 15 and 30 (e.g., between 15 and 28, between 15 and 26, between 15 and 24, between 15 and 22, between 15 and 20, between 15 and 18, between 15 and 16, between 16 and 30, between 18 and 30, between 20 and 30, between 22 and 30, between 24 and 30, between 26 and 30, or between 28 and 30) nucleotides in length. In some embodiments, the inhibitory agent comprises an inhibitory RNA, e.g., an antisense oligonucleotide (ASO), a small interfering RNA (siRNA), a microRNA (miRNA), or a small hairpin RNA (shRNA).

ASO

An inhibitory agent can be an ASO that inhibits or reduces the expression of a GAPLINC RNA (e.g., a GAPLINC RNA having the sequence of SEQ ID NO:1 or 2). An ASO refers to an oligomer or polymer of nucleosides, such as naturally-occurring nucleosides (e.g., adenosine, guanosine, cytidine, 5-methyluridine, or uridine) or modified forms thereof, that are covalently linked to each other though internucleoside linkages. An ASO oligonucleotide is complementary to a target nucleic acid, such that the ASO hybridizes to the target nucleic acid sequence. As described herein, an ASO that inhibits or reduces the expression of a GAPLINK RNA (e.g., a GAPLINC RNA having the sequence of SEQ ID NO:1 or 2) can have a sequence that has at least 90% (e.g., 92%, 94%, 96%, 98%, or 100%) identity to a sequence of AUGUGGAUGCAGGGCUUCAC (SEQ ID NO:3), AUGUGGAAAATGCCCUUCCA (SEQ ID NO:4), AGU-CCAGCTTCTCCTUUUGC (SEQ ID NO:5), CUUGCCTTGGAGGAGUUCAU (SEQ ID NO:6), and GAUGCCTGGGATGATCAUCC (SEQ ID NO:7). In certain embodiments, an ASO can have a sequence of any one of SEQ ID NOS:3-7.

siRNA

An inhibitory agent can be an siRNA that inhibits or reduces the expression of a GAPLINC RNA (e.g., a GAPLINC RNA having the sequence of SEQ ID NO:1 or 2). An siRNA can be a double-stranded RNA with the two complementary strands. In some embodiments, each complementary strand can have between 15 and 30 (e.g., between 15 and 28, between 15 and 26, between 15 and 24, between 15 and 22, between 15 and 20, between 15 and 18, between 15 and 16, between 16 and 30, between 18 and 30, between 20 and 30, between 22 and 30, between 24 and 30, between 26 and 30, or between 28 and 30) nucleotides. In some embodiments, the two strands of an siRNA molecule can each have a 3'-end overhang of two or three nucleotides. In an siRNA molecule, one strand (e.g., the antisense strand) is guiding and complementary to the GAPLINC RNA.

In some embodiments, an siRNA that inhibits or reduces the expression of a GAPLINK RNA (e.g., a GAPLINC RNA having the sequence of SEQ ID NO:1 or 2) can have a sense region and an antisense region. In some embodiments, the antisense region can have a sequence having at least 90% (e.g., 92%, 94%, 96%, 98%, or 100%) identity to a sequence of any one of UUUGGUUUCUUCAUUGUUCTG (SEQ ID NO:9), GAAGAAAACCUGGAAGUUATT (SEQ ID NO:11), UUUACAAACCACAUAAUCCTC (SEQ ID NO:13), UUUGGUUUCUUCAUUGUUC (SEQ ID NO:15), GAAGAAAACCUGGAAGUUA (SEQ ID NO:17), and UUUACAAACCACAUAAUCC (SEQ ID NO:19). In certain embodiments, the antisense region comprises a sequence of any one of SEQ ID NOS: 9, 11, 13, 15, 19, and 19. In some embodiments, the sense region in an siRNA can have a sequence having at least 90% identity to a sequence of GAACAAUGAAGAAACCAAATT (SEQ ID NO:8), GAAGAAAACCUGGAAGUUATT (SEQ ID NO:10), GGAUUAUGUGGUUUGUAAATT (SEQ ID NO:12), GAACAAUGAAGAAACCAAA (SEQ ID NO:14), GAAGAAAACCUGGAAGUUA (SEQ ID NO:16), and GGAUUAUGUGGUUUGUAAA (SEQ ID NO:18). In certain embodiments, the sense region comprises a sequence of any one of SEQ ID NOS:8, 10, 12, 14, 16, and 18.

An siRNA can be a double-stranded RNA comprising a sense strand having a sequence with at least 90% (e.g., 92%, 94%, 96%, 98%, or 100%) identity to the sequence of GAACAAUGAAGAAACCAAATT (SEQ ID NO:8) and an antisense strand having a sequence with at least 90% (e.g., 92%, 94%, 96%, 98%, or 100%) identity to the sequence of UUUGGUUUCUUCAUUGUUCTG (SEQ ID NO:9). An siRNA can be a double-stranded RNA comprising a sense strand having a sequence with at least 90% (e.g., 92%, 94%, 96%, 98%, or 100%) identity to the sequence of GAAGAAAACCUGGAAGUUATT (SEQ ID NO:10) and an antisense strand having a sequence with at least 90% (e.g., 92%, 94%, 96%, 98%, or 100%) identity to the sequence of GAAGAAAACCUGGAAGUUATT (SEQ ID NO:11). An siRNA can be a double-stranded RNA comprising a sense strand having a sequence with at least 90% (e.g., 92%, 94%, 96%, 98%, or 100%) identity to the sequence of GGAUUAUGUGGUUUGUAAATT (SEQ ID NO:12) and an antisense strand having a sequence with at least 90% (e.g., 92%, 94%, 96%, 98%, or 100%) identity to the sequence of UUUACAAACCACAUAAUCCTC (SEQ ID NO:13).

An siRNA can be a double-stranded RNA comprising a sense strand having a sequence with at least 90% (e.g., 92%, 94%, 96%, 98%, or 100%) identity to the sequence of GAACAAUGAAGAAACCAAA (SEQ ID NO:14) and an antisense strand having a sequence with at least 90% (e.g., 92%, 94%, 96%, 98%, or 100%) identity to the sequence of UUUGGUUUCUUCAUUGUUC (SEQ ID NO:15). An siRNA can be a double-stranded RNA comprising a sense strand having a sequence with at least 90% (e.g., 92%, 94%, 96%, 98%, or 100%) identity to the sequence of GAAGAAAACCUGGAAGUUA (SEQ ID NO:16) and an antisense strand having a sequence with at least 90% (e.g., 92%, 94%, 96%, 98%, or 100%) identity to the sequence of GAAGAAAACCUGGAAGUUA (SEQ ID NO:17). An siRNA can be a double-stranded RNA comprising a sense strand having a sequence with at least 90% (e.g., 92%, 94%, 96%, 98%, or 100%) identity to the sequence of GGAUUAUGUGGUUUGUAAA (SEQ ID NO:18) and an antisense strand having a sequence with at least 90% (e.g., 92%, 94%, 96%, 98%, or 100%) identity to the sequence of UUUACAAACCACAUAAUCC (SEQ ID NO:19).

Suitable siRNA sequences can be identified using methods known in the art. For example, prediction algorithms that predict potential siRNA-targets based upon complementary DNA sequences in the target genes are available in the art. TargetScanHuman, for example, is a comprehensive web resource for inhibitory RNA-target predictions, and uses an algorithm that incorporates current biological knowledge of inhibitory RNA-target rules including evolutionary conservation and and free binding energy (Li and Zhang, *Wiley Interdiscip Rev RNA* 6:435-452, 2015 and Agarwal et al., *Elife* 4, 2015). The target sites predicted by TargetScanHuman are scored for likelihood of mRNA down-regulation using context scores (CS), a regression model that is trained on sequence and contextual features of the predicted inhibitory RNA::mRNA duplex. In some embodiments, to further enhance silencing efficiency of the siRNA sequences, potential siRNA sequences may be analyzed to identify sites that do not contain regions of homology to other coding sequences. Once a potential siRNA sequence has been identified, a complementary sequence (e.g., an antisense strand sequence) can be designed.

In some embodiments, potential siRNA sequences may be further analyzed based on siRNA duplex asymmetry as described in, e.g., Khvorova et al., *Cell* 115:209-216, 2003 and Schwarz et al., *Cell* 115:199-208, 2003. In other embodiments, potential siRNA sequences may be further analyzed based on secondary structure at the target site as described in, e.g., Luo et al., *Biophys. Res. Commun.* 318: 303-310, 2004. For example, secondary structure at the target site can be modeled using available techniques in the art, e.g., Mfold algorithm to select siRNA sequences which favor accessibility at the target site where less secondary structure in the form of base-pairing and stem-loops is present.

miRNA

An inhibitory agent can be an miRNA that inhibits or reduces the expression of a GAPLINC RNA (e.g., a GAPLINC RNA having the sequence of SEQ ID NO:1 or 2). An miRNA can be a single-stranded RNA molecule comprising between 15 and 30 (e.g., between 15 and 28, between 15 and 26, between 15 and 24, between 15 and 22, between 15 and 20, between 15 and 18, between 15 and 16, between 16 and 30, between 18 and 30, between 20 and 30, between 22 and 30, between 24 and 30, between 26 and 30, or between 28 and 30; e.g., 21, 22, or 23) nucleotides in length. miRNAs are encoded by genes from whose DNA they are transcribed, but miRNAs are not translated into protein (non-coding RNA); instead, each primary transcript (a pri-miRNA) is processed into a short stem-loop structure called a pre-miRNA and finally into a functional mature miRNA. Mature miRNA molecules are either partially or completely complementary to one or more messenger RNA (mRNA) molecules.

miRNAs are first transcribed as primary transcripts or pri-miRNA with a cap and poly-A tail and processed to short, nucleotide stem-loop structures known as pre-miRNA in the cell nucleus by a protein complex known as the Microprocessor complex, consisting of the nuclease Drosha and the double-stranded RNA binding protein Pasha (Denli et al., Nature, 432:231-235,2004). These pre-miRNAs are then processed to mature miRNAs in the cytoplasm by interaction with the endonuclease Dicer, which also initiates the formation of the RNA-induced silencing complex (RISC) (Bernstein et al., Nature, 409:363-366, 2001). Either the sense strand or antisense strand of DNA can function as templates to give rise to miRNA. When Dicer cleaves the pre-miRNA stem-loop, two complementary short RNA molecules are formed, but only one is integrated into the RISC complex. This strand is known as the guide strand and is selected by the argonaute protein, which is the catalytically active RNase in the RISC complex, on the basis of the stability of the 5' end (Preall et al., Curr. Biol., 16:530-535, 2006). The remaining strand, known as the anti-guide or passenger strand, is degraded as a RISC complex substrate). After integration into the active RISC complex, miRNAs base pair with their complementary mRNA molecules and induce target mRNA degradation and/or translational silencing.

Mammalian miRNA molecules are usually complementary to a site in the 3' UTR of the target mRNA sequence. In some embodiments, the annealing of the miRNA to the target mRNA inhibits protein translation by blocking the protein translation machinery. In some embodiments, the annealing of the miRNA to the target mRNA facilitates the cleavage and degradation of the target mRNA through a process similar to RNA interference (RNAi).

shRNA

An inhibitory agent can be an shRNA that inhibits or reduces the expression of a GAPLINC RNA (e.g., a GAPLINC RNA having the sequence of SEQ ID NO:1 or 2). An shRNA is a short RNA sequence that makes a tight hairpin turn that can be used to silence gene expression via RNA interference. The shRNA hairpin structure is cleaved by the cellular machinery into siRNA, which is then bound to the RNA-induced silencing complex (RISC). In some embodiments, shRNAs can be between 15 to 60 nucleotides (e.g., 15, 20, 25, 30, 35, 40, 45, 50, 55, or 60 nucleotides) in length. Non-limiting examples of shRNA include a double-stranded polynucleotide molecule assembled from a single-stranded molecule, in which the sense and antisense regions are linked by a nucleic acid-based or non-nucleic acid-based linker; and a double-stranded polynucleotide molecule with a hairpin secondary structure having self-complementary sense and antisense regions.

III. Modified Nucleotides

Any of the inhibitory agents described herein can include one or more modified nucleotides. A modified nucleotide refers to a nucleotide having at least one change that is structurally distinguishable from a naturally-occurring nucleotide (e.g., adenosine, guanosine, cytidine, 5-methyluridine, or uridine). A modified nucleotide may include a modified nucleobase and/or a modified sugar. Any of the inhibitory agents described herein can include one or more modified nucleobases, one or more modified sugars, and/or one or more modified internucleoside linkages. Examples of modified nucleobases, modified sugars, and modified internucleoside linkages are described in detail further herein.

Modified Nucleobases

A modified nucleobase (or base) refers to a nucleobase having at least one change that is structurally distinguishable from a naturally-occurring nucleobase (e.g., adenine, guanine, cytosine, thymine, or uracil). In some embodiments, a modified nucleobase is functionally interchangeable with its naturally-occurring counterpart. Both naturally-occurring and modified nucleobases are capable of hydrogen bonding. Modifications on modified nucleobases may help to improve the stability of the inhibitory agents to nucleases, increase binding affinity of the inhibitory agents to their target nucleic acids, and decrease off-target binding of the inhibitory agents. In some embodiments, an inhibitory agent described herein may include at least one modified nucleobase. Examples of modified nucleobases include, but are not limited to, 5-methylcytosine, 5-hydroxymethyl cytosine, xanthine, hypoxanthine, 2-aminoadenine, 6-methyladenine, 6-methylguanine, 2-propyladenine, 2-propylguanine, 2-thiouracil, 2-thiothymine, 2-thiocytosine, 5-halouracil, 5-halocytosine, 5-propynyluracil, 5-propynylcytosine, 6-azouracil, 6-azocytosine, 6-azothymine, 5-uracil (pseudouracil), 4-thiouracil, 8-haloadenine, 8-aminoadenine, 8-thioladenine, 8-thioalkyladenine, 8-hydroxyladenine, 8-haloguanine, 8-aminoguanine, 8-thiolguanine, 8-thioalkylguanine, 8-hydroxylguanine, 5-halouracil, 5-bromouracil, 5-trifluoromethyluracil, 5-halocytosine, 5-bromocytosine, 5-trifluoromethylcytosine, 7-methylguanine, 7-methyladenine, 2-fluoroadenine, 2-aminoadenine, 8-azaguanine, 8-azaadenine, 7-deazaguanine, 7-deazaadenine, 3-deazaguanine, and 3-deazaadenine.

Modified Sugars

A modified sugar refers to a sugar having at least one change that is structurally distinguishable from a naturally-occurring sugar (e.g., 2'-deoxyribose in DNA or ribose in RNA). Modifications on modified sugars may help to improve the stability of the inhibitory agents to nucleases, increase binding affinity of the inhibitory agents to their target nucleic acids, and decrease off-target binding of the inhibitory agents. In some embodiments, the sugar is a pentofuranosyl sugar. The pentofuranosyl sugar ring of a nucleoside may be modified in various ways including, but not limited to, addition of a substituent group, particularly, at the 2' position of the ring; bridging two non-geminal ring atoms to form a bicyclic sugar (e.g., a locked sugar); and substitution of an atom or group such as —S—, —N(R)— or —C($R_1$)($R_2$) for the ring oxygen. Examples of modified sugars include, but are not limited to, substituted sugars, especially 2'-substituted sugars having a 2'-F, 2'-OCH$_3$ (2'-OMe), or a 2'-O(CH$_2$)$_2$—OCH$_3$ (2'-O-methoxyethyl or 2'-MOE) substituent group; and bicyclic sugars. A bicyclic sugar refers to a modified pentofuranosyl sugar containing two fused rings. For example, a bicyclic sugar may have the 2' ring carbon of the pentofuranose linked to the 4' ring carbon by way of one or more carbons (e.g., a methylene) and/or heteroatoms (e.g., sulfur, oxygen, or nitrogen). The second ring in the sugar limits the flexibility of the sugar ring and thus, constrains the oligonucleotide in a conformation that is favorable for base pairing interactions with its target nucleic acids. An example of a bicyclic sugar is a locked sugar, which is a pentofuranosyl sugar having the 2'-oxygen linked to the 4' ring carbon by way of a carbon (e.g., a methylene) or a heteroatom (e.g., sulfur, oxygen, or nitrogen). In some embodiments, a locked sugar has the 2'-oxygen linked to the 4' ring carbon by way of a carbon (e.g., a methylene). In other words, a locked sugar has a 4'-($CH_2$)—O-2' bridge, such as α-L-methyleneoxy (4'-$CH_2$—O-2') and β-D-methyleneoxy (4'-$CH_2$—O-2'). A nucleoside having a lock sugar is referred to as a locked nucleoside.

Other examples of bicyclic sugars include, but are not limited to, (6'S)-6' methyl bicyclic sugar, aminooxy (4'-$CH_2$—O—N(R)-2') bicyclic sugar, oxyamino (4'-$CH_2$—N(R)—O-2') bicyclic sugar, wherein R is, independently, H, a protecting group or C1-C12 alkyl, and the fused ring system in a tricycle (tc)-DNA. The substituent at the 2' position can also be selected from allyl, amino, azido, thio, O-allyl, O—C1-C10 alkyl, $OCF_3$, O($CH_2$)$_2$$SCH_3$, O($CH_2$)$_2$—O—N($R_m$)($R_n$), and O—$CH_2$—C(=O)—N($R_m$)($R_n$), wherein each $R_m$ and $R_n$ is, independently, H or substituted or unsubstituted C1-C10 alkyl.

In some embodiments, a modified sugar is an unlocked sugar. An unlocked sugar refers to an acyclic sugar that has a 2',3'-seco acyclic structure, where the bond between the 2' carbon and the 3' carbon in a pentofuranosyl ring is absent.

Modified Internucleoside Linkages

An internucleoside linkage refers to the backbone linkage that connects the nucleosides. An internucleoside linkage may be a naturally-occurring internucleoside linkage (e.g., a phosphate linkage, also referred to as a 3' to 5' phosphodiester linkage, which is found in DNA and RNA) or a modified internucleoside linkage. A modified internucleoside linkage refers to an internucleoside linkage having at least one change that is structurally distinguishable from a naturally-occurring internucleoside linkage. Modified internucleoside linkages may help to improve the stability of the inhibitory agents to nucleases and enhance cellular uptake.

Examples of modified internucleoside linkages include, but are not limited to, a phosphorothioate linkage, a phosphorodithioate linkage, a phosphoramidate linkage, a phosphorodiamidate linkage, a thiophosphoramidate linkage, a thiophosphorodiamidate linkage, a phosphoramidate morpholino linkage, and a thiophosphoramidate morpholino linkage, and a thiophosphorodiamidate morpholino linkage, which are known in the art and described in, e.g., Bennett and Swayze, *Annu Rev Pharmacol Toxicol.* 50:259-293, 2010. A phosphorothioate linkage is a 3' to 5' phosphodiester linkage that has a sulfur atom for a non-bridging oxygen in the phosphate backbone of an oligonucleotide. A phosphorodithioate linkage is a 3' to 5' phosphodiester linkage that has two sulfur atoms for non-bridging oxygens in the phosphate backbone of an oligonucleotide. A thiophosphoramidate linkage refers to a 3' to 5' phospho-linkage that has a sulfur atom for a non-bridging oxygen and a NH group as the 3'-bridging oxygen in the phosphate backbone of an oligonucleotide. In some embodiments, an inhibitory agent described herein has at least one phosphorothioate linkage. In some embodiments, all of the internucleoside linkages in an inhibitory agent described herein are phosphorothioate linkages.

Specifically, an inhibitory agent that inhibits or reduces the expression of a GAPLINC RNA (e.g., a GAPLINC RNA having the sequence of SEQ ID NO:1 or 2) can be an ASO that includes one or more modified nucleotides. An ASO comprising a sequence having at least 90% (e.g., 92%, 94%, 96%, 98%, or 100%) identity to a sequence of any one of SEQ ID NOS:3-7 can include one or more modified nucleotides. For example, an ASO comprising a sequence of any one of SEQ ID NOS:3-7 can include at least one (e.g., two, three, four, five, six, seven, eight, nine, or ten) modified nucleotide that has a modified sugar, such as a sugar having a 2'-OMe. In certain embodiments, the first five nucleotides from the 5' terminus of an ASO comprising a sequence of any one of SEQ ID NOS:3-7 each has a modified sugar having a 2'-OMe. In certain embodiments, the last five nucleotides from the 5' terminus of an ASO comprising a sequence of any one of SEQ ID NOS:3-7 each has a modified sugar having a 2'-OMe. In certain embodiments, the first and last five nucleotides from the 5' terminus of an ASO comprising a sequence of any one of SEQ ID NOS:3-7 each has a modified sugar having a 2'-OMe. An ASO comprising a sequence having at least 90% (e.g., 92%, 94%, 96%, 98%, or 100%) identity to a sequence of any one of SEQ ID NOS:3-7 can also include one or more modified internucleoside linkages. In certain embodiments, at least 10% (e.g., 15%, 20%, 25%, 30%, 35%, 40%, 45%, or 50%) of the internucleoside linkages in an ASO comprising a sequence of any one of SEQ ID NOS:3-7 are modified internucleoside linkages (e.g., phosphorothioate linkages). In certain embodiments, all of the internucleoside linkages in an ASO comprising a sequence of any one of SEQ ID NOS:3-7 are modified internucleoside linkages (e.g., phosphorothioate linkages).

IV. Detecting Expression Levels of Long Noncoding RNAs

Techniques and methods for measuring the expression levels of genes (e.g., lncRNAs) are available in the art. For example, detection and/or quantification of lncRNAs, such as a GAPLINC RNA (e.g., a GAPLINC RNA having a sequence of SEQ ID NO:1 or 2), may be accomplished by any one of a number methods or assays employing recombinant DNA or RNA technologies known in the art, including but not limited to, polymerase chain reaction (PCR), reverse transcription PCR (RT-PCR), microarrays, Northern blot, serial analysis of gene expression (SAGE), immunoassay, hybridization capture, cDNA sequencing, direct RNA sequencing, nanopore sequencing, and mass spectrometry.

In some embodiments, hybridization capture methods may be used for detection and/or quantification of lncRNAs. Some examples of hybridization capture methods include, e.g., capture hybridization analysis of RNA targets (CHART), chromatin isolation by RNA purification (ChIRP), and RNA affinity purification (RAP). In general, cells and tissues expressing the RNA of interest can be cross-linked and solubilized by shearing. The RNA of interest can then be enriched using rationally designed biotin tagged inhibitory agents. The captured RNA complexes can then be rinsed and eluted. The eluted material can be analyzed for the molecules of interest. The associated RNAs are commonly analyzed with qPCR or high throughput sequencing, and the recovered proteins can be analyzed with Western blots or mass spectrometry. General techniques for performing hybridization capture methods are described in the art and can be found in, e.g., Machyna and Simon, *Briefings in Functional Genomics* 17(2):96-103, 2018, which is incorporated herein by reference in its entirety. Further, Li et al, *JCI Insight.* 3(7):e98942, 2018 also describes methods of studying RNA (e.g., extracellular RNA) and is incorporated herein by reference in its entirety.

In some embodiments, microarrays may be used to measure the expression levels of lncRNAs. An advantage of microarray analysis is that the expression of each of the lncRNAs can be measured simultaneously, and microarrays can be specifically designed to provide a diagnostic expression profile for a particular disease or condition (e.g., an inflammatory disease). Microarrays may be prepared by selecting probes which comprise a polynucleotide sequence, and then immobilizing such probes to a solid support or surface. For example, the probes may comprise DNA sequences, RNA sequences, or copolymer sequences of DNA and RNA. The polynucleotide sequences of the probes may also comprise DNA and/or RNA analogues, or combinations thereof. For example, the polynucleotide sequences of the probes may be full or partial fragments of genomic nucleic acids. The polynucleotide sequences of the probes may also be synthesized nucleotide sequences, such as synthetic oligonucleotide sequences. Probes may be immobilized to a solid support which may be either porous or non-porous. For example, the probes may be polynucleotide sequences which are attached to a nitrocellulose or nylon membrane or filter covalently at either the 3' or the 5' end of the polynucleotide. Such hybridization probes are well-known in the art (see, e.g., Sambrook, et al., *Molecular Cloning: A Laboratory Manual*, 3rd Ed., 2001). In one embodiment, a microarray may include a support or surface with an ordered array of binding (e.g., hybridization) sites or "probes" each representing one of the lncRNAs described herein. More specifically, each probe of the array may be located at a known, predetermined position on the solid support such that the identity (e.g., the sequence) of each probe can be determined from its position in the array (e.g., on the support or surface). Each probe may be covalently attached to the solid support at a single site.

Quantitative reverse transcriptase PCR (qRT-PCR) can also be used to determine the expression profiles of lncRNAs. The first step in gene expression profiling by RT-PCR is the reverse transcription of the RNA template into cDNA, followed by its exponential amplification in a PCR reaction. The two most commonly used reverse transcriptases are avilo myeloblastosis virus reverse transcriptase (AMY-RT) and Moloney murine leukemia virus reverse transcriptase (MLVRT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction. Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN PCR typically utilizes the 5'-nuclease activity of Taq polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, may be designed to detect nucleotide sequence located between the two PCR primers. The probe is non-extendible by Taq DNA polymerase enzyme, and may be labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

Serial Analysis Gene Expression (SAGE) can also be used to determine RNA (e.g., lncRNA) expression level. SAGE analysis does not require a special device for detection, and may be used for simultaneously detecting the expression of a large number of transcription products. First, RNA is extracted, converted into cDNA using a biotinylated oligo (dT) primer, and treated with a four-base recognizing restriction enzyme (Anchoring Enzyme: AE) resulting in AE-treated fragments containing a biotin group at their 3' terminus. Next, the AE-treated fragments are incubated with streptavidin for binding. The bound cDNA is divided into two fractions, and each fraction is then linked to a different double-stranded oligonucleotide adapter (linker) A or B. These linkers are composed of: (1) a protruding single strand portion having a sequence complementary to the sequence of the protruding portion formed by the action of the anchoring enzyme, (2) a 5' nucleotide recognizing sequence of the ITS-type restriction enzyme (cleaves at a predetermined location no more than 20 bp away from the recognition site) serving as a tagging enzyme (TE), and (3) an additional sequence of sufficient length for constructing a PCR-specific primer. The linker-linked cDNA is cleaved using the tagging enzyme, and only the linker-linked cDNA sequence portion remains, which is present in the form of a short-strand sequence tag. Next, pools of short-strand sequence tags from the two different types of linkers are linked to each other, followed by PCR amplification using primers specific to linkers A and B. As a result, the amplification product is obtained as a mixture comprising myriad sequences of two adjacent sequence tags (ditags) bound to linkers A and B. The amplification product is treated with the anchoring enzyme, and the free ditag portions are linked into strands in a standard linkage reaction. The amplification product is then cloned. Determination of the clone's nucleotide sequence can be used to obtain a readout of consecutive ditags of constant length. The presence of lncRNA corresponding to each tag can then be identified from the nucleotide sequence of the clone and information on the sequence tags.

One of skill in the art, when provided with the set of lncRNAs to be identified and quantified, will be capable of selecting the appropriate assay for performing the methods disclosed herein.

V. Pharmaceutical Compositions and Preparations

The disclosure features pharmaceutical compositions that include an inhibitory agent described herein. In addition to the inhibitory agent, the pharmaceutical compositions may contain one or more pharmaceutically acceptable carriers or excipients, which can be formulated by methods known to those skilled in the art. In some embodiments, a pharmaceutical composition of the disclosure includes an inhibitory agent in a therapeutically effective amount. In certain embodiments, the therapeutically effective amount of the inhibitory agent is sufficient to prevent, alleviate, or ameliorate symptoms of a disease (e.g., an inflammatory disease) or to prolong the survival of the subject being treated. Determination of a therapeutically effective amount is within the capability of those skilled in the art.

Inhibitory agents may be mixed with pharmaceutically acceptable active and/or inert substances for the preparation of pharmaceutical compositions. Compositions and methods for the formulation of pharmaceutical compositions are dependent upon a number of criteria, including, but not limited to, route of administration, extent of disease, or dose to be administered. An inhibitory agent targeted to a GAPLINC RNA (e.g., a GAPLINC RNA having a sequence of SEQ ID NO:1 or 2) can be utilized in pharmaceutical compositions by combining the inhibitory agent with a suitable pharmaceutically acceptable diluent or carrier. A pharmaceutically acceptable diluent includes phosphate-buffered saline (PBS). PBS is a diluent suitable for use in compositions to be delivered parenterally. In some embodiments, a pharmaceutical composition includes an inhibitory agent described herein and a pharmaceutically acceptable diluent. In some embodiments, the pharmaceutically acceptable diluent is PBS.

Pharmaceutical compositions including inhibitory agents encompass any pharmaceutically acceptable salts or esters thereof, which, upon administration to a mammal (e.g., a human), is capable of providing (directly or indirectly) the biologically active form of the inhibitory agent. Accordingly, for example, the disclosure is also drawn to pharmaceutically acceptable salts of inhibitory agents, prodrugs, pharmaceutically acceptable salts of such prodrugs, and other bioequivalents. Suitable pharmaceutically acceptable salts include, but are not limited to, sodium and potassium salts. In some embodiments, a prodrug can include the incorporation of additional nucleosides or nucleotides at one or both ends of an inhibitory agent which are cleaved by endogenous nucleases within the body, to form the active inhibitory agent.

In some embodiments, pharmaceutical compositions of the disclosure include one or more oligonucleotides and one or more pharmaceutically acceptable carriers or excipients. Acceptable carriers and excipients in the pharmaceutical compositions are nontoxic to recipients at the dosages and concentrations employed. Acceptable carriers and excipients may include buffers such as phosphate, citrate, HEPES, and TAE, antioxidants such as ascorbic acid and methionine, preservatives such as hexamethonium chloride, octadecyldimethylbenzyl ammonium chloride, resorcinol, and benzalkonium chloride, proteins such as human serum albumin, gelatin, dextran, and immunoglobulins, hydrophilic polymers such as polyvinylpyrrolidone, amino acids such as glycine, glutamine, histidine, and lysine, and carbohydrates such as glucose, mannose, sucrose, and sorbitol. In some embodiments, carriers and excipients are selected from water, salt solutions, alcohol, polyethylene glycols, gelatin, lactose, amylase, magnesium stearate, talc, silicic acid, viscous paraffin, hydroxymethylcellulosem, and polyvinylpyrrolidone. In some embodiments, a pharmaceutical composition of the disclosure includes a co-solvent system. Examples of co-solvent systems include, but are not limited to, benzyl alcohol, a nonpolar surfactant, a water-miscible organic polymer, and an aqueous phase. In some embodiments, such co-solvent systems are used for hydrophobic compounds. A non-limiting example of such a co-solvent system is the VPD co-solvent system, which is a solution of absolute ethanol including 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In some embodiments, a pharmaceutical composition of the disclosure is prepared using known techniques, including, but not limited to mixing, dissolving, granulating, dragee-making, levigating, emulsifying, encapsulating, entrapping, and tabletting processes. In some embodiments, a pharmaceutical composition of the disclosure is a liquid (e.g., a suspension, elixir and/or solution). In some embodiments, a liquid pharmaceutical composition is prepared using ingredients known in the art, including, but not limited to, water, glycols, oils, alcohols, flavoring agents, preservatives, and coloring agents. In some embodiments, a pharmaceutical composition of the disclosure is a solid (e.g., a powder, tablet, and/or capsule). In some embodiments, a solid pharmaceutical composition including one or more oligonucleotides is prepared using ingredients known in the art, including, but not limited to, starches, sugars, diluents, granulating agents, lubricants, binders, and disintegrating agents. In certain embodiments, a pharmaceutical composition of the disclosure is formulated as a depot preparation. In general, depot preparations are typically longer acting than non-depot preparations. In some embodiments, such preparations are administered by implantation (for example subcutaneously or intramuscularly) or by intramuscular injection. In some embodiments, depot preparations are prepared using suitable polymeric or hydrophobic materials (for example an emulsion in an acceptable oil) or ion exchange resins, or as sparingly soluble derivatives, for example, as a sparingly soluble salt.

In some embodiments, a pharmaceutical composition of the disclosure includes a delivery system. Examples of delivery systems include, but are not limited to, exosomes, liposomes, and emulsions. In some embodiments, inhibitory agents described herein may be loaded or packaged in exosomes that specifically target a cell type, tissue, or organ to be treated. Exosomes are small membrane-bound vesicles of endocytic origin that are released into the extracellular environment following fusion of mutivesicular bodies with the plasma membrane. Exosome production has been described for many immune cells including B cells, T cells, and dendritic cells, Techniques used to load a therapeutic compound (e.g., an inhibitory agent described herein) into exosomes are known in the art and described in, e.g., U.S. Patent Publication Nos. US 20130053426 and US 20140348904, and International Patent Publication No. WO 2015002956, which are incorporated herein by reference. In some embodiments, therapeutic compounds may be loaded into exosomes by electroporation or the use of a transfection reagent (e.g., cationic liposomes). In some embodiments, an exosome-producing cell can be engineered to produce the exosome and load it with the therapeutic compound (e.g., an inhibitory agent described herein). For example, exosomes may be loaded by transforming or transfecting an exosome-producing host cell with a genetic construct that expresses the therapeutic compound (e.g., an inhibitory agent described herein), such that the therapeutic compound is taken up into the exosomes as the exosomes are produced by the host cell. In some embodiments, an exosome-targeted protein in the exosome-producing cell may bind (e.g., non-covalently) to the therapeutic compound. Various targeting moieties may be introduced into exosomes, so that the exosomes can be targeted to a selected cell type, tissue, or organ. Targeting moieties may bind to cell-surface receptors or other cell-surface proteins or peptides that are specific to the targeted cell type, tissue, or organ. In some embodiments, exosomes have a targeting moiety expressed on their surface. In some embodiments, the targeting moiety expressed on the surface of exosomes is fused to an exosomal transmembrane protein. Techniques of introducing targeting moieties to exosomes are known in the art and described in, e.g., U.S. Patent Publication Nos. US 20130053426 and US 20140348904, and International Patent Publication No. WO 2015002956, which are incorporated herein by reference.

Certain delivery systems are useful for preparing certain pharmaceutical compositions including those including hydrophobic compounds. In some embodiments, certain organic solvents such as dimethylsulfoxide are used. In some embodiments, a pharmaceutical composition of the disclosure includes one or more tissue-specific delivery molecules designed to deliver the one or more pharmaceutical agents of the disclosure to specific tissues or cell types. For example, in certain embodiments, pharmaceutical compositions include liposomes coated with a tissue-specific antibody. In some embodiments, a pharmaceutical composition of the disclosure includes a sustained-release system. A non-limiting example of such a sustained-release system is a semi-permeable matrix of solid hydrophobic polymers. In some embodiments, sustained-release systems may, depending on their chemical nature, release pharmaceutical agents over a period of hours, days, weeks or months.

In some embodiments, a pharmaceutical agent is a sterile lyophilized inhibitory agent that is reconstituted with a suitable diluent, e.g., sterile water for injection. The reconstituted product is administered as a subcutaneous injection or as an intravenous infusion after dilution into saline. In some embodiments, the lyophilized drug product consists of the inhibitory agent which has been prepared in water for injection, adjusted to pH 7.0-9.0 with acid or base during preparation, and then lyophilized. The lyophilized inhibitory agent may be 5-800 mg of the inhibitory agent. It is understood that this encompasses 5, 10, 15, 20, 25, 50, 75, 100, 125, 150, 175, 200, 225, 250, 275, 300, 325, 350, 375, 425, 450, 475, 500, 525, 550, 575, 600, 625, 650, 675, 700, 725, 750, 775, and 800 mg of lyophilized inhibitory agent. The lyophilized drug product may be packaged in a 2 mL Type I, clear glass vial (ammonium sulfate-treated), stoppered with a bromobutyl rubber closure and sealed with an aluminum FLIP-OFF® overseal.

In some embodiments, a pharmaceutical composition is prepared for gene therapy. In some embodiments, the pharmaceutical composition for gene therapy is in an acceptable diluent, or includes a slow release matrix in which the gene delivery vehicle is imbedded. Vectors that may be used as in vivo gene delivery vehicle include, but are not limited to, retroviral vectors, adenoviral vectors, poxviral vectors (e.g., vaccinia viral vectors, such as Modified Vaccinia Ankara), adeno-associated viral vectors, and alphaviral vectors.

In some embodiments, a pharmaceutical composition of the disclosure is prepared for oral administration. In some embodiments, a pharmaceutical composition is formulated by combining one or more inhibitory agents with one or more pharmaceutically acceptable carriers and excipients. Certain of such carriers and excipients enable pharmaceutical compositions to be formulated as tablets, pills, dragees, capsules, liquids, gels, syrups, slurries, and suspensions, for oral ingestion by a subject. In some embodiments, pharmaceutical compositions for oral use are obtained by mixing oligonucleotide and one or more solid excipients. Suitable carriers and excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In some embodiments, such a mixture is optionally ground and auxiliaries are optionally added. In some embodiments, pharmaceutical compositions are formed to obtain tablets or dragee cores. In some embodiments, disintegrating agents (e.g., cross-linked polyvinyl pyrrolidone, agar, or alginic acid or a salt thereof, such as sodium alginate) are added.

In some embodiments, a pharmaceutical composition is prepared for administration by injection (e.g., intravenous, subcutaneous, intramuscular, etc.). In some embodiments, a pharmaceutical composition includes a carrier and is formulated in aqueous solution, such as water or physiologically compatible buffers such as PBS, Hank's solution, Ringer's solution, or physiological saline buffer. Examples of solvents suitable for use in pharmaceutical compositions for injection include, but are not limited to, lipophilic solvents and fatty oils, such as sesame oil, and synthetic fatty acid esters, such as ethyl oleate or triglycerides. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In some embodiments, a pharmaceutical composition is prepared for topical administration. Certain of such pharmaceutical compositions include bland moisturizing bases, such as ointments or creams. Exemplary suitable ointment bases include, but are not limited to, petrolatum, petrolatum plus volatile silicones, lanolin, and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP), and Lubriderm™, available from Pfizer (Morris Plains, N.J.).

VI. Methods

The methods of the disclosure include treating an inflammatory disease in a subject by administering to the subject a therapeutically effective amount of an inhibitory agent described herein, in which the inhibitory agent inhibits the expression of a GAPLINC RNA, such as a GAPLINC RNA having the sequence of SEQ ID NO:1 or 2.

An inhibitory agent that can be used to treat an inflammatory disease can have a sequence having at least 90% (e.g., 92%, 94%, 96%, 98%, or 100%) identity to a sequence of any one of SEQ ID NOS:3-7. In other embodiments, an inhibitory agent can be a double-stranded siRNA comprising a sense region and antisense region. An antisense region in an siRNA can have a sequence having at least 90% (e.g., 92%, 94%, 96%, 98%, or 100%) identity to a sequence of any one of SEQ ID NOS:9, 11, 13, 15, 17, and 19. A sense region in an siRNA can have a sequence having at least 90% (e.g., 92%, 94%, 96%, 98%, or 100%) identity to a sequence of any one of SEQ ID NOS:8, 10, 12, 14, 16, and 18. An inhibitory agent used in methods for treating an inflammatory disease described herein can have one or more modified nucleotides. For example, an inhibitory agent can have one or more modified sugars, such as a modified sugar having a 2'-OMe. An inhibitory agent can also have one or more modified internucleoside linkages, such as a phosphorothioate linkage.

Examples of inflammatory diseases that can be treated using an inhibitory agent described herein include, but are not limited to, sepsis, multiple sclerosis, rheumatoid arthritis, intestinal bowel disease, and systemic lupus erythematosus. Other examples of inflammatory diseases that can be treated using an inhibitory agent described herein include, but are not limited to, ANCA-associated vasculitis, antiphospholipid antibody syndrome, autoimmune hemolytic anemia, chronic inflammatory demyelinating neuropathy, dermatomyositis, Goodpasture's Syndrome, organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease, idiopathic thrombocytopenia purpura, Myasthenia Gravis, neuromyelitis optica, pemphigus and other autoimmune blistering disorders, Sjogren's Syndrome, autoimmune cytopenias and other disorders mediated through antibody-dependent phagocytosis, and other FcR-dependent inflammatory syndromes, e.g., synovitis, dermatomyositis, systemic vasculitis, and glomerulitis or vasculitis.

Methods of the disclosure also include inhibiting or reducing the expression of a GAPLINC RNA (e.g., a GAPLINC RNA having the sequence of SEQ ID NO:1 or 2) in a subject by administering to the subject a therapeutically effective amount of an inhibitory agent described herein, in which the inhibitory agent inhibits or reduces the expression of the GAPLINC RNA.

EXAMPLES

Example 1—Experimental Methods

ASO design: ASOs were designed and chemically synthesized by IDT to target multiple isoforms of GAPLINC. For the experiments, ASOs that include the 2'OMe/PS modification to prevent these molecules from acting as a ligand and activating the inflammatory response were used.

Cell culture and transfections: THP-1 CRISPR/Cas9 Synergistic Activation Mediator (SAM) GAPLINC-activated cells were cultured in RPMI media containing 10% fetal calf serum. GAPLINC ASO1, ASO2, and ASO4 were transfected in 96-well plate format using 0.5 µL Lipofectamine® 2000 in OptiMEM® I for a total volume of 50 µL in each well. THP-1 SAM GAPLINC-activated cells were plated in 100 µL Dulbecco's Modified Essential Medium (DMEM) for a total of 20,000 cells/well, added to the lipid-oligonucleotide complexes, then incubated for 24 h at 37° C. and 5% $CO_2$.

RNA isolation and qPCR: GAPLINC knockdown was measured by quantitative PCR (qPCR). RNA was isolated 24 h after transfection with the Direct-zol™ RNA MiniPrep Kit (Zymo Research). cDNA was synthesized from total RNA using the iScript Select cDNA synthesis kit (Bio-Rad). LncRNA knockdown levels were calculated by comparing levels of GAPLINC in GAPLINC ASO-transfected cells to negative control oligonucleotides.

Cell culture and transfections: Patient blood samples (n=4) were obtained from the Stanford Blood Center. Peripheral blood mononuclear cells (PBMCs) were isolated using a Ficoll gradient. Cells were cultured in RPMI containing 10% fetal calf serum (FCS) supplemented with penicillin/streptomycin. PBMCs were differentiated using 50 ng/mL recombinant macrophage colony-stimulating factor (MCSF). 25 picomoles of GAPLINC-targeting and non-targeting siRNA were transfected in 12-well plate format using 1 µL Lipofectamine® 2000 in OptiMEM® I for a total volume of 50 µL in each well. Human PBMCs that were differentiated for two days in MCSF in DMEM were added to the lipid-siRNA complexes, then incubated at 37° C. and 5% $CO_2$.

RNA isolation and qPCR: RNA was isolated 72 h after siRNA transfection with the Direct-zol™ RNA MiniPrep Kit (Zymo Research). cDNA was synthesized from total RNA using the iScript Select cDNA synthesis kit (Bio-Rad). LncRNA knockdown levels were calculated by comparing levels of GAPLINC in GAPLINC siRNA-transfected cells to non-targeting siRNA.

RNA sequencing: For generation of RNA-Sequencing libraries, RNA was isolated as described above and the RNA integrity was tested with a FragmentAnalyzer (Advanced Analytical). RNA-Sequencing libraries were prepared with TruSeq stranded RNA sample preparation kits (Illumina), depletion of ribosomal RNA was performed by positive selection of polyA+RNA. Sequencing was performed on Illumina HighSeq. RNA-seq 50 bp reads were aligned to the human genome using STAR. Differential gene expression specific analyses were conducted with the DESeq R package.

Example 2—Identification and Characterization of Macrophage-Specific LncRNA GAPLINC Sepsis is a life-threatening illness caused by an overreaction of the body to the presence of infection, which can rapidly lead to multi-organ failure and death. The immune system is essential in providing protection against infection; however uncontrolled activation can have serious consequences to the host. According to the CDC, 1 in 3 patients who die in a hospital have sepsis[5] and yet we still do not understand the underlying molecular mechanisms that lead to fatality. Clinical options for the treatment of sepsis are limited to the delivery of fluid, antibiotics, and supportive care, and have remained largely unchanged for decades. Though early diagnoses and rapid treatment have improved sepsis outcomes[6], there is a critical need to develop new therapies. Although gene expression studies have been performed to examine potential therapeutic targets for sepsis, these targets remain largely uncharacterized[7]. We have identified a long noncoding RNA (lncRNA) with roles in controlling the immune response and endotoxic shock that provide new avenues for novel drug development to target sepsis.

As lncRNA expression can regulate the immune response by affecting immune cell differentiation and their respective function[8,9,10,11], we wanted to investigate the role of lncRNAs in macrophages. Macrophages are important innate immune cells that can be derived from monocytes and are critical for pathogen recognition through the use of Toll-like receptors (TLRs). Upon activation, TLRs initiate complex signaling pathways that activate key transcription factors such as NF-κB, leading to the transcription of hundreds of immune response genes[12].

Figure 1:
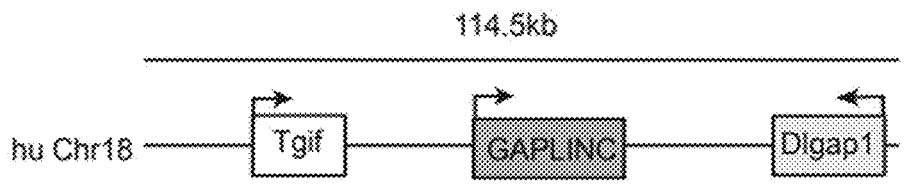
FIG. 1 is an illustration of the GAPLINC locus. GAPLINC is located on chromosome 18 between the protein-coding genes Tgif and Dlgap1.
Figure 2:
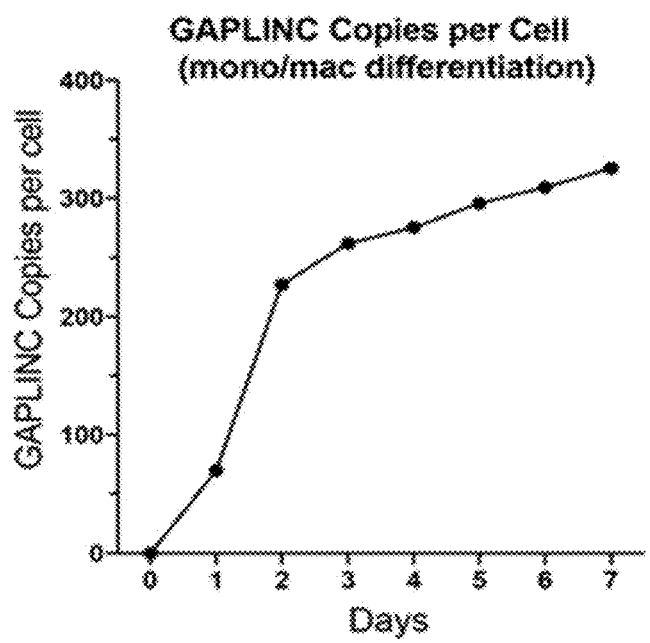
FIG. 2 is a plot showing that GAPLINC expression is induced during macrophage differentiation. The plot shows GAPLINC expression following monocyte to macrophage differentiation. Data is obtained from RNA-seq and represented as copies of GAPLINC per cell (FPKM).

To identify lncRNAs involved in macrophage differentiation and function, we conducted RNA-sequencing (RNA-Seq) in both human primary monocyte-derived macrophages (MDMs) and the monocytic cell line THP-1s (FIG. 12A). We identified GAPLINC as the most unregulated lncRNA during monocyte to macrophage differentiation (FIG. 12B). GAPLINC levels were detectable by Day 1 and increased to ~300 copies per cell (FIG. 2). Using RNA profiling technology (nCounter, Nanostring), we validated GAPLINC as one of the top ten mRNAs expressed in differentiated primary MDMs and THP1s (FIG. 12C). We also confirmed that GAPLINC is highly expressed in MDMs but not expressed in the closely related cell type monocyte-derived dendritic cells (FIG. 12D), suggesting that expression of GAPLINC is cell-type specific. By performing a cell fractionation experiment and measuring GAPLINC levels in the cytoplasmic and nuclear compartments of macrophages using quantitative PCR (qPCR), we found GAPLINC is predominantly localized in the cytosol when compared to CD14, a cytoplasmic mRNA, and NEAT1, a nuclear lncRNA (FIG. 12E). This is consistent with findings in cancer cells in which GAPLINC is mainly localized to the cytoplasm13. To ensure GAPLINC is noncoding, we performed polysome profiling, a method used to analyze if a gene is actively translated into protein. In contrast to CD14, neither NEAT1 or GAPLINC were found in the high polysome fraction, suggesting that GAPLINC is not translated (FIG. 12F).

Example 3—Effect of GAPLINC Silencing on Differentiating Macrophages

Figure 4A:
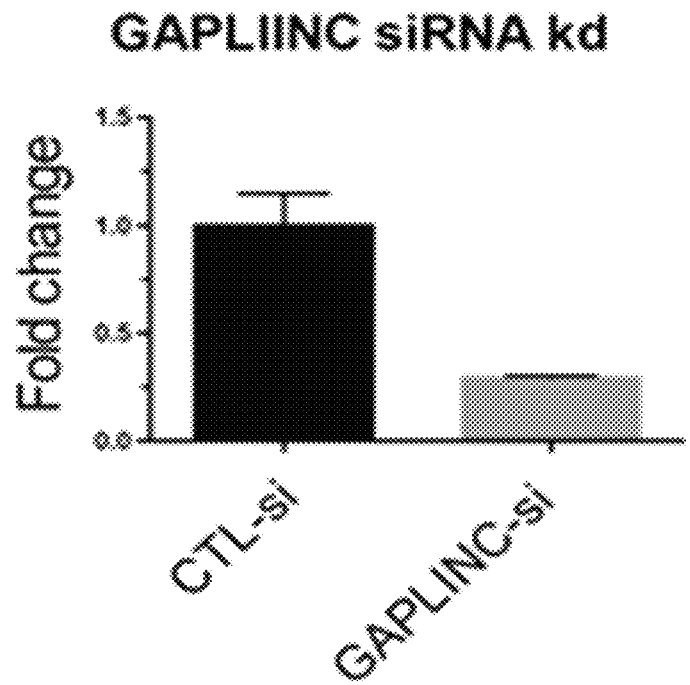
FIGS. 4A-4C collectively show that knockdown of GAPLINC in primary human monocyte-derived macrophages (MDMs) results in greater expression of inflammatory genes.
Figure 4B:
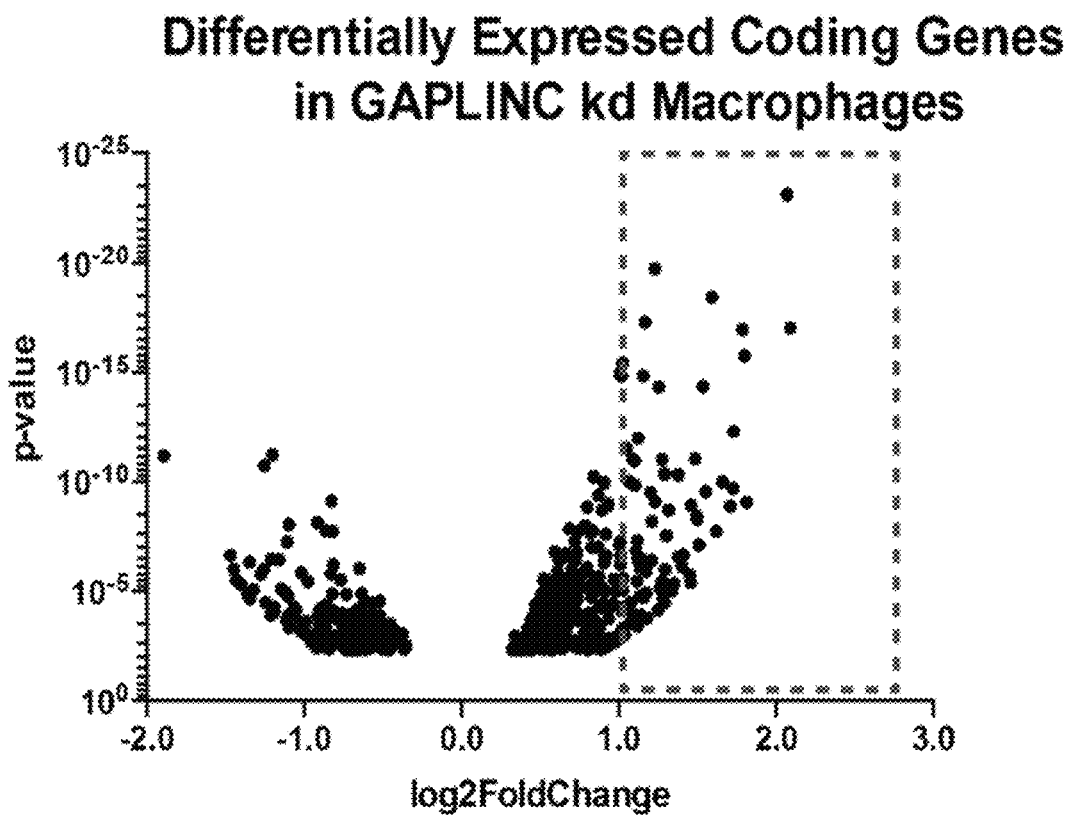
Figure 4C:
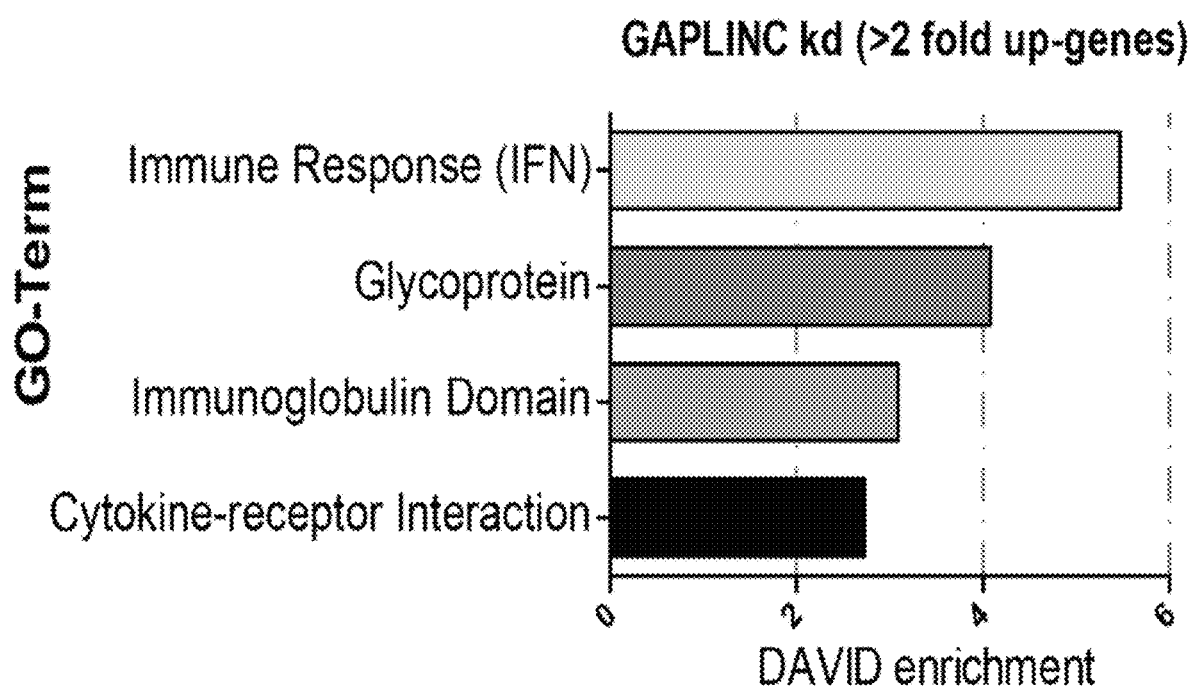
Figure 5A:
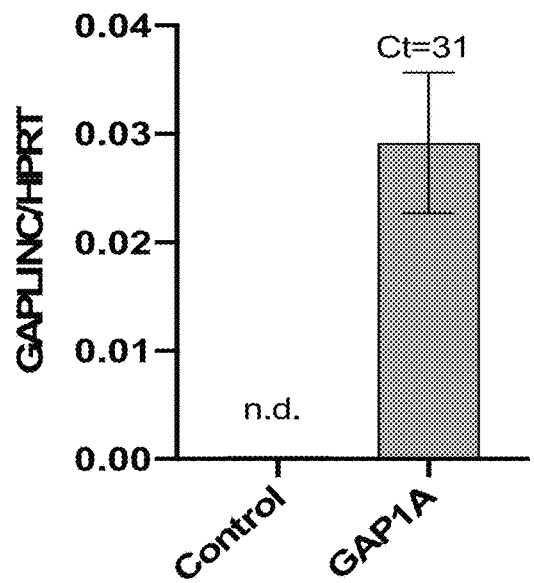
FIG. 5A is a bar graph showing GAPLINC expression in Human THP-1 SAM GAPLINC-activated MDMs.
Figure 5B:
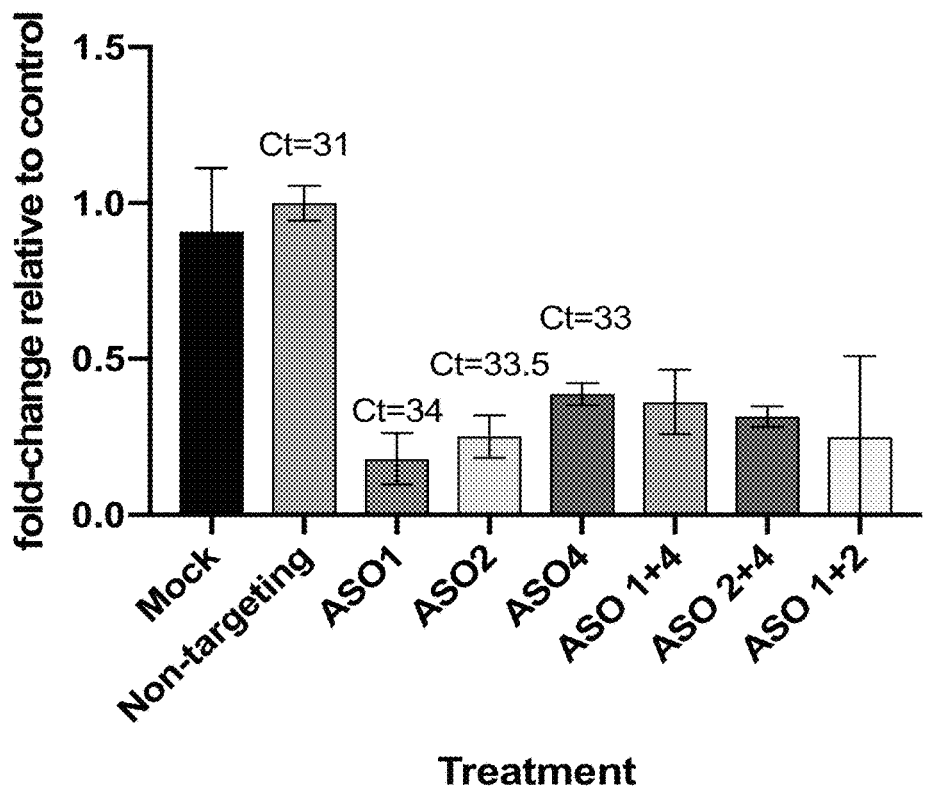
FIG. 5B is a bar graph showing GAPLINC expression in in Human THP-1 SAM GAPLINC-activated MDMs treated with the indicated ASOs. GAPLINC expression was measured by qPCR 24 hours after transfection of the ASOs.
Figure 6:
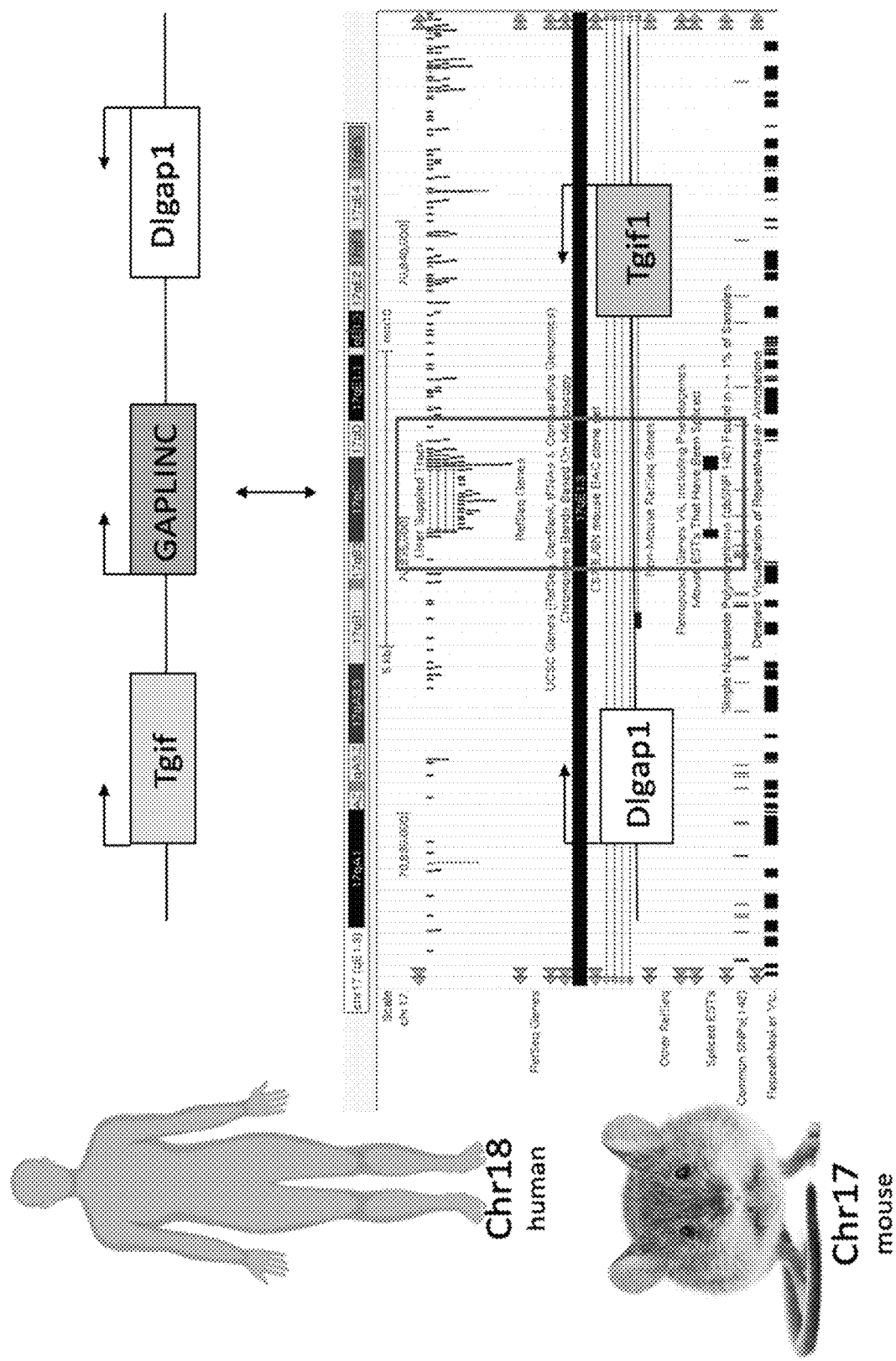
FIG. 6 is a UCSC Genome Browser™ representation detailing the syntenic loci for GAPLINC. RNA-seq reads suggest the presence of a transcript in mouse between the same two protein coding genes found in human. The locus in mouse is inverted relative to human.

Next, we investigated the effect of GAPLINC silencing on differentiating macrophages. As GAPLINC levels increase during differentiation, we hypothesized that GAPLINC knockdown would impact genes involved in differentiation. Using pooled siRNA, we achieved approximately 55-65% knockdown of GAPLINC in primary MDMs (FIGS. 13A and 13B). We performed RNA-Seq and identified a number of genes that were dysregulated upon GAPLINC knockdown (FIG. 4B). We confirmed the top hits using Nanostring (FIG. 15). Gene Ontology (GO) enrichment analysis showed that immune response genes were significantly overrepresented in genes unregulated upon GAPLINC knockdown, and not genes involved in macrophage differentiation, contrary to our original hypothesis. (FIG. 14A). Notably, differentially expressed genes in GAPLINC knockdown cells include proinflammatory cytokines and chemokines (IL6, CXCL10, TNFSF10), IFN-stimulated genes (ISGs) (IFIT2, RSAD2) and guanylate-binding proteins (GBPs) (GBP3, GBP5) (FIG. 14B). To verify that macrophage differentiation was unaffected by GAPLINC knockdown, levels of CD11B, CD16 and CD14 were measured in control and siGAPLINC-treated macrophages and found to be similar.

As GAPLINC knockdown resulted in the upregulation of immune response genes, we generated a THP-1 cell line overexpressing GAPLINC to determine if it mediates the opposite effect. Using long-read sequencing data, we identified the dominant isoforms of GAPLINC expressed in MDMs (FIG. 14C). The most abundant isoform, which matches the RefSeq gene annotation, was incorporated into our construct (FIG. 14D). We utilized a lentiviral vector containing a bidirectional promoter to drive GFP/Zeocin and GAPLINC in parallel (FIG. 14E). We confirmed using qPCR that GAPLINC was stably expressed in THP-1s compared to control (FIG. 14F). Overexpression of GAPLINC attenuated IL6 induction at the RNA level upon stimulation with lipopolysaccharide (LPS), a component of gram negative bacteria (FIG. 14G). These observations suggest that GAPLINC acts as a negative regulator of the inflammatory response.

Figure 3:
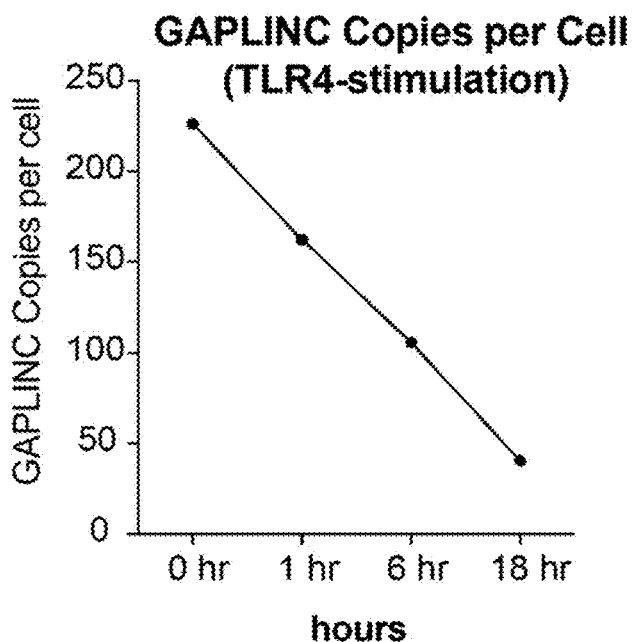
FIG. 3 is a plot showing that GAPLINC is downregulated following inflammatory stimulation. RNA-seq was performed on primary human macrophages stimulated with 200 ng/mL LPS for the indicated time points. GAPLINC expression is represented as copies per cell.

Next, we examined GAPLINC levels in primary MDMs in response to inflammation. Upon LPS stimulation, we found that GAPLINC is rapidly downregulated (FIG. 3). Additionally, using qPCR we show that GAPLINC is also downregulated following activation with a variety of TLR ligands (FIG. 16A). Induction of positive control inflammatory genes TNFα, IL6, and CCL5 was confirmed (FIGS. 16B-16D). This data suggests that GAPLINC expression must be reduced following stimulation in order for optimal inflammatory gene induction to occur. To evaluate the role of NF-κB in controlling the expression of GAPLINC, MDMs were pretreated with DMSO or BAY11-7082, an NF-κB inhibitor, followed by stimulation with LPS for 6 h. In BAY11-7082-treated MDMs, the downregulation of GAPLINC was impaired relative to control (FIG. 2H), which suggests the regulation of GAPLINC is dependent on NF-κB signaling. Induction of positive control inflammatory genes TNF-α and IL6 upon LPS stimulation was confirmed (FIGS. 16E and 16F). To understand how GAPLINC is being regulated, we utilized ATAC-seq in MDMs to assess chromatin accessibility of the GAPLINC locus. We found that GAPLINC is actively transcribed in resting macrophages, but tightly shut down following LPS stimulation (FIG. 14I), suggesting that GAPLINC is regulated at the level of transcription.

Example 4—Conservation of GAPLINC Between Human and Mouse

Figure 7:
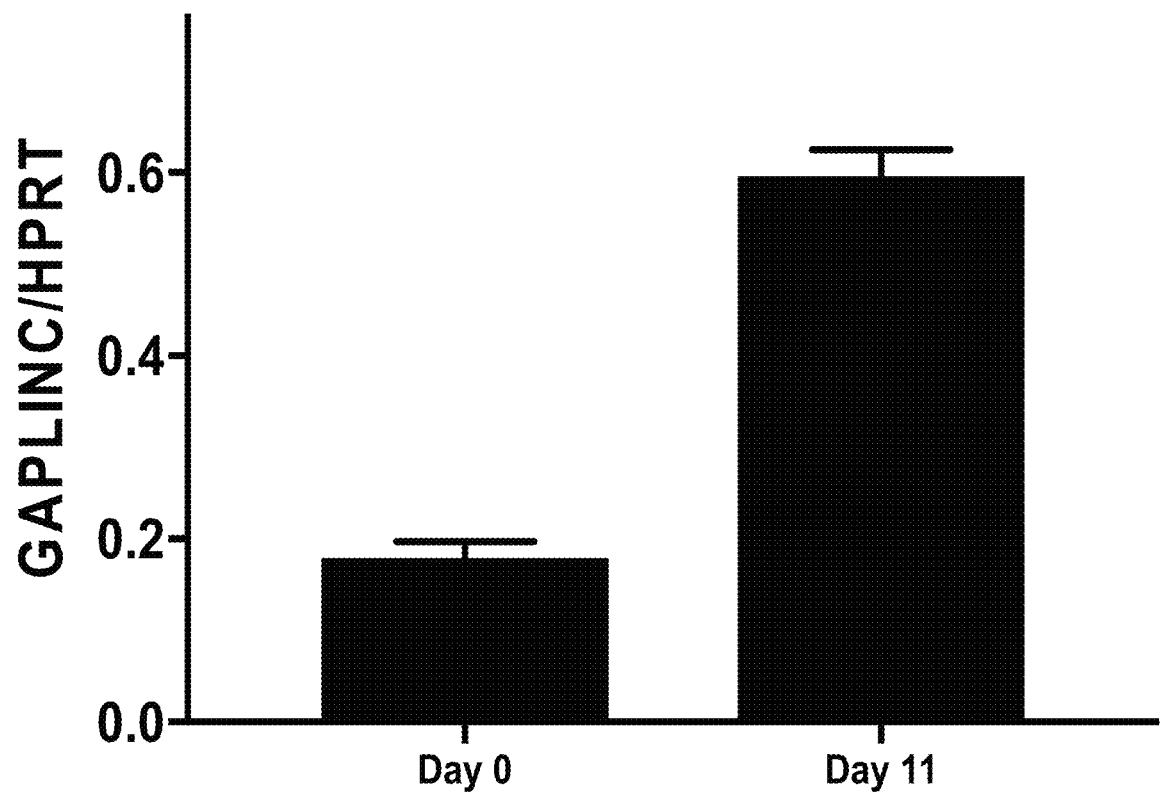
FIG. 7 is a bar graph showing that GAPLINC is highly induced during macrophage differentiation in mouse bone marrow derived macrophages (BMDMs). The bars show GAPLINC expression following macrophage differentiation from undifferentiated bone marrow cells. Data is obtained from qPCR and normalized to HPRT.
Figure 8:
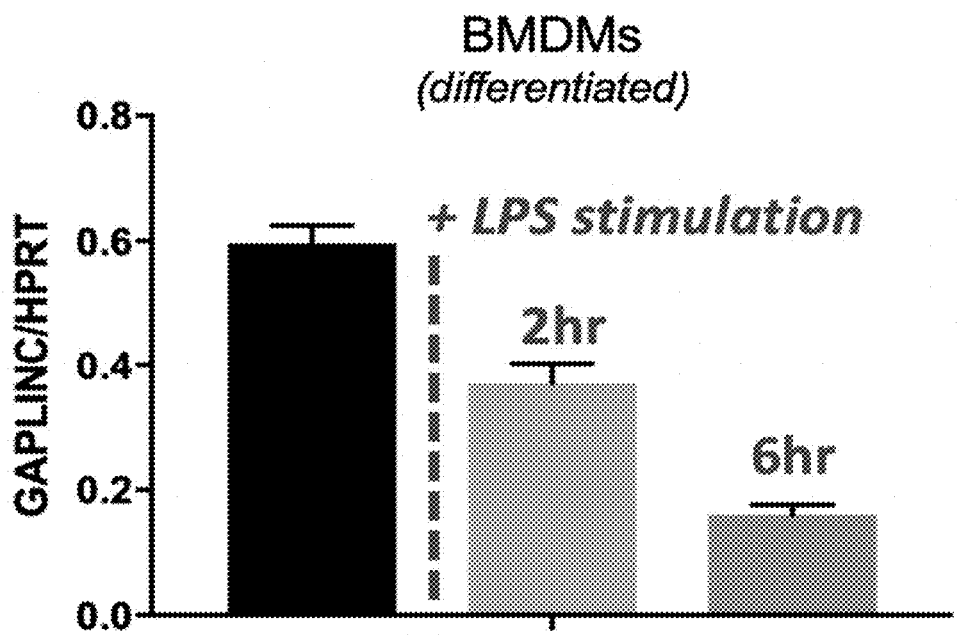
FIG. 8 is a bar graph showing that murine GAPLINC expression is reduced following LPS stimulation. Bone marrow derived macrophages were stimulated with 200 ng/mL LPS. GAPLINC expression was measured using qPCR and normalized to HPRT.

To explore the conservation of GAPLINC between human and mouse, we sought to identify syntenic loci, in which genes are positionally conserved between the same two protein-coding genes, followed by an assessment for functional conservation. Here we show that Gaplinc is positionally conserved, locating a transcript between genes Dlgap1 and Tgif1 (FIG. 17A). To confirm cell-type specificity, we utilized the Mouse Cell Atlas14 to assess transcript levels across immune cells in the bone marrow and found it highest expressed in macrophages, with lower levels of expression in neutrophil progenitors (FIG. 17B). Next, to determine if expression patterns were conserved during macrophage differentiation in both human and mouse, we performed RNA-seq comparing bone marrow cells to bone marrow derived macrophages (BMDMs), completed de novo transcript assembly and found mouse Gaplinc levels increased following differentiation (FIG. 18A). We validated this by qPCR comparing Gaplinc levels in bone marrow cells to BMDMs (FIG. 7). Comparable to human GAPLINC, mouse Gaplinc is rapidly downregulated in LPS-stimulated BMDMS (FIG. 8). As a control, we confirmed the induction of inflammatory genes Tnf-α and 116 (FIG. 18B). Mouse Gaplinc is also rapidly downregulated following activation with various TLR ligands. Induction of the positive control genes 116 and Cc15 was also confirmed (FIG. 18C).

Figure 9A:
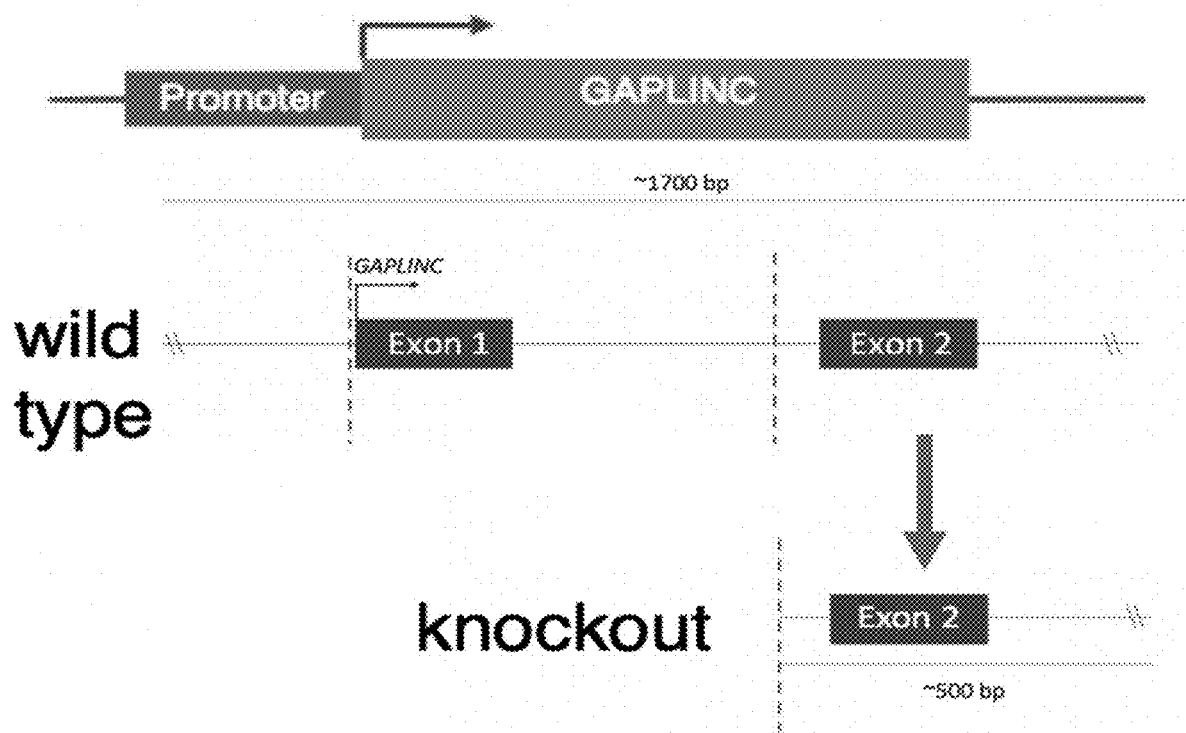
FIGS. 9A-9D summarize RNA-seq experiments comparing wild-type and GAPLINC−/− macrophages.
Figure 9B:
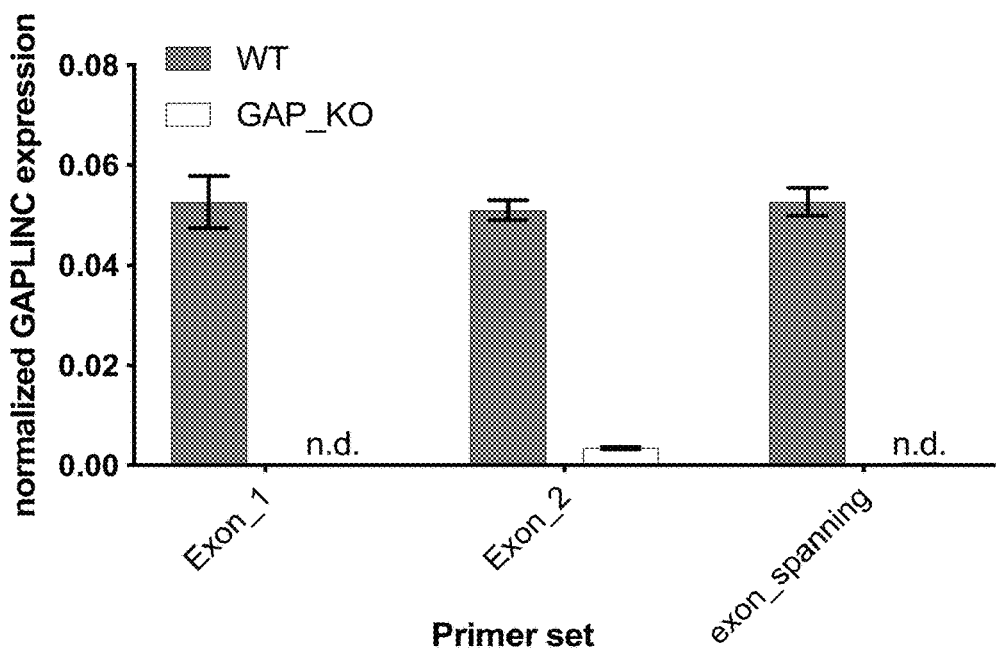
Figure 9C:
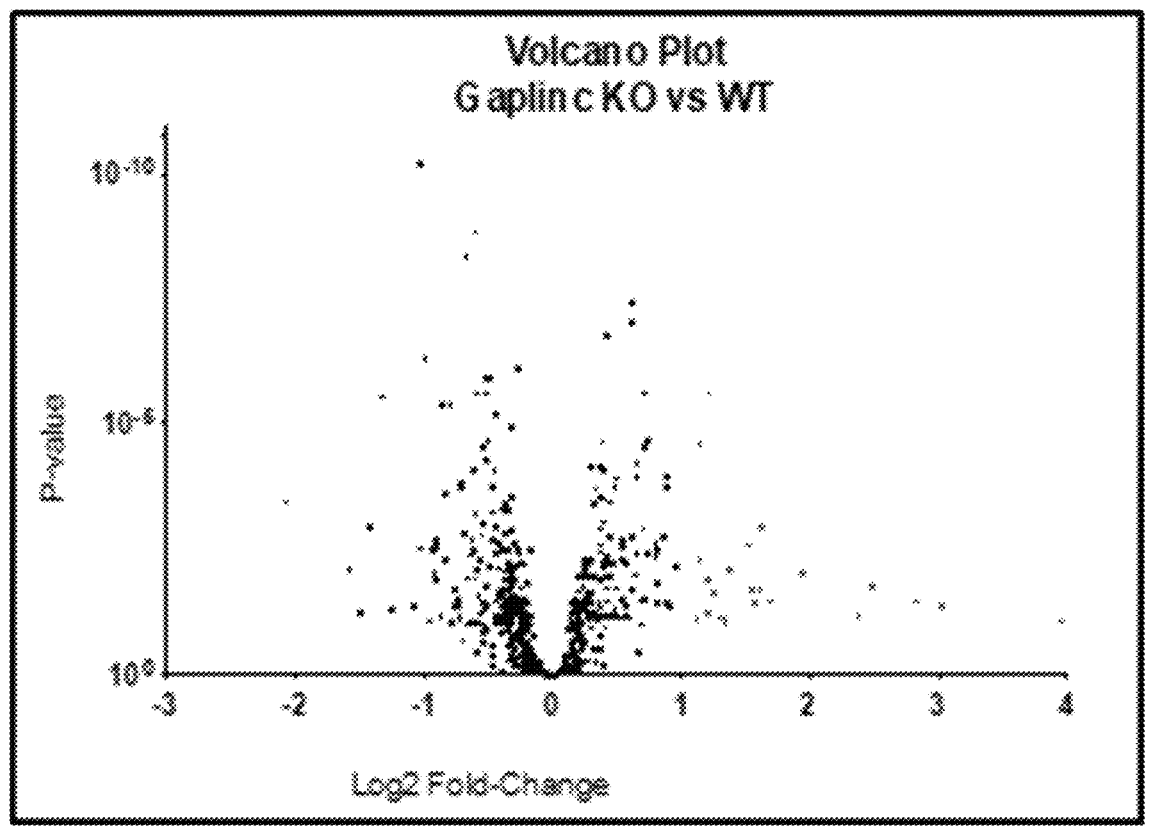
Figure 9D:
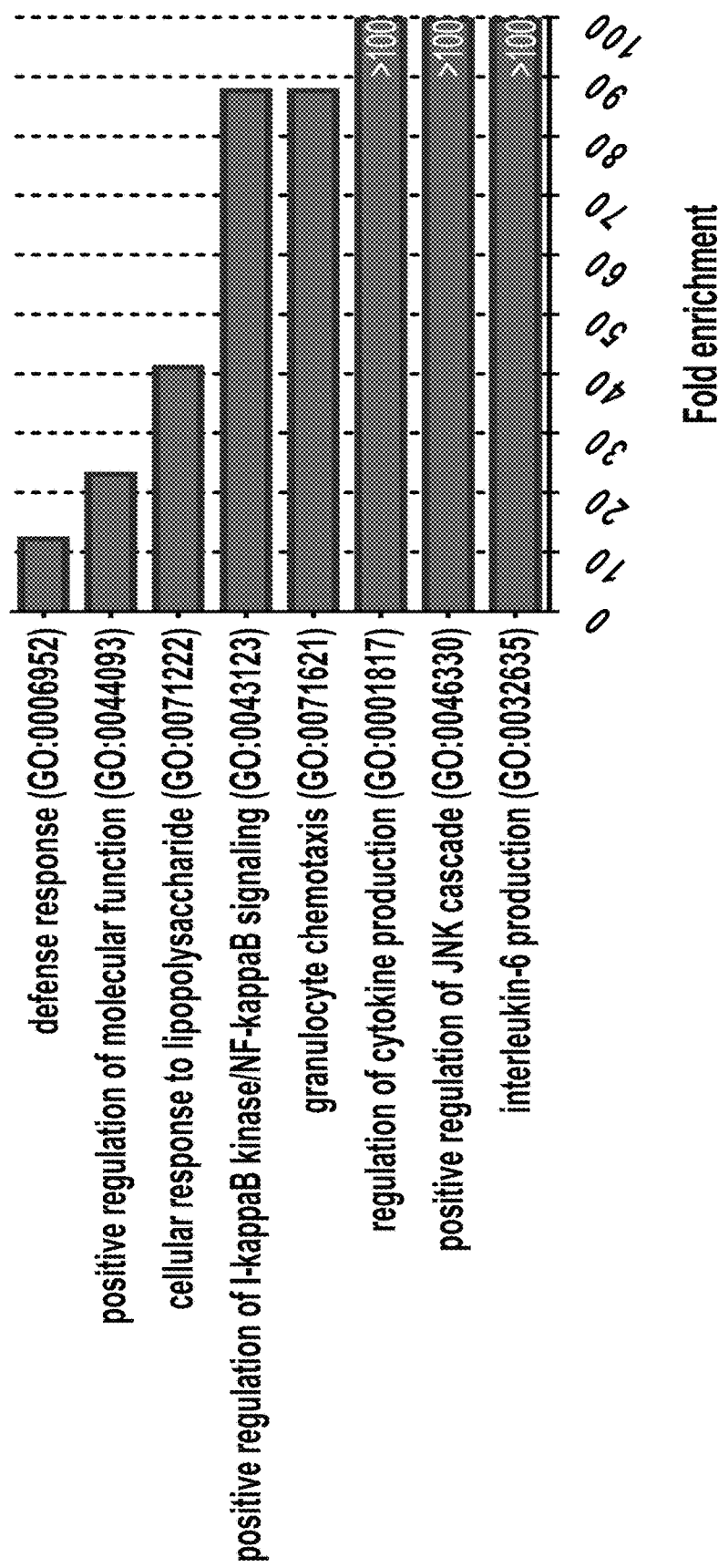
Figure 10A:
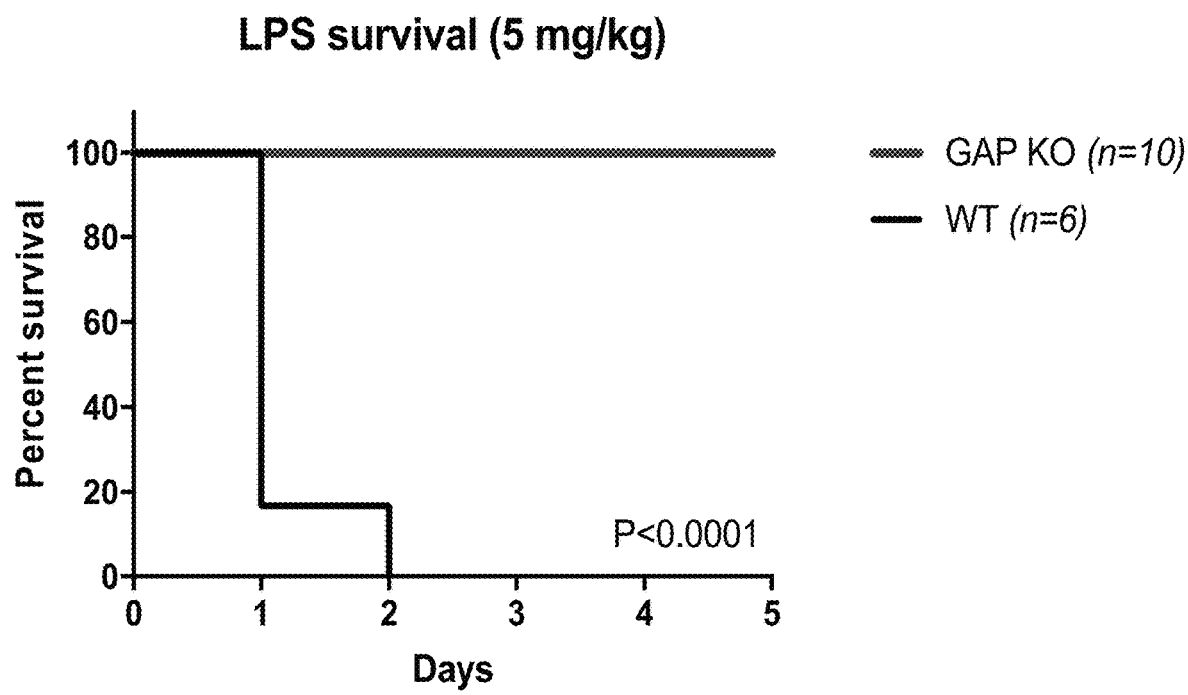
FIGS. 10A and 10B are survival plots showing the results where WT and GAPLINC−/− (GAP KO) mice were administered 5 mg/kg LPS (FIG. 10A) or 20 mg/kg LPS (FIG.
Figure 10B:
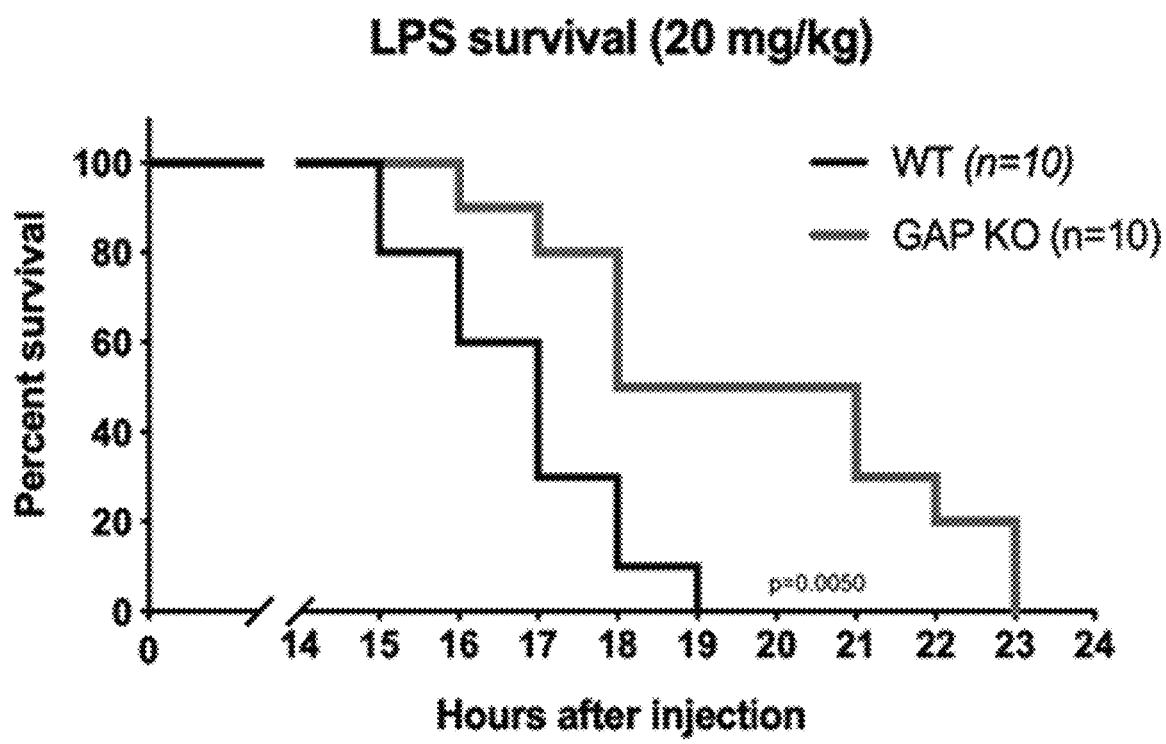

Using CRISPR, we generated a Gaplinc knockout (KO) mouse in which Exon 1 and the majority of the first intron was removed (FIG. 17C). Gaplinc-KO mice bred normally and displayed no obvious developmental defects. The deletion of Gaplinc was confirmed by PCR amplification of genomic DNA in WT and Gaplinc-KO mice, with amplicon sizes ~1300 bp for WT and ~500 bp for Gaplinc-KO mice (FIG. 17C). Full genotyping strategy to confirm WT and Gaplinc knockouts are highlighted (FIG. 19). We also confirmed Gaplinc deficiency in BMDMs using qPCR (FIG. 9B). To assess if Gaplinc deficiency affected differentiation, we stained WT and Gaplinc-KO BMDMs for CD11B and F4/80. Staining patterns were similar, suggesting normal macrophage differentiation (FIG. 20A). To assess if Gaplinc-KO disrupted macrophage function, we compared phagocytosis activity in WT and Gaplinc-KO BMDMs and found no differences (FIG. 20B).

Example 5—Impact of Gaplinc Deficiency in Macrophages

To assess the global impact of Gaplinc deficiency in macrophages, we performed RNA-seq on WT and Gaplinc-KO BMDMs, both untreated and LPS-stimulated for 6 h. Gaplinc-KO BMDMs significantly upregulated the expression of 23 genes basally (FIG. 17G) and 2730 genes post- LPS. Genes significantly upregulated in the absence of an inflammatory stimulation include proinflammatory cytokines and chemokines (Il6, Il1α, Il1β, Cxcl10), IFN-stimulated genes (ISGs) (Ifit1bl1), GBP-family members (Gbp5, Gbp10), and cell surface markers specific for activated macrophages (Cd69). GO analysis confirmed that genes involved in the immune response are overrepresented in Gaplinc-KO BMDMs (FIG. 17H). These genes are typically upregulated following LPS stimulation (FIG. 21). Similar to data obtained from our human studies, this data suggests that GAPLINC is functionally conserved across species to basally control the expression of inflammatory response genes (IRGs).

Example 6—LncRNAs Regulate the Transcription of Neighboring Genes

Numerous studies have shown the ability of lncRNAs to regulate the transcription of neighboring genes[15]. As such, we explored potential cis-regulatory roles for Gaplinc as its neighboring gene Tgif1 has been previously implicated in modulating macrophage activation[16]. Using our RNA-seq data, we confirmed that Gaplinc-KO BMDMs did not affect the expression of Tgif1 relative to WT cells (FIG. 22A). We further confirmed by qPCR that Tgif1 was unaltered in Gaplinc knockouts (FIG. 22B). Next, we explored the possibility that disruption of the Gaplinc locus could remove an important regulatory element, such as an enhancer. We utilized ATAC-seq data from WT BMDMs to assess transcriptionally active regions in the Gaplinc locus[17]. We did not identify signals within the Gaplinc deletion region, only those corresponding to the Gaplinc promoter (FIG. 23). Collectively, this data suggests that upregulation of IRGs upon Gaplinc deficiency is not due to effects on neighboring genes or removal of a regulatory element.

Example 7—In Vivo Experiment in Gaplinc-KO Animals

As Gaplinc-KO BMDMs upregulate the expression IRGs under basal conditions, we next wanted to challenge Gaplinc-KO animals in vivo to observe differences in host response. We employed an "endotoxic shock" model in which. E. coli LPS was intraperitoneally injected (i.p.) into WT and Gaplinc KO mice to measure differences in survival. At a dose of 5 mg/kg/mouse, WT mice showed 0% survival after 2 days (FIG. 17I). However, 100% of Gaplinc-KO mice survived, which suggests Gaplinc KO mice are resistant to LPS induced endotoxic shock (FIG. 17I). Notably, significant temperature differences between WT and Gaplinc-deficient mice are observed. Collectively, this data shows Gaplinc plays an important role in regulating the immune response in vivo.

Example 8—Changes in Cytokine Expression

From our human studies we know that GAPLINC can regulate immune genes at baseline. Therefore, to better understand these survival differences, we assessed for changes in cytokine expression at baseline. We utilized a multiplexed cytokine array to simultaneously measure biomarkers associated with the immune response, sepsis and cancer. At basal, key immune genes including MDC, MIP-la, IL-13, IL-5, M-CSF were significantly elevated in the serum of Gaplinc-KO mice compared to WT (FIG. 24A). These cytokines are implicated in cell recruitment; however, using flow cytometry, we confirmed the percentage of neutrophils, T cells, B cells, eosinophils, monocytes, and macrophages were comparable between WT and Gaplinc-KO mice at baseline (FIGS. 25A and 25B). Interestingly, these percentages were also comparable post-LPS challenge at the 6 h and 18 h time points (FIGS. 26A, 26B, and 27A-27C). Further, serum from WT and Gaplinc-KO mice tested for clinical features of sepsis, including lactate and CRP (FIG. 28) showed no differences.

As increased levels of MDC or IL-13 (FIG. 24A) have been previously characterized to play protective roles against endotoxic shock through modulation of proinflammatory cytokines[18,19], we next examined for differences in proinflammatory cytokine levels including Il6, Il1α, Il1β, and Cxcl10. While WT and Gaplinc-KO levels are the same at both the transcript (FIG. 24B) and protein level (FIG. 29A-29C), the magnitude of change is much lower (FIG. 24C), suggesting that this reduced fold-change may play a role in preventing the susceptibility of Gaplinc-KO mice to LPS induced endotoxic shock.

Example 9—Study of Coagulation Differences

Along with the rampant production of cytokines, another clinical aspect of endotoxic shock that can lead to mortality is the formation of blood clots in the smaller vessels, leading to multiorgan failure[20, 21]. To address this, we analyzed the serum of LPS i.p. treated mice to assess differences in coagulation. Using an activated partial thromboplastin time (aPTT) assay that measures time to clot formation, we find that WT mice show a significantly prolonged aPTT time compared to Gaplinc-KO mice upon LPS challenge (FIG. 24D). Prolonged aPTT times suggests WT mice have already undergone coagulation and depleted key coagulation factors, such that at the time of testing, initiating clotting and measuring time to clot formation is increased. The data suggest that differences in survival upon LPS challenge are due to WT mice undergoing increased clotting, leading to eventual organ failure and death.

Next, we tried to mechanistically understand how Gaplinc is mediating this effect. First, we confirmed its localization and analyzed Gaplinc levels in both the cytoplasmic and nuclear compartments of BMDMs by qPCR. Similar to human GAPLINC, mouse Gaplinc was predominantly cytoplasmic (FIG. 30). Next, we performed modified-ChIRP coupled with mass spectrometry and small RNA sequencing, as GAPLINC has been previously shown to interact with miRNAs (7). We did not observe interactions with previously identified targets (FIGS. 31A and 31B).

As we could not identify a direct binding partner, we focused on the conserved function between human and mouse, specifically the conserved genes impacted in our human GAPLINC knockdown and mouse Gaplinc knockout studies, the majority of which are NF-κB regulators (FIG. 24E). The most abundant form of NF-κB activated by LPS is the p65:p50 heterodimer and 7 out of the 9 conserved genes are direct p65 targets22. We used native RIP and showed that there is no direct interaction between Gaplinc and p65 (FIG. 32). In the classical NF-κB signaling pathway, the p65:p50 subunits are located in the cytosol and bound to inhibitory IκBα in resting cells. Upon activation, IκBα is degraded, allowing p65:p50 to translocate into the nucleus and activate target genes23. In WT and Gaplinc-KO BMDMs, we measured the degradation of IκBα using Western Blot and found no differences (FIG. 24F). Next, we compared total p65 levels in BMDMs. In our RNA-seq data, p65 (RelA) transcript levels in both the basal and LPS-stimulated conditions for WT and Gaplinc-KO BMDMs are comparable (FIG. 33). However, when we compared total p65 protein levels by Western Blot, we found significantly increased p65 levels in Gaplinc-KO cells compared to WT (FIG. 24G). This suggests that Gaplinc regulates total p65 levels at the translational level. Additionally, we assessed p65 levels in the cytoplasmic and nuclear compartments and found that nuclear p65 is more abundant in Gaplinc-deficient cells compared to WT (FIG. 24G). Combined, this data suggests a mechanistic role for GAPLINC in priming the activation of critical inflammatory response genes. In comparison to reported cytosolic lncRNAs that impact translational efficiency by modulating protein expression or ribosome assembly[24,25,26], we find Gaplinc is cytosolically contributing to p65 translational ability; however, the mechanism of interaction, either direct or indirect, remains to be determined. Our findings provide novel insights into how a functionally conserved lncRNA regulates the immune response and provides new avenues of investigation for the development of therapeutics for endotoxic shock.

REFERENCES

1. ENCODE Project Consortium. An integrated encyclopedia of DNA elements in the human genome. *Nature* 489, 57-74 (2012).
2. Chen, Y. G., Satpathy, A. T. & Chang, H. Y. Gene regulation in the immune system by long noncoding RNAs. *Nat. Immunol.* 18, 962-972 (2017).
3. Hu, Y. et al. Long noncoding RNA GAPLINC regulates CD44-dependent cell invasiveness and associates with poor prognosis of gastric cancer. *Cancer Res.* 74, 6890-6902 (2014).
4. Wu, X. et al. Long Non-Coding RNA ucoo2kmd.1 Regulates CD44-Dependent Cell Growth by Competing for miR-211-3p in Colorectal Cancer. *PLoS One* 11, e0151287 (2016).
5. CDC. Data and reports. *Centers for Disease Control and Prevention* (2020).
6. Goffs, J. E. & Matthay, M. A. Sepsis: pathophysiology and clinical management. *BMJ* 353, i1585 (2016).
7. Pellegrina, D. V. da S. et al. Insights into the Function of Long Noncoding RNAs in Sepsis Revealed by Gene Co-Expression Network Analysis. *Noncoding RNA* 3, (2017).
8. Wang, P. et al. The STAT3-binding long noncoding RNA lnc-DC controls human dendritic cell differentiation. *Science* 344, 310-313 (2014).
9. Ranzani, V. et al. The long intergenic noncoding RNA landscape of human lymphocytes highlights the regulation of T cell differentiation by linc-MAF-4. *Nat. Immunol.* 16, 318-325 (2015).
10. Carpenter, S. et al. A long noncoding RNA mediates both activation and repression of immune response genes. *Science* 341, 789-792 (2013).
11. Li, Z. et al. The long noncoding RNA THRIL regulates TNFα expression through its interaction with hnRNPL. *Proc. Natl. Acad. Sci. USA* 111, 1002-1007 (2014).
12. Medzhitov, R. & Homg, T. Transcriptional control of the inflammatory response. *Nat. Rev. Immunol.* 9, 692-703 (2009).
13. Gu, H., Chen, J., Song, Y. & Shao, H. Gastric Adenocarcinoma Predictive Long Intergenic Non-Coding RNA Promotes Tumor Occurrence and Progression in Non-Small Cell Lung Cancer via Regulation of the miR-661/eEF2K Signaling Pathway. *Cell. Physiol. Biochem.* 51, 2136-2147 (2018).
14. Han, X. et al. Mapping the Mouse Cell Atlas by Microwell-Seq. *Cell* 172, 1091-1107.e17 (2018).
15. Engreitz, J. M. et al. Local regulation of gene expression by lncRNA promoters, transcription and splicing. *Nature* 539, 452-455 (2016).
16. Ramsey, S. A. et al. Uncovering a macrophage transcriptional program by integrating evidence from motif scanning and expression dynamics. *PLoS Comput. Biol.* 4, e1000021 (2008).
17. Atianand, M. K. et al. A Long Noncoding RNA lincRNA-EPS Acts as a Transcriptional Brake to Restrain Inflammation. *Cell* 165, 1672-1685 (2016).
18. Matsukawa, A. et al. Pivotal role of the CC chemokine, macrophage-derived chemokine, in the innate immune response. *J. Immunol.* 164, 5362-5368 (2000).
19. Muchamuel, T., Menon, S., Pisacane, P., Howard, M. C. & Cockayne, D. A. IL-13 protects mice from lipopolysaccharide-induced lethal endotoxemia: correlation with down-modulation of TNF-alpha, IFN-gamma, and IL-12 production. *J. Immunol.* 158, 2898-2903 (1997).
20. Rittirsch, D., Flierl, M. A. & Ward, P. A. Harmful molecular mechanisms in sepsis. *Nat. Rev. Immunol.* 8, 776-787 (2008).
21. Korneev, K. V. [Mouse Models of Sepsis and Septic Shock]. *Mol. Biol.* 53, 799-814 (2019).
22. Tong, A.-J. et al. A Stringent Systems Approach Uncovers Gene-Specific Mechanisms Regulating Inflammation. *Cell* 165, 165-179 (2016).
23. Karin, M. & Ben-Neriah, Y. Phosphorylation meets ubiquitination: the control of NF-[kappa]B activity. *Annu. Rev. Immunol.* 18, 621-663 (2000).
24. Faghihi, M. A. et al. Expression of a noncoding RNA is elevated in Alzheimer's disease and drives rapid feed-forward regulation of beta-secretase. *Nat. Med.* 14, 723-730 (2008).
25. Miao, H. et al. A long noncoding RNA distributed in both nucleus and cytoplasm operates in the PYCARD-regulated apoptosis by coordinating the epigenetic and translational regulation. *PLoS Genet.* 15, e1008144 (2019).
26. Carrieri, C. et al. Long non-coding antisense RNA controls Uchl1 translation through an embedded SINEB2 repeat. *Nature* 491, 454-457 (2012).
27. Ray, A. & Dittel, B. N. Isolation of mouse peritoneal cavity cells. *J. Vis. Exp.* (2010) doi:10.3791/1488.
28. Chu, C. & Chang, H. Y. ChIRP-MS: RNA-Directed Proteomic Discovery. *Methods Mol. Biol.* 1861, 37-45 (2018).
29. Wang, P., Xu, J., Wang, Y. & Cao, X. An interferon-independent lncRNA promotes viral replication by modulating cellular metabolism. *Science* 358, 1051-1055 (2017).

One or more features from any embodiments described herein or in the figures may be combined with one or more features of any other embodiment described herein in the figures without departing from the scope of the disclosure.

All publications, patents and patent applications cited in this specification are herein incorporated by reference as if each individual publication or patent application were specifically and individually indicated to be incorporated by reference. Although the foregoing disclosure has been described in some detail by way of illustration and example for purposes of clarity of understanding, it will be readily apparent to those of ordinary skill in the art in light of the teachings of this disclosure that certain changes and modifications may be made thereto without departing from the spirit or scope of the appended claims.

What is claimed:

1. An inhibitory agent comprising at least 20 nucleosides in length, wherein the inhibitory agent is complementary to an equal length portion of a sequence of a GAPLINC RNA, wherein the inhibitory agent inhibits the expression of the Gastric Adenocarcinoma Predictive Long Intergenic Non-Coding (GAPLINC) RNA, wherein the inhibitory agent further comprises at least one modified nucleobase, at least one modified internucleoside linkage, and/or at least one modified sugar.

2. The inhibitory agent of claim 1, wherein the GAPLINC RNA is a human GAPLINC RNA or a mouse GAPLINC RNA.

3. The inhibitory agent of claim 1, wherein the GAPLINC RNA comprises a sequence having at least 90% identity to the sequence of:

ACTTGCAGGATCTGACACATCCTCTTGGTTTCCTAAGTCTTATGACTAGCCAATGCCT GAAATAATGAACTCCTCCAAGGCAAGAAATCTGTTTTGAAGCTTCTCTGCGTTCACA CACAGCAGCCTGGTTTCCTGGAAGGGCATTTTCCACATTGTGCGTTATGGATGATCA TCCCAGGCATCAGGTGTGAAGCCCTGCATCCACATCCAGGGGCTATCAAATCTCTCT GCAAAAGGAGAAGCTGGACTCAGGCACGTTTACAGTGATGTGTATGCAGGCTGGAA TGCAGGGATGCGATCTCGGCTCAATGCAACCTCTGCCGCCCAGGATTCAAGCGATTC TCCTGCCTCAGCTTCTTGAGTATCTGGGATTACAGGCACCTGCCACCACGCCTGACT AATTTTTGTAGTTTTAGTAGAGCCAGGGTTTCACCATCTTGGCCAGGCTGGTCTTGAA CTCCTGACCTCGTGATCCACCCACCTTGTCTTCCCAAAGTGCTGCGATTACAGGCGT GAGCCACCGTGCCCGGCTGACCAGTATCTTTCATGTTACTATTGTAATTGTTTGGGGT CACCACGAACCGCACACATATAAGACAATGAACTTAATCAATAAACGTGTGTGTTCT GATTGCTCCATTCTGTGAAGGAAGCTGCAGAAGAAAAAGGTGAAAGAGGTGAGGAA GCTGCAGAAGAAAACCTGGAAGTTAGCAGAGCTTGATCCAGAGGTTTAAGGAAAGA AGCCATCTCCATAACATAAAAGTGCAAGGTGAAGCAGCAAGTGCTGATGGGGAAGC TGCAGCAAGTCATCCAGAAGATCTTGCTAAGGGTATGCACAGATGTGGAAACAGGA ACTGATGTGTCCATTACACCACTAGGACAGAGGCCAGAACAATGAAGAAACCAAAT ACTTGGAAGAGGGTAGAGATAATGAATGGAGTCCAAGAGCCCTGATTGTGCCATAA ATGTCCAGATAATTCCATACCTGAGGATTATGTGGTTTGTAAACTTGGCACTTAGAA GAACCAATAAAATCATGTTATAGTTTCAA (SEQ ID NO:1), or

AGCTCGGGAAGCCTGCAGGCTGTGAGCACGTTGATCAAAGGTCCCTTTGCGGGCTCA AATTAACAGGGAGCTGGCGAGCCCGCGCAGCACCTGCCTGGGAAGAGCAGCGCCAC AGCAAACCGGCTCATCTTGCCGGGAGTATTTGGAAATGAACCTTGGACTTTAAGAAC GCTTGGAGTCATTGAACCACACCCAACTCCTATTCTGACATTTCACTGCTATCCAGG ATTTACAGAAAATGTTAGAAAAACTCTGCAGCAATGTTATTTTGAAATTTATAAAGC CTTTACAAAAATGTGAAGAAAGATGTATATATTTGTGGCATCTTGATCTCTACTATA AATTGCGAAATGATTGGATTGAGCTTAAGGTATTAAAGCTTTTA (SEQ ID NO:2).

4. The inhibitory agent of claim 1, comprising between 20 and 30 nucleosides in length.

5. The inhibitory agent of claim 1, wherein the inhibitory agent comprises an antisense oligonucleotide (ASO), an siRNA, an miRNA, or an shRNA.

6. The inhibitory agent of claim 5, wherein the inhibitory agent comprises an ASO.

7. The inhibitory agent of claim 6, wherein the ASO comprises a sequence having at least 90% identity to a sequence of any one of:

(SEQ ID NO: 3)
AUGUGGAUGCAGGGCUUCAC, (SEQ ID NO: 4)
AUGUGGAAAAUGCCCUUCCA, (SEQ ID NO: 5)
AGUCCAGCUUCUCCUUUUGC, (SEQ ID NO: 6)
CUUGCCUUGGAGGAGUUCAU,
and (SEQ ID NO: 7)
GAUGCCUGGGAUGAUCAUCC.

8. The inhibitory agent of claim 5, wherein the inhibitory agent comprises an siRNA.

9. The inhibitory agent of claim 8, wherein the siRNA comprises a sense region and an antisense region.

10. The inhibitory agent of claim 9, wherein the antisense region comprises a sequence having at least 90% identity to a sequence of any one of:

(SEQ ID NO: 9)
UUUGGUUUCUUCAUUGUUCTG, (SEQ ID NO: 11)
GAAGAAAACCUGGAAGUUAUU, (SEQ ID NO: 13)
UUUACAAACCACAUAAUCCUC, (SEQ ID NO: 15)
UUUGGUUUCUUCAUUGUUC,

-continued

```
                                    (SEQ ID NO: 17)
GAAGAAAACCUGGAAGUUA,
and (SEQ ID NO: 19)
UUUACAAACCACAUAAUCC;
``` and/or wherein the sense region comprises a sequence having at least 90% identity to a sequence of:

```
                                    (SEQ ID NO: 8)
GAACAAUGAAGAAACCAAATT, (SEQ ID NO: 10)
GAAGAAAACCUGGAAGUUATT, (SEQ ID NO: 12)
GGAUUAUGUGGUUUGUAAATT, (SEQ ID NO: 14)
GAACAAUGAAGAAACCAAA, (SEQ ID NO: 16)
GAAGAAAACCUGGAAGUUA,
and (SEQ ID NO: 18)
GGAUUAUGUGGUUUGUAAA.
```

11. The inhibitory agent of claim 1, wherein the inhibitory agent comprises a phosphorodiamidate morpholino oligomer (PMO).

12. The inhibitory agent of claim 1, wherein the inhibitory agent comprises a peptide nucleic acid.

13. The inhibitory agent of claim 6, wherein the ASO comprises at least one, at least two, at least three, at least four, at least five, at least six, at least seven, at least eight, at least nine, or at least ten modified nucleotides each comprising a 2'-OMe.

14. The inhibitory agent of claim 13, wherein the ASO comprises at least five modified nucleotides each comprising a 2'-OMe and wherein the first five nucleotides from the 5' terminus of a sequence of any one of SEQ ID NOS:3-7 each comprises a modified nucleotide comprising a 2'-OMe.

15. The inhibitory agent of claim 13, wherein the ASO comprises at least ten modified nucleotides each comprising a 2'-OMe and wherein the first five nucleotides and the last five nucleotides from the 5' terminus of a sequence of any one of SEQ ID NOS:3-7 each comprises a modified nucleotide comprising a 2'-OMe.

16. The inhibitory agent of claim 6, wherein the inhibitory agent comprises at least one phosphorothioate linkage.

17. A pharmaceutical composition comprising an inhibitory agent of claim 1 and one or more pharmaceutically acceptable carriers or excipients.

18. A method of treating an inflammatory disease in a subject, the method comprising administering to the subject a therapeutically effective amount of an inhibitory agent of claim 1, wherein the inhibitory agent inhibits the expression of the GAPLINC RNA.

19. A method of inhibiting the expression of a GAPLINC RNA in a subject, comprising administering to the subject a therapeutically effective amount of an inhibitory agent of claim 1, wherein the inhibitory agent inhibits the expression of the GAPLINC RNA.

* * * * *